US011814635B2

(12) United States Patent
Christensen et al.

(10) Patent No.: US 11,814,635 B2
(45) Date of Patent: Nov. 14, 2023

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 87 days.

(21) Appl. No.: 17/222,626

(22) Filed: Apr. 5, 2021

(65) Prior Publication Data

US 2021/0324400 A1 Oct. 21, 2021

Related U.S. Application Data

(60) Division of application No. 16/659,220, filed on Oct. 21, 2019, now Pat. No. 11,021,714, which is a division of application No. 16/275,629, filed on Feb. 14, 2019, now Pat. No. 10,508,284, which is a division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.
| | |
|---|---|
| *C12N 15/82* | (2006.01) |
| *C07K 14/415* | (2006.01) |
| *A01H 1/02* | (2006.01) |
| *C12Q 1/6895* | (2018.01) |

(52) U.S. Cl.
CPC .......... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,990,387 | A | 11/1999 | Tomes et al. |
| 7,244,879 | B2 | 7/2007 | Christensen et al. |
| 10,240,166 | B2 | 3/2019 | Christensen et al. |
| 10,508,284 | B2 | 12/2019 | Christensen et al. |
| 10,696,979 | B2 | 6/2020 | Christensen et al. |
| 11,021,714 | B2 | 6/2021 | Christensen et al. |
| 11,034,973 | B2 | 6/2021 | Christensen et al. |
| 11,459,580 | B2 | 10/2022 | Christensen et al. |
| 2004/0031072 | A1 | 2/2004 | La Rosa et al. |
| 2006/0107345 | A1 | 5/2006 | Alexandrov et al. |
| 2006/0150283 | A1 | 7/2006 | Alexandrov et al. |
| 2009/0094717 | A1 | 4/2009 | Troukhan et al. |
| 2009/0241208 | A1 | 9/2009 | Christensen et al. |
| 2009/0265275 | A1 | 10/2009 | Alexandrov et al. |
| 2009/0265815 | A1 | 10/2009 | Alexandrov et al. |
| 2010/0083407 | A1 | 4/2010 | Feldmann et al. |
| 2015/0259699 | A1* | 9/2015 | Nadzan ............... C12Q 1/6895 800/267 |
| 2016/0369294 | A9 | 12/2016 | Nadzan et al. |
| 2018/0223303 | A1 | 8/2018 | Alexandrov et al. |
| 2020/0131525 | A1 | 4/2020 | Christensen et al. |
| 2020/0255853 | A1 | 8/2020 | Christensen et al. |
| 2021/0388371 | A1 | 12/2021 | Christensen et al. |

FOREIGN PATENT DOCUMENTS

| | | |
|---|---|---|
| EP | 1033405 | 9/2000 |
| WO | WO 99/02687 A2 | 1/1999 |
| WO | WO 2004/035798 A2 | 4/2004 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
U.S. Appl. No. 17/314,977, filed May 7, 2021, Christensen et al.
Didierjean et al., Heavy-metal-responsive genes in maize: identification and comparison of their expression upon various forms of abiotic stress, Planta 199:1-8, 1996.
GenBank Accession No. AK118678.1, dated Feb. 14, 2004.
Kim et al., "Molecular cloning of low temperature-inducible ribosomal proteins from soybean," *Journal of Experimental Botany* 55:1153-1155, 2004.
Lu et al., "*Arabidopsis* Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.

(Continued)

*Primary Examiner* — Vinod Kumar
(74) *Attorney, Agent, or Firm* — DENTONS US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

13 Claims, 8 Drawing Sheets

Specification includes a Sequence Listing.

(56) References Cited

OTHER PUBLICATIONS

Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.
USPTO: Notice of Allowance regarding U.S. Appl. No. 16/275,659 dated Feb. 28, 2020.
USPTO: Notice of Allowance and Fee(s) Due regarding U.S. Appl. No. 16/275,629, dated Aug. 2, 2019.
USPTO: Office Action regarding U.S. Appl. No. 16/275,659, dated Dec. 19, 2019.
Response to Office Action regarding U.S. Appl. No. 16/275,659, dated Feb. 4, 2020.
Supplemental Response to Office Action regarding U.S. Appl. No. 16/275,659, dated Feb. 11, 2020.

* cited by examiner

| | | | | | |
|---|---|---|---|---|---|
| SEQ-ID-NO-17-CLONE-839727 | MSAAE---GA | VVFSEEKEAL | VLKSWAIMKK | DSANLGLRFF | LKIFEIAPSA | 47 |
| SEQ-ID-NO-16-CLONE-1554560 | MALAEADDGA | VVFGEEQEAL | VLKSWAVMKK | DAANLGLRFF | LKVFEIAPSA | 50 |
| SEQ-ID-NO-60-CLONE-1802327 | MALAE---GN | VIFGEEQEAL | VLKSWALMKK | DSADLGLRFF | LKIFEIAPSA | 47 |
| SEQ-ID-NO-9-CLONE-30469-FL | -MESE---GK | -VFTEEQEAL | VVKSWSVMKK | NSAELGLKLF | LKIFEIAPTT | 46 |
| SEQ-ID-NO-10-GI-30909306 | -MESE---GK | -VFTEEQEAL | VVKSWNVMKK | NSADLGLKLF | LKIFEIAPTA | 46 |
| SEQ-ID-NO-13-CLONE-546001 | -MTTTLERG- | -FSEEEQEAL | VVKSWNVMKK | NSGELGLKFF | LKIFEIAPSA | 46 |
| SEQ-ID-NO-70-CLONE-1916866 | MAIYE---GK | -VFTEEQEAL | VVKSWTVMKK | NAAELGLKFF | LKIFEIAPSA | 46 |

| | | | | | |
|---|---|---|---|---|---|
| SEQ-ID-NO-17-CLONE-839727 | RQMFPFLRDS | DVPLETNPKL | KTHAVSVFVM | TCEAAAQLRK | AGKITVRETT | 97 |
| SEQ-ID-NO-16-CLONE-1554560 | KQMFSFLRDS | DVPLEKNPKL | KTHAMSVFVM | TCEAAAQLRK | AGKVTVRETT | 100 |
| SEQ-ID-NO-60-CLONE-1802327 | KQMFSFLRDS | DVPLEKNPKL | KNHAMSVFVM | TCEAAAQLRK | AGKVTVRETT | 97 |
| SEQ-ID-NO-9-CLONE-30469-FL | KKMFSFLRDS | PIPAEQNPKL | KPHAMSVFVM | CCESAVQLRK | AGKVTVRETT | 96 |
| SEQ-ID-NO-10-GI-30909306 | QKLFSFLRDS | PIPAEQNPKL | KPHAVSVFVM | CCESAVQLRK | TGKVTVKETT | 96 |
| SEQ-ID-NO-13-CLONE-546001 | KKLFSFLRDS | TVPLEQNPKL | KPHAMSVFVM | TCDSAVQLRK | TGKVTVRESN | 96 |
| SEQ-ID-NO-70-CLONE-1916866 | KKLFSFLRDS | NVPLEQNTKL | KPHAMSVFVM | TCESAVQLRK | AGKVTVRESN | 96 |

| | | | | | |
|---|---|---|---|---|---|
| SEQ-ID-NO-17-CLONE-839727 | LKRLGGTHLK | YGVADGHFEV | TRFALLETIK | EALPADMWGP | EMRNAWGEAY | 147 |
| SEQ-ID-NO-16-CLONE-1554560 | LKRLGATHLR | YGVADGHFEV | TGFALLETIK | EALPADMWSL | EMKKAWAEAY | 150 |
| SEQ-ID-NO-60-CLONE-1802327 | LKRLGATHFK | YGVADGHFEV | TRFALLETIK | EALPADMWSL | EMKNAWSEAY | 147 |
| SEQ-ID-NO-9-CLONE-30469-FL | LKRLGASHSK | YGVDEHFEV  | AKYALLETIK | EAVP-EMWSP | EMKSAWGQAY | 145 |
| SEQ-ID-NO-10-GI-30909306 | LKRLGANHSK | YGVDEHFEV  | TKYALLETIK | EAVP-EMWSP | EMKVAWGQAY | 145 |
| SEQ-ID-NO-13-CLONE-546001 | LKKLGATHFR | TGVANEHFEV | TKFALLETIK | EAVP-EMWSP | AMKNAWGEAY | 145 |
| SEQ-ID-NO-70-CLONE-1916866 | LKKLGATHFK | YGVDEHFEV  | TKFALLETIK | EAVP-DMWSD | EMKNAWGEAY | 145 |

| | | | |
|---|---|---|---|
| SEQ-ID-NO-17-CLONE-839727 | DQLVAAIKQE | MKPSE---- | 162 |
| SEQ-ID-NO-16-CLONE-1554560 | SQLVAAIKRE | MKPDA---- | 165 |
| SEQ-ID-NO-60-CLONE-1802327 | NQLVAAIKQE | MKPAA---- | 162 |
| SEQ-ID-NO-9-CLONE-30469-FL | DHLVAAIKAE | MNLSN---- | 160 |
| SEQ-ID-NO-10-GI-30909306 | DHLVAAIKAE | MKPSH---- | 160 |
| SEQ-ID-NO-13-CLONE-546001 | DQLVDAIKSE | MKPPSS--- | 161 |
| SEQ-ID-NO-70-CLONE-1916866 | DRLVAAIKIE | MKACSQAA  | 163 |

FIGURE 3

|  |  |  |  |  |  |  |
|---|---|---|---|---|---|---|
| SEQ-ID-NO-221-CLONE-839727-T | MSAAE---GA | VVFSEEKEAL | VLKSWAIMKK | DSANLGLRFF | LKIFEIAPSA | 47 |
| SEQ-ID-NO-207-CLONE-1554560-T | MALAEADDGA | VVFGEEQEAL | VLKSWAVMKK | DAANLGLRFF | LKVFEIAPSA | 50 |
| SEQ-ID-NO-208-CLONE-1802327-T | MALAE---GN | VIFGEEQEAL | VLKSWALMKK | DSADLGLRFF | LKIFEIAPSA | 47 |
| SEQ-ID-NO-7-CLONE-30469 | MESE---GK | VFTEEQEAL | VVKSWSVMKK | NSAELGLKLF | IKIFEIAPTA | 46 |
| SEQ-ID-NO-227-GI-30909306-T | MESE---GK | VFTEEQEAL | VVKSWSVMKK | NSADLGLKLF | IKIFEIAPTA | 46 |
| SEQ-ID-NO-219-CLONE-546001-T | MITT----LE | RGFSEEQEAL | VVKSWNVMKK | NSCELGLKFF | LKIFEIAPSA | 46 |
| SEQ-ID-NO-212-CLONE-1916866-T | MATY----EG | KVFTEEQEAL | VVKSWTVMKK | NAAELGLKFF | LKIFEIAPSA | 46 |

|  |  |  |  |  |
|---|---|---|---|---|
| SEQ-ID-NO-221-CLONE-839727-T | RQMFPFLRDS | DVPLEINPKL | KTHAVSVFVM | -- | 77 |
| SEQ-ID-NO-207-CLONE-1554560-T | KQMFSFLRDS | DVPLEKNPKL | KTHAMSVFVM | -- | 80 |
| SEQ-ID-NO-208-CLONE-1802327-T | KQMFSFLRDS | DVPLEKNPKL | KNHAMSVFVM | -- | 77 |
| SEQ-ID-NO-7-CLONE-30469 | KKMFSFLRDS | PIPAEQNPKL | KPHAMSVFVM | YN | 78 |
| SEQ-ID-NO-227-GI-30909306-T | KKLFSFLRDS | PIPAEQNPKL | KPHAMSVFVM | -- | 76 |
| SEQ-ID-NO-219-CLONE-546001-T | QKLFSFLRDS | TVPLEQNPKL | KPHAVSVFVM | -- | 76 |
| SEQ-ID-NO-212-CLONE-1916866-T | KKLFSFLRDS | NVPLEQNTKL | KPHAMSVFVM | -- | 76 |

FIGURE 4

| SEQ ID | | | | | | |
|---|---|---|---|---|---|---|
| SEQ-ID-NO-20-CLONE-271922  | MAKRTKKVGI | VGKYGTRYGA | SIRKQIKKME | VSQHSKYFCE | FCGKYGVKRK | 50 |
| SEQ-ID-NO-54-CLONE-1627907 | MTKRTKKAGI | VGKYGTRYGA | SLRKQIKKME | VSQHAKYFCE | FCGKYAVKRQ | 50 |
| SEQ-ID-NO-25-CLONE-664936  | MTKRTKKAGI | VGKYGTRYGA | SLRKQIKKME | VSQHSKFFCE | FCGKYAVKRK | 50 |
| SEQ-ID-NO-28-CLONE-632613  | MTKRTKKAGI | VGKYGTRYGA | SLRKQIKKME | VSQHSKYFCE | FCGKFAVKRK | 50 |
| SEQ-ID-NO-29-CLONE-1390976 | MTKRTKKAGI | VGKYGTRYGA | SLRKQIKKME | VSQHSKYFCE | FCGKFAVKRK | 50 |
| SEQ-ID-NO-58-CLONE-1783890 | MTKRTKKAGI | VGKYGTRYGA | SLRKQIKKME | VSQHSKYFCE | FCGKFAVKRK | 50 |

| SEQ ID | | | | | |
|---|---|---|---|---|---|
| SEQ-ID-NO-20-CLONE-271922  | AVGIWGCKDC | GKVKAGGAYT | MNTASAVTVR | STIRRLREQI | EG | 92 |
| SEQ-ID-NO-54-CLONE-1627907 | AVGIWGCKDC | GKVKAGGAYT | LNTASAVTVR | STIRRLREQT | ES | 92 |
| SEQ-ID-NO-25-CLONE-664936  | AVGIWGCKDC | GKVKAGGAYT | LNTASAVTVR | STIRRLREQT | EG | 92 |
| SEQ-ID-NO-28-CLONE-632613  | AVGIWGCKDC | GKVKAGGAYT | MNTASAVTVR | STIRRLREQT | EA | 92 |
| SEQ-ID-NO-29-CLONE-1390976 | AVGIWGCKDC | GKVKAGGAYT | MNTASAVTVR | STIRRLREQT | EA | 92 |
| SEQ-ID-NO-58-CLONE-1783890 | AVGIWGCKDC | GKVKAGGAYT | MNTASAVTVR | STIRRLREQT | EA | 92 |

FIGURE 5

| | | | | | | |
|---|---|---|---|---|---|---|
| SEQ-ID-NO-34-CLONE-2403-FL | MQIFVKTLTG | KTITLEVESS | DTIDNVKAKI | QDKEGIPPDQ | QRLIFAGKQL | 50 |
| SEQ-ID-NO-35-CLONE-1482731 | MQIFVKTLTG | KTITLEVESS | DTIDNVKSKI | QDKEGIPPDQ | QRLIFAGKQL | 50 |
| SEQ-ID-NO-36-CLONE-522921 | MQIFVKTLTG | KTITLEVESS | DTIDNVKAKI | QDKEGIPPDQ | QRLIFAGKQL | 50 |
| SEQ-ID-NO-37-CLONE-1036726 | MQIFVKTLTG | KTITLEVESS | DTIDNVKAKI | QDKEGIPPDQ | QRLIFAGKQL | 50 |
| SEQ-ID-NO-68-CLONE-1884696 | MQIFVKTLTG | KTITLEVESS | DTIDNVKAKI | QDKEGIPPDQ | QRLIFAGKQL | 50 |
| SEQ-ID-NO-80-CLONE-2034916 | MQIFVKTLTG | KTITLEVESS | DTIDNVKAKI | QDKEGIPPDQ | QRLIFAGKQL | 50 |

| | | | | | | |
|---|---|---|---|---|---|---|
| SEQ-ID-NO-34-CLONE-2403-FL | EDGRTLADYN | QKESTLHLV | LRLRGGTMIK | VKTLTGKEIE | DIEPTDTID | 100 |
| SEQ-ID-NO-35-CLONE-1482731 | EDGRTLADYN | QKESTLHLV | LRLRGGTMIK | VKTLTGKEIE | DIEPTDTID | 100 |
| SEQ-ID-NO-36-CLONE-522921 | EDGRTLADYN | QKESTLHLV | LRLRGGTMIK | VKTLTGKEIE | DIEPTDTID | 100 |
| SEQ-ID-NO-37-CLONE-1036726 | EDGRTLADYN | QKESTLHLV | LRLRGGTMIK | VKTLTGKEIE | DIEPTDTID | 100 |
| SEQ-ID-NO-68-CLONE-1884696 | EDGRTLADYN | QKESTLHLV | LRLRGGMQIF | VKTLTGKTIT | LEVESSDTID | 100 |
| SEQ-ID-NO-80-CLONE-2034916 | EDGRTLADYN | QKESTLHLV | LRLRGGMQIF | VKTLTGKTIT | LEVESSDTID | 100 |

| | | | | | | |
|---|---|---|---|---|---|---|
| SEQ-ID-NO-34-CLONE-2403-FL | RIKERVEEKE | GIPPVQQRLI | YAGKQLADDK | TAKDYAIEGG | SVLHLVLALR | 150 |
| SEQ-ID-NO-35-CLONE-1482731 | RIKERVEEKE | GIPPVQQRLI | YAGKQLADDK | TAKDYAIEGG | SVLHLVLALR | 150 |
| SEQ-ID-NO-36-CLONE-522921 | RIKERVEEKE | GIPPVQQRLI | YAGKQLADDK | TAKEYNIEGG | SVLHLVLALR | 150 |
| SEQ-ID-NO-37-CLONE-1036726 | RIKERVEEKE | GIPPVQQRLI | YAGKQLADDK | TXKDYNIEGG | SVSA------ | 144 |
| SEQ-ID-NO-68-CLONE-1884696 | NVKAKIQDKE | GIPPDQQRLI | FAGKQLEDGR | TLADYNIQKD | STLHLVLRLR | 150 |
| SEQ-ID-NO-80-CLONE-2034916 | NVKVKIQDKE | GIPPDQQRLI | FAGKQLEDGR | TLADYNIQKE | STLHLVRLR | 150 |

| | | | | | | |
|---|---|---|---|---|---|---|
| SEQ-ID-NO-34-CLONE-2403-FL | GGL------- | ---------- | ---------- | ---------- | ---------- | 153 |
| SEQ-ID-NO-35-CLONE-1482731 | GGS------- | ---------- | ---------- | ---------- | ---------- | 153 |
| SEQ-ID-NO-36-CLONE-522921 | GGT------- | ---------- | ---------- | ---------- | ---------- | 153 |
| SEQ-ID-NO-37-CLONE-1036726 | -SG------- | ---------- | ---------- | ---------- | ---------- | 146 |
| SEQ-ID-NO-68-CLONE-1884696 | GG-------- | ---------- | ---------- | ---------- | ---------- | 152 |
| SEQ-ID-NO-80-CLONE-2034916 | GGMQIFVKTL | TGKTITLEVE | SSDTIDNVKA | KIQDKEGIPP | DQQRLIFAGK | 200 |

| | | | | |
|---|---|---|---|---|
| SEQ-ID-NO-34-CLONE-2403-FL | ---------- | ---L | 154 |
| SEQ-ID-NO-35-CLONE-1482731 | ---------- | ---D | 154 |
| SEQ-ID-NO-36-CLONE-522921 | ---------- | ---Y | 154 |
| SEQ-ID-NO-37-CLONE-1036726 | ---------- | ---S | 147 |
| SEQ-ID-NO-68-CLONE-1884696 | ---------- | ---F | 153 |
| SEQ-ID-NO-80-CLONE-2034916 | QLEDGRTLAD | YNI | 213 |

FIGURE 6

| | | | | | |
|---|---|---|---|---|---|
| SEQ-ID-NO-40-CLONE-2403 | MQI FVKTLTG | KTI TLEVESS | DTI DNVKAKI | QDK | 33 |
| SEQ-ID-NO-205-CLONE-1036726-T | MQI FVKTLTG | KTI TLEVESS | DTI DNVKAKI | QDK | 33 |
| SEQ-ID-NO-211-CLONE-1884696-T | MQI FVKTLTG | KTI TLEVESS | DTI DNVKAKI | QDK | 33 |
| SEQ-ID-NO-213-CLONE-1950105-T | MQI FVKTLTG | KTI TLEVESS | DTI DNVKAKI | QDK | 33 |
| SEQ-ID-NO-218-CLONE-522921-T | MQI FVKTLTG | KTI TLEVESS | DTI DNVKAKI | QDK | 33 |
| SEQ-ID-NO-206-CLONE-1482731-T | MQI FVKTLTG | KTI TLEVESS | DTI DNVKSKI | QDK | 33 |

SEQUENCE LISTING

<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1

```
aactttctc tcccactctt tcttttacta ctctcacaca tatctctgtc tatatatcac      60
tttacataaa ccactattcc acacacaaac acacatagcc atggcctctt ctttctcttc     120
acaagccttc ttcttgctca cattgtctat ggttttaatt cctttctctt tagctcaagc    180
tcccatgatg gctccttctg gctcaatgtc catgccgcct atgtctagcg gcggtggaag    240
ctcggttcct cctccagtga tgtctccgat gccaatgatg actccaccac ctatgcctat    300
gactccatca cccatgccca tgactccacc acctatgcct atggctccac caccaatgcc    360
catggcttca ccaccaatga tgccaatgac tccatctaca agcccaagcc cattaacagt    420
tccggatatg ccttcgccgc cgatgccatc cggaatggaa tcttcacctt ctccaggacc    480
catgccaccg gcaatggcgg cttcgccgga ttcgggagct ttcaatgtta gaaacaacgt    540
cgtaacactt tcatgcgttg ttggagttgt tgcagctcat tttctcctcg tttgaaatga    600
ttattgaatt ggtcagcctc gatcgttttc ttgtaattta ctttcatatt ttttttccct    660
caaattatta gtggtcatca ttttataata tttgagtttg tgtttgatgt acgattcaga    720
catttgtttg cattatgtgc ttaataagtt tatcgttgac tctacttgaa gagagacttt    780
gtgtgtgatg taaatttctt ctatctatgg aacattgcat tcgtagcc                 828
```

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

```
<400> SEQUENCE: 2

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Ser Ser
        35                  40                  45

Val Pro Pro Pro Val Met Ser Pro Met Pro Met Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
                100                 105                 110

Pro Pro Met Pro Ser Gly Met Glu Ser Ser Pro Ser Pro Gly Pro Met
            115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
            20                  25                  30

Met Ser Met Pro Pro Met Pro Ser Gly Gly Ser Pro Met Pro Met Met
        35                  40                  45

Thr Pro Pro Pro Met Pro Met Met Thr Pro Pro Pro Met Ala Met Ala
    50                  55                  60

Pro Pro Pro Met Pro Met Thr Pro Pro Pro Met Pro Met Ala Pro Met
65                  70                  75                  80

Pro Met Thr Pro Ser Ser Ser Pro Met Ser Pro Pro Thr Thr Met Ala
                85                  90                  95

Pro Ser Pro Glu Thr Val Pro Asp Met Ala Ser Pro Pro Met Met Pro
                100                 105                 110

Gly Met Glu Ser Ser Pro Ser Pro Gly Pro Met Pro Pro Ala Met Ala
            115                 120                 125

Ser Pro Asp Ser Gly Ala Phe Asn Val Arg Asn Asp Val Val Ala Ile
    130                 135                 140

Ser Phe Leu Val Ala Ala His Leu Leu Leu Val
145                 150                 155
```

```
<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4
```

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
                20                  25                  30

Pro Ser Thr Met Ser Met Pro Pro Thr Thr Ser Thr Thr Thr Pro Pro
            35                  40                  45

Pro Met Ser Ser Met Ser Pro Pro Ser Ala Met Ser Pro Thr Pro
50                  55                  60

Ser Thr Met Ser Pro Pro Pro Met Ser Pro Met Thr Pro Ser Met Ser
65                  70                  75                  80

Pro Met Gly Pro Met Thr Pro Thr Met Ser Met Asp Ser Pro Pro
                85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
        115                 120                 125

Ser Gly Phe Val His Gly Ile Ser Ile Ser Met Ala Met Val Ala Ile
130                 135                 140

Ile Gly Ser Val Ala Leu Phe Phe
145                 150

```
<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 5
```

Met Ala Val Ser Arg Tyr Ile Ile Leu Leu Leu Ser Phe Thr Tyr Leu
1               5                   10                  15

Ala Ala Phe Ser Thr Ala Gln Ala Pro Ser Met Ser Pro Met Met Met
                20                  25                  30

Pro Met Ala Pro Pro Pro Ser Thr Met Pro Met Thr Pro Pro Pro Ser
            35                  40                  45

Thr Met Pro Met Thr Pro Pro Pro Thr Pro Met Thr Met Thr Pro Pro
        50                  55                  60

Pro Met Met Met Pro Met Thr Pro Pro Met Pro Met Gly Thr Pro
65                  70                  75                  80

Pro Met Thr Met Pro Met Gly Pro Pro Pro Met Met Met Pro Met Ser
                85                  90                  95

Pro Gly Pro Ser Met Met Pro Ala Ser Pro Pro Ser Pro Met Gly Pro
            100                 105                 110

-continued

```
Ser Met Ala Pro Glu Pro Ala Thr Met Ser Pro Gly Pro Ser Met Thr
            115                 120                 125

Pro Ala Glu Thr Pro Ala Ser Gly Ala Ile Met Gln Tyr Ser Ser Ile
        130                 135                 140

Thr Met Leu Gly Ile Val
145                 150

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6
aaaagatcta caaaacagag agttgtatac tttaaatcat ttagaggttg tgaaatatta      60
tggagagtga aggaaagatt gtgttcacag aagagcaaga ggctcttgta gtgaagtctt     120
ggagtgtcat gaagaaaaac tcagctgaat taggtctcaa actcttcatc aagatctttg     180
agattgcacc aacaacgaag aagatgttct ctttcttgag agactcacca attcctgctg     240
agcaaaatcc aaagctcaag cctcacgcaa tgtctgtttt tgtcatgtac aactgaggaa     300
aacagggaaa gttacggtga gggagactac tttgaagaga cttggagcca gccattctaa     360
atacggtgtc gttgacgaac actttgaggt ggccaagtat gcattgttgg agacgataaa     420
ggaggcagtg ccggagatgt ggtcaccgga gatgaaggtg gcttggggtc aggcttatga     480
tcaccttgtt gctgccatta aagctgaaat gaatctttcc aactaaaaaa tcatatacta     540
ttatatagtt gtaaacttgt aataaatatt tcattttgaa ttgttc                    586

<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75
```

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8

```
atggagagtg aaggaaagat tgtgttcaca gaagagcaag aggctcttgt agtgaagtct    60
tggagtgtca tgaagaaaaa ctcagctgaa ttaggtctca aactcttcat caagatcttt   120
gagattgcac caacaacgaa gaagatgttc tctttcttga gagactcacc aattcctgct   180
gagcaaaatc caaagctcaa gcctcacgca atgtctgttt ttgtcatgtg ttgtgaatca   240
gcagtacaac tgaggaaaac agggaaagtt acggtgaggg agactacttt gaagagactt   300
ggagccagcc attctaaata cggtgtcgtt gacgaacact tgaggtggc caagtatgca   360 ttgttggaga cgataaagga ggcagtgccg gagatgtggt caccggagat gaaggtggct   420
tggggtcagg cttatgatca ccttgttgct gccattaaag ctgaaatgaa tctttccaac   480
taa                                                                 483
```

<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 9

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125
```

Val Pro Glu Met Trp Ser Pro Glu Met Lys Val Ala Trp Gly Gln Ala
        130                 135                 140

Tyr Asp His Leu Val Ala Ala Ile Lys Ala Glu Met Asn Leu Ser Asn
145                 150                 155                 160

<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 10

Met Glu Ser Glu Gly Lys Ile Val Phe Thr Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Ala Gln Leu Arg Lys Thr Gly Lys Val Thr Val Lys Glu Thr Thr
                85                  90                  95

Leu Lys Arg Leu Gly Ala Asn His Ser Lys Tyr Gly Val Val Asp Glu
            100                 105                 110

His Phe Glu Val Thr Lys Tyr Ala Leu Leu Glu Thr Ile Lys Glu Ala
        115                 120                 125

Val Pro Glu Met Trp Ser Pro Glu Met Lys Ser Ala Trp Gly Gln Ala
    130                 135                 140

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

```
<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
    130                 135                 140

Leu Val Ala Ala Ile Lys Ser Glu Met Lys Pro Pro Leu Asn
145                 150                 155

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly Leu
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140
```

Tyr Asp Arg Leu Val Ala Ala Ile Lys Ile Glu Met Lys Ala Cys Ser
145                 150                 155                 160

Gln Ala Ala

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
                20                  25                  30

Leu Lys Phe Phe Leu Lys Ile Phe Glu Ile Ala Pro Ser Ala Gln Lys
            35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met Thr Cys Glu Ala Ala Val Gln Leu Arg
65                  70                  75                  80

Lys Ala Gly Lys Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

```
Ser Val Glu Met Lys Asn Ala Trp Gly Glu Ala Tyr Asp Gln Leu Val
        130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

```
<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
                20                  25                  30

Gly Leu Arg Phe Phe Leu Lys Ile Phe Glu Ile Ala Pro Ser Ala Arg
            35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
                20                  25                  30

Lys Lys Asp Ser Ala Asn Ile Gly Leu Arg Phe Phe Leu Lys Ile Phe
            35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
        115                 120                 125
```

```
Leu Leu Glu Thr Ile Lys Glu Ala Val Pro Val Asp Met Trp Ser Pro
    130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19
gctcattagg gtttctcatc tacgacggcg tggtgttcct ccttcctgct ctgaaaaatg      60
gcgaagagaa cgaagaaggt tggaatcgtc ggcaaatacg gaacacgtta tggtgcgagt     120
atcaggaagc agattaagaa gatggaggtc agccagcaca gcaagtactt ctgtgagttc     180
tgtggcaagt acggagtgaa agcaaaggct gttggtatct ggggttgcaa ggattgtggc     240
aaggtcaagg caggtggtgc ttacacaatg aacaccgcca gtgcggtcac tgttagaagc     300
acgatcagaa ggttgaggga gcagatcgag ggttaaaagt ctgctggctt tttatatttg     360
gtttccttgt tttgacaatt taagttttgc atcaacagtg agaacatgtt ttgatt        416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Tyr Gly Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90
```

```
<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 21

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
             20                  25                  30

Gln His Ser Lys Phe Phe Cys Glu Phe Cys Gly Lys Phe Ala Val Lys
         35                  40                  45

Arg Lys Ala Val Gly Ile Trp Gly Cys Lys Asp Cys Gly Lys Val Lys
     50                  55                  60

Ala Gly Gly Ala Tyr Thr Leu Asn Thr Pro Ser Ala Val Thr Val Arg
 65                  70                  75                  80

Ser Thr Ile Arg Arg Leu Arg Glu Gln Thr Glu Gly
                 85                  90

<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
             20                  25                  30

Gln His Ser Lys Tyr Phe Cys Glu Phe Cys Gly Lys Tyr Ala Val Lys
         35                  40                  45

Arg Lys Ala Val Gly Ile Trp Gly Cys Lys Ala Cys Gly Lys Val Lys
     50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90
```

```
<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Xaa Gly Val Lys
        35                  40                  45

Xaa Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
            85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Asn Lys Tyr Phe Cys Glu Phe Cys Gly Lys Tyr Ser Val Lys
        35                  40                  45

Arg Lys Val Val Gly Ile Trp Gly Cys Lys Asp Cys Gly Lys Val Lys
    50                  55                  60
```

```
Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ser
                 85                  90
```

```
<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 25

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Phe Phe Cys Glu Phe Cys Gly Lys Tyr Ala Val Lys
             35                  40                  45

Arg Lys Ala Val Gly Ile Trp Gly Cys Lys Asp Cys Gly Lys Val Lys
 50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Gly
                 85                  90
```

```
<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 26

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
 50                  55                  60
```

```
Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 27
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Lys Phe Phe Cys Glu Phe Cys Gly Lys Tyr Ala Val Lys
             35                  40                  45

Arg Lys Ala Val Gly Ile Trp Gly Cys Lys Asp Cys Gly Lys Val Lys
 50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90

<210> SEQ ID NO 28
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
 50                  55                  60
```

```
Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
 50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 30
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 30

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
 50                  55                  60
```

```
Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 31

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
 50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                20                  25                  30

Gln His Ser Glu Tyr Phe Cys Glu Phe Cys Gly Lys Tyr Ala Val Lys
            35                  40                  45

Arg Lys Ala Val Gly Ile Trp Gly Cys Lys Asp Cys Gly Lys Val Lys
 50                  55                  60
```

```
Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90
```

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34

<400> SEQUENCE: 33

```
attccccatc gcacagaccc gcctaagaat ccgagagaga agaagagata atgcagatct    60
tcgtcaaaac cctcaccggc aaaactataa ccctagaggt tgagagcagc gacaccatcg   120
acaatgttaa agccaaaatc caggacaaat agggcatacc acctgatcaa cagaggctga   180
tttttgctgg taagcaattg gaagatggcc ggaccttagc tgactacaac atccagaaag   240
agtctactct tcatcttgtc ctcaggctca gaggtggaac catgatcaag gtgaagacac   300
tcactggaaa agaaatcgag attgatatcg aaccaaccga cactattgat cggatcaaag   360
aacgtgttga agagaaagaa ggcatccctc ctgttcaaca aaggctcatc tatgccggaa   420
aacagcttgc tgatgacaaa acggccaaag attatgcgat agagggaggc tctgttcttc   480
atttggttct tgctcttagg ggtggtcttc tctgatctga ataaataagc ttttcaacaa   540
acatctttcc cctcactatt gtcctccttt tgtggaattc atgacacaca aaaattgcta   600
tgggaaattg gaatattatg atgttttttc tc                                 632
```

<210> SEQ ID NO 34
<211> LENGTH: 154
<212> TYPE: PRT
<213> ORGANISM: Arabidopsis thaliana
    220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 34

```
Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ala Asp Tyr Asn Ile Gln Lys Glu
         50                  55                  60
```

```
Ser Thr Leu His Leu Val Leu Arg Leu Arg Gly Gly Thr Met Ile Lys
 65                  70                  75                  80

Val Lys Thr Leu Thr Gly Lys Glu Ile Glu Ile Asp Ile Glu Pro Thr
                 85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150
```

<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Thr Met Ile Lys
 65                 70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150
```

<210> SEQ ID NO 36
<211> LENGTH: 154
<212> TYPE: PRT
<213> ORGANISM: Glycine max -continued

```
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
    130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40
```

<400> SEQUENCE: 37

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145
```

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
    given in SEQ ID NO: 40

<400> SEQUENCE: 38

```
Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95
```

-continued

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
145                 150

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180
tttttgctgg taagcaattg gaagatggcc ggaccttagc tgattacaac atccagaaag     240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agagggaggc tctgttcttc     480
atttggttct tgctcttagg ggtggtcttc tctgatctta ataaataagc ttttcaacaa     540
acatcttttc cctcactatt gtcctcctta tgtggaattc atgacacacc aaaattgcta     600
tgggaaattg gaatattatg                                                  620

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
     Pfam Description: Ubiquitin family

<400> SEQUENCE: 40

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41

| | | | | | |
|---|---|---|---|---|---|
| atattttgt | gtagatgaag | atcaacaaga | gaaggtgttg | ttgtgagttg | tgttgttatg | 60 |
| gtaccttcct | tcaaccacaa | aacctctctc | cctctaccac | ccattctctt | ctctctctct | 120 |
| ctctcccgtc | ctccatctct | caccttctca | atctcttcac | caccaccatc | atcatcatta | 180 |
| tcttctccaa | tctctataac | ctcgaaatcc | ctcaaaacct | ctccctcaaa | ccaaatgaaa | 240 |
| tgacccctttt | gtgagaacat | tttttccccc | ttaagaaaag | gtcaaaggct | gcaacttttt | 300 |
| cttaaccaat | ctcacatttt | tttatttttc | aacgtatttt | ggccaggttt | ggttttctgg | 360 |
| gttgtcttgg | aattcaaaaa | agattccaac | tttgaagatg | ggtaggggtg | gaaccgccgc | 420 |
| ggcggcggcg | gaggtcgccg | aacccggttt | aaggccggtt | tatttcaaag | aacagcgata | 480 |
| tagggcgtc | agaaaaagac | cgtggggccg | gttcgctgcc | gaaatcagag | accctttgaa | 540 |
| gaaagccagg | gtttggctcg | gaacctttga | caccgccgag | gaggcggcgc | gtgcctacga | 600 |
| cacggcggcg | agaaccctcc | ggggaccaaa | ggcgaagacc | aatttccctc | tttctccgcc | 660 |
| gttctaccat | cccgatccat | tttccgatca | ccggcacttc | gccaacaccg | gcgaagattt | 720 |
| ccacgatcac | cggcgaccaa | catccagtgg | catgagcagc | accgtagagt | ccttcagcgg | 780 |
| cccccgtgct | gccgtgccgg | cgacagcgcc | ggtggccacc | ggccggagat | atccccggac | 840 |
| gccaccgtt | atccccgagg | actgccgcag | cgactgcgat | tcgtcgtcct | ccgtcgttga | 900 |
| cgacggcgaa | ggcgacaacg | tggcgtcgtc | gttcccgcga | gaaccgttgc | cgtttgatct | 960 |
| aaacgcgttg | ccgttagacg | atgctgacgt | ggcaaccgat | gatctgttct | gcaccgttct | 1020 |
| ttgcctctga | tgagaaaaaa | tgaaaaaacg | gaacgaaatg | atgtatttgg | ttcgttgacg | 1080 |
| gaattattat | tatttttttc | tttctt | | | | 1106 |

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<222> LOCATION: (26)..(89)
<223> OTHER INFORMATION: Pfam Name: AP2;
      Pfam Description: AP2 domain

<400> SEQUENCE: 42

```
Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
            20                  25                  30

Lys Arg Pro Trp Gly Arg Phe Ala Ala Glu Ile Arg Asp Pro Leu Lys
        35                  40                  45

Lys Ala Arg Val Trp Leu Gly Thr Phe Asp Thr Ala Glu Glu Ala Ala
50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe His Asp His Arg
            100                 105                 110

Arg Pro Thr Ser Ser Gly Met Ser Ser Thr Val Glu Ser Phe Ser Gly
        115                 120                 125

Pro Arg Ala Ala Val Pro Ala Thr Ala Pro Val Ala Thr Gly Arg Arg
130                 135                 140

Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
        195                 200                 205

Cys Leu
    210
```

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
    Pfam Description: AP2 domain
<220> FEATURE:
<221> NAME/KEY: misc_feature
<223> OTHER INFORMATION: Functional homolog of Ceres Clone ID no. 674166
    given in SEQ ID NO: 42

<400> SEQUENCE: 43

```
Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
50                  55                  60

Arg Ala Tyr Asp Ser Ala Ala Arg Asn Leu Arg Gly Pro Lys Ala Lys
65                  70                  75                  80
```

```
Thr Asn Phe Pro Ile Asp Ser Ser Pro Pro Pro Asn Leu Arg
             85                  90                  95

Phe Asn Gln Ile Arg Asn Gln Asn Gln Val Asp Pro Phe Met
            100                 105                 110

Asp His Arg Leu Phe Thr Asp His Gln Gln Gln Phe Pro Ile Val Asn
            115                 120                 125

Arg Pro Thr Ser Ser Ser Met Ser Ser Thr Val Glu Ser Phe Ser Gly
130             135                 140

Pro Arg Pro Thr Thr Met Lys Pro Ala Thr Thr Lys Arg Tyr Pro Arg
145             150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225

<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ser Arg Val Trp
        35                  40                  45
```

```
Leu Gly Thr Phe Asp Ser Ala Glu Glu Ala Ala Arg Ala Tyr Asp Ala
     50                  55                  60

Ala Ala Arg Asn Leu Arg Gly Pro Lys Ala Lys Thr Asn Phe Gln Ile
 65                  70                  75                  80

Asp Cys Ser Pro Ser Pro Leu Gln Pro Leu His His Arg Asn Gln
                 85                  90                  95

Ile Asp Pro Phe Met Asp His Arg Leu Tyr Gly Gly Glu Gln Glu Val
                100                 105                 110

Val Ile Ile Ser Arg Pro Ala Ser Ser Met Ser Ser Thr Val Lys
            115                 120                 125

Ser Cys Ser Gly Val Arg Pro Ala Ser Ser Val Ala Lys Ala Ala
130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Xaa
        195                 200                 205

Xaa Cys Thr Asp Leu Xaa Leu
210                 215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Asp Ala Asp Gly Asp Val Glu
 1               5                  10                  15

Leu Arg Phe Arg Gly Val Arg Lys Arg Pro Trp Gly Arg Tyr Ala Ala
                 20                  25                  30

Glu Ile Arg Asp Pro Ala Lys Lys Ala Arg Val Trp Leu Gly Thr Phe
             35                  40                  45

Asp Ser Ala Glu Asp Ala Arg Ala Tyr Asp Ala Ala Ala Arg Met
 50                  55                  60

Leu Arg Gly Pro Lys Ala Arg Thr Asn Phe Pro Leu Pro Ala Ala Ala
 65                  70                  75                  80

Ala Leu His His Pro His Met Pro Ala Ala Ala Ala Ala Pro
             85                  90                  95

Pro Tyr Thr Thr Tyr Pro Thr Ala Thr Gly Val Val Ser Thr Pro Pro
                100                 105                 110

Val Ala Arg Pro Ala Cys Ser Ser Leu Ser Ser Thr Val Glu Ser Phe
            115                 120                 125

Ser Gly Ala Arg Pro Arg Pro Val Leu Pro Pro Arg Phe Pro Pro Pro
130                 135                 140
```

```
Ser Ile Pro Asp Gly Asp Cys Arg Ser Asp Cys Gly Ser Ser Ala Ser
145                 150                 155                 160

Val Val Asp Asp Cys Thr Asp Ala Ala Ser Ala Ser Cys Pro
            165                 170                 175

Phe Pro Leu Pro Phe Asp Leu Asn Leu Pro Pro Gly Gly Gly Ala
            180                 185                 190

Gly Val Gly Phe Tyr Ala Asp Glu Glu Asp Glu Leu Arg Leu Thr Ala
        195                 200                 205

Leu Arg Leu
    210
```

```
<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65                  70                  75                  80

Ser Ala Thr Gln Pro Pro Pro Arg Pro Pro Pro Ala Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Arg Ser Ala Ala Arg Ala Gly
        115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Gln Glu Gly Ala
            165                 170                 175

Leu Asp Ala Glu Ala Asp Gln Met Thr Cys Arg Tyr Asp Thr Leu Leu
        180                 185                 190

Arg Leu
```

```
<210> SEQ ID NO 47
<211> LENGTH: 660
<212> TYPE: DNA
<213> ORGANISM: Populus balsamifera subsp. trichocarpa
```

<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47

```
atggggagaa caagaacaac aacaaaacag gctgttgacc caaatggatc tgcaacccaa    60
aatatgttag taattgcaaa agagcccaga tacagaggag tacgaaagag accatgggga   120
agattcgctg cggagattag agatccctgg aaaaagacca gagtttggct gggcaccttc   180
gactctgcag aggatgcagc gcgtgcctac gatgcggctg ctcgcaccct ccgcggagca   240
aaggccaaga caaactttcc tatctccaca acgaaccagt tattcaatca tcaaaatcaa   300
aaccaaagcc caaccgatcc cttcttggat caccacagta taaatcccca aagacccaca   360
tctagcagtt tgagcagtac agtggagtct ttcagcggtc ctaggcctcc gcagccaaca   420
acaacaacaa aatcgggaaa tgggccgagg agatctcatc cacggatccc accggttgtt   480
ccagaagatt gtcatagcga ttgcgattca tcttcttcgg tggttgatga cagagatgtc   540
gcatccgctg cttcttcttt gtgccgcaag cctttgcctt tcgatctaaa tttcccaccg   600
ttggaccagg ttgacttggg ctctggtgat gatctccact gcactgcttt atgcctttga   660
```

<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 48

```
Met Gly Arg Thr Arg Thr Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Pro Gln Pro Thr Thr Thr Thr Lys
    130                 135                 140
```

```
Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
            165                 170                 175

Asp Arg Asp Val Ala Ser Ala Ala Ser Ser Leu Cys Arg Lys Pro Leu
        180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
        210                 215
```

<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49

```
attattcctc ttccatctct attctccata cacccacca caccacttgt gaaaaacctc      60
attaatatca cacactgaca tgtatctctg agctccaatc caatacaaga ccacaccttg    120
tcgtgtcgga cgaaccttgg tgtctgtttt tttttttttt tcattatttt ctccgaagag    180
atgaggaagg gcagaggtgg aggcgcctcg gcggcggcgg tggatgtgaa cggatccatt    240
ttaaaggagc tcggtaccg gggcgtgagg aagagaccgt gggggagatt cgccgcggag    300
atcagagacc cgttgaagaa agccaggggtt tggttgggaa ccttcgattc tgccgaggat    360
gctgctcgtg cctacgacgc cgccgctcgg actctccgag gtcccaaggc caaaacaaat    420
ttcccccctc tctcaccttt tgctatcca caccccacca ccgatcctt cttctacact    480
ggtttccacg atcaacacca ccaccacaac aacaacaacc ttaacaaccc tcaaagaccc    540
acttcaagtg gcatgagtag caccgttgag tccttcagtg ggccccgcc tcccaccacc    600
accactacca ccacaaccac aactgcgacg ccgttttga ctgctacgcg gagatacccg    660
cgcactcccc ctcttgtccc tgaagactgc cacagtgact gcgactcttc ctcctccgtc    720
gttgacgacg gcgacgacaa catcgtttcg tcgtcgtttc gacctccctt gccgtttgat    780
ctcaacgcgc tgccgtttga tgatgctgcc gcggatgatg atctacgccg caccgcgctt    840
tgtctctgat gatgattatc gtgcgatgat gatttttaat ttctcatttt tttacttgat    900
tttttgtta ttgctatgca gaagaaatat atattaaaaa tgatgatcag atgtaagatt    960
atggtaatat gatcttaatt ctgtg                                          985
```

<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain

```
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 50

Met Arg Lys Gly Arg Gly Gly Ala Ser Ala Ala Val Asp Val
1               5                   10                  15

Asn Gly Ser Ile Leu Lys Glu Pro Arg Tyr Arg Gly Val Arg Lys Arg
                20                  25                  30

Pro Trp Gly Arg Phe Ala Ala Glu Ile Arg Asp Pro Leu Lys Lys Ala
            35                  40                  45

Arg Val Trp Leu Gly Thr Phe Asp Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
                100                 105                 110

Asn Leu Asn Asn Pro Gln Arg Pro Thr Ser Ser Gly Met Ser Ser Thr
            115                 120                 125

Val Glu Ser Phe Ser Gly Pro Arg Pro Pro Thr Thr Thr Thr Thr Thr
130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                165                 170                 175

Ser Ser Ser Val Val Asp Asp Gly Asp Asp Asn Ile Val Ser Ser Ser
            180                 185                 190

Phe Arg Pro Pro Leu Pro Phe Asp Leu Asn Ala Leu Pro Phe Asp Asp
        195                 200                 205

Ala Ala Ala Asp Asp Asp Leu Arg Arg Thr Ala Leu Cys Leu
            210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51 actttctct cccattcttt tacaactcac gttgcacagc cttttctct atatattact    60 tgacataaac tactattcac aacacaaaca cacacataac catggcctct tcttcacaag   120
ctttcctttt gctcacattg tctatggttt tagttcattt ctctttagct caatctccca   180
tgatggctcc ttctggctcc atgtccatgc cgccaatgcc tagcggcggc tctccaatgc   240
caatgatgac tccaccacct atgccaatga tgactccacc acctatggct atggctccac   300
cacctatgcc tatgactcca ccaccaatgc ccatggctcc gatgccaatg actccatctt   360
caagtccaat gagcccacca actactatgg ccccaagtcc agaaacagtc cctgatatgg   420
cttcgccacc gatgatgcca ggaatggatt cttctccttc tccgggaccc atgccaccgg   480
```

```
caatggcctc tccagattcc ggagcattca atgtaagaaa cgacgtcgta gcaatttcgt    540
tccttgttgc agctcatttg ctcctagttt gagattatta ttaaattggc cagcgtcgtg    600
tttgtgtaat ttactttcat ttttttctcg agccattaat tttcatgttt tatcatatat    660
ttgggtttgt gtttgatatg gtacgattca gacatttgtt tgcttaataa gtttatcgtt    720
gactct                                                                726
```

<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

```
Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
            20                  25                  30

Ser Met Ser Met Pro Pro Met Pro Ser Gly Gly Ser Pro Met Pro Met
        35                  40                  45

Met Thr Pro Pro Pro Met Pro Met Met Thr Pro Pro Pro Met Ala Met
    50                  55                  60

Ala Pro Pro Pro Met Pro Met Thr Pro Pro Pro Met Pro Met Ala Pro
65                  70                  75                  80

Met Pro Met Thr Pro Ser Ser Ser Pro Met Ser Pro Pro Thr Thr Met
                85                  90                  95

Ala Pro Ser Pro Glu Thr Val Pro Asp Met Ala Ser Pro Pro Met Met
            100                 105                 110

Pro Gly Met Asp Ser Ser Pro Ser Pro Gly Pro Met Pro Pro Ala Met
        115                 120                 125

Ala Ser Pro Asp Ser Gly Ala Phe Asn Val Arg Asn Asp Val Val Ala
    130                 135                 140

Ile Ser Phe Leu Val Ala Ala His Leu Leu Leu Val
145                 150                 155
```

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53

```
gcagaagcac aaggtaagat tgaaggagga gaccggaact cttcttcgcc aaaaccctag     60
ttcgagctca ccaacaacaa tctttcgcaa tgactaagcg taccaagaag gccggaattg    120
tgggtaaata tggtaccaga tatggagctt cattaaggaa acagattaag aagatggaag    180
tgagtcagca tgcaaagtac ttctgtgagt tctgcggaaa gtacgctgtg aagagacagg    240
ctgttggaat ctggggatgc aaggattgtg gcaaagttaa agctggtggt gcttacactt    300
```

-continued

```
tgaacaccgc cagtgccgtg acagttagaa gcaccattag aaggttgagg gagcaaactg      360
aatcttagat tgatctcgtt atctatattt tgtattttgg tactgggtga gaggtaccat      420
cagagctaat ttagtgttta tcaccttttc tggtcttcaa gaactagtta gtcattttgt      480
tattcagaga tttttgataa tgtctagtat cttacatttg tgagcagact atttctttgt      540
ttcaaattat ggagttctga tgaatcttat atttattctc                            580
```

<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 54

```
Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
            85                  90
```

<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55

```
accagaccac accacaccac accgcgtcca catcctcccg cgcttctccg ctcagcccgc       60
gcgtttccgc tgaggaggga tagccgcgcg gcgcgtcgag gggtttgtct ttgatcgggt      120
agctgaggct gagcgggcgg ggcaggatga tgcgcgacac ggcggccgtg gccgtggcgg      180
cgccgcggta caggggcgtg cggaagcggc cgtgggccg gttcgcggcg gagatccgcg      240
acccggcgaa gcgcgcgcgc gtctggctcg gcaccttcga ctccgccgag gccgcggcgc      300
gcgcctacga cgtcgccgcg cggaccctgc gcggcccgct cgccaggacc aacttcccct      360
gcgcctcctc ccgcctcccg ctgccctccc gccaccaagg cggctgtggc ggcggcctcg      420 tcgccgcc gccgccgcg ccgacgtgca gctccagctc caccgtcgag tcctccagcg      480
gaccccgagg ggcgcccagg gctgctgcgg cggcggcgcc tcgaattcgg aggcggtcgg      540
```

-continued

```
tgaaaaagcc gcggccggca gcgcccgaca tcgactgcca cagcgactgc gcctcgtcgg    600
cctccgtcgt ggacgacggc gacgacgcct ccacggtccg gtcgcgcgcg ccgttcgacc    660
tcaacgtccc ggctccggtg gacggtgacc acgccctcga cctctgcacg gagctgcggc    720
tctgagcaat atgatcctcg aacaacaaca acagcaaaac attgaaggcg attttccccc    780
ggtcttcttt tcctgactaa attctgatat gatcaatatg ctcgagagtt ctcgttttct    840
ttaacgcctc ttgtatttgg atctgctacc atcttctctg cccattctat ttgtacacca    900
gataacatgt aagatgttca cgaattaaca catatctttt cttaaaaaaa tgaattaaca    960
cggaaaaaaa aaaaaaaaaa aaa                                           983
```

```
<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Gly Leu Val Ala Pro Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
        115                 120                 125

Arg Arg Ser Val Lys Lys Pro Arg Pro Ala Ala Pro Asp Ile Asp Cys
    130                 135                 140

His Ser Asp Cys Ala Ser Ser Ala Ser Val Val Asp Asp Gly Asp Asp
145                 150                 155                 160

Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190

<210> SEQ ID NO 57
<211> LENGTH: 594
<212> TYPE: DNA
<213> ORGANISM: Panicum virgatum
```

```
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57
gagccctacc cgcacccgcg ccgccgccgc cccgcgcccc gtcgccgcag acgactccgc      60
cccgtcgccg cgatgacgaa gcgcaccaag aaggccggaa tcgtcggcaa atatggaact     120
aggtatggtg ctagcttgcg taagcaaatc aagaagatgg aggtgtctca gcactccaag    180
tacttctgcg agttctgtgg aaagtttgct gtgaaaagga agcagttgg aatctgggga     240 tgcaaggact gcgggaaggt taaggctggt ggtgcttaca ccatgaacac tgctagtgca    300
gtcaccgtca ggagcacaat ccgtcgcttg agggagcaga ctgaagcata atcggagctc    360
ttctctgcag tagtcctgtg cttttttgtac cgtctaagac atatggctgt ttggcctaag    420
aacattcatg aatattctgg ttatgcttaa ggatatcaaa aattatggtg ctaaaatttg     480
tacttcgttg ctgttgcaaa gttgacctgt cttgatccat tcataatgta gaatttcctc    540
atggttctta tctccagttt gctactcttt ggccaaaaaa aaaaaaaaaa aaaa           594

<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
       Pfam Description: Ribosomal L37ae protein family
<220> FEATURE:
<221> NAME/KEY: misc_feature
<223> OTHER INFORMATION: Functional Homolog of Ceres CLONE ID no. 271922
       Given in SEQ ID NO: 20

<400> SEQUENCE: 58

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60
```

<400> SEQUENCE: 59

```
acacagatac attcgtcgat ccaccactgt ccagtgcttg gcggttacgc acgcacgcac    60
acagatagga ttatctttta ctacaccaac tcaccaagat actagcaagc cgaatcgaca   120
aacaagcagc aggaagagga ggcatggcgc tcgcggaggg gaacgtcatc ttcggcgagg   180
agcaggaggc gctggtgctc aagtcgtggg ccctcatgaa gaaggactcg gccgacctcg   240
gcctccgctt cttcctcaag atcttcgaga tcgcgccgtc ggcgaagcag atgttctcgt   300
tcctgcgcga ctccgacgtg ccgctcgaga gaaccccaa gctcaagaac cacgccatgt   360
ccgtcttcgt catgacctgc gaggcggcgg cgcagctacg gaaggccggg aaggtcaccg   420
tcagggagac gacgctcaag cggctgggcg ccacgcactt caagtacggc gtcgccgacg   480
gccacttcga ggtgacgagg ttcgcgctgc tggagacgat aaaggaggcg cttcccgccg   540
acatgtggag cctggagatg aagaacgcct ggagcgaggc ttacaaccag ctggtggcgg   600
ccatcaagca ggagatgaag cctgccgcat gatgctgctg ctgctactga gatgaagcct   660
gcccgcatga tgctgctgct gctactcggc ctccgcgctg agttccccct acgatgcacc   720
accatctcca aattcttcat cgctgttttt tttttttgc tgttttgact tgtattgtgc   780
attttccaaa tctctcgatg gagacaagtg tgatgactaa tttttgagag catgtatata   840
tgttgtgatg agcattgaat aaaaaaaaaa aaaaaaaaa                          880
```

<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 60

```
Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
    130                 135                 140
```

```
Glu Ala Tyr Asn Gln Leu Val Ala Ala Ile Lys Gln Glu Met Lys Pro
145                 150                 155                 160

Ala Ala

<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61
cctgcccatt tccatcttcc ttctttcctt cctctttcct ttgtcttctt gctttatctt      60 cccttatct  tcaatctttt ctgttctgtt ttttcttag  attcataggt aagttcgttt     120
tggttggctt gattatttcc tcacttccct tctttttgg  ttcatcgtga tcttttcatc     180
aacccctttt gattgttata tagattgtta ctattctttt aatcttttaa atattttttt     240
tccatgagga gagggagagg tgccgcagct gcaaacgccg tagctaggag accggcactg     300
caacccagcg gatctattaa agagccgaga tacagaggtg ttagaaaaag gccatggggc     360
agattcgcgg ccgagattcg agacccttgg aagaagacca gggtctggtt agggacgttc     420
gactcggccg aagaagccgc tcgagcctac gatacggcgg cgaggacgct ccgtggaccc     480
aaagctaaaa caaatttccc cataaattct tcaaatatcc cggcttttcc tttcgaaacc     540
aatcatcacc acaacgaagg gttcatcgac caacgccggt tatatccgat gggcgaattt     600
catgaccccg aagtgaatcc acagagaccc acgaggagta gcatgagtag cacggtggag     660
tcgtttagtg gacccagacc ggcccaacca ccgcaaaagt cggcggactt cgcggtggtt     720
tcgactagga agtactatcc gaggccgccg ccagtagagc cagaggattg tcatagtgac     780
tgtgattcat catcgtcggt ggttgatgat ggggatatcg cgttgtcttc ttgtcggaaa     840
actttgcctt tcgatctcaa ttttccaccc ttggatgaag atggaagatc tccagtgtac     900
tgctttatgt ctttgatcgc gatgccggtg atgaatgatg atgatcgatt attggatctc     960
tttttctttt ttaaaaaatg ttagcttttt taagcggaaa aaaaaaaaaa aaaaaaa      1017

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 62

Met Arg Arg Gly Arg Gly Ala Ala Ala Ala Asn Ala Val Ala Arg Arg
1               5                   10                  15

Pro Ala Leu Gln Pro Ser Gly Ser Ile Lys Glu Pro Arg Tyr Arg Gly
            20                  25                  30
```

| | | | | | | | | | | | | |
|---|---|---|---|---|---|---|---|---|---|---|---|---|
|Val|Arg|Lys|Arg|Pro|Trp|Gly|Arg|Phe|Ala|Ala|Glu|Ile|Arg|Asp|Pro|
| | |35| | | |40| | | |45| | | | | |

Val Arg Lys Arg Pro Trp Gly Arg Phe Ala Ala Glu Ile Arg Asp Pro
           35            40            45

Trp Lys Lys Thr Arg Val Trp Leu Gly Thr Phe Asp Ser Ala Glu Glu
 50                 55                60

Ala Ala Arg Ala Tyr Asp Thr Ala Ala Arg Thr Leu Arg Gly Pro Lys
65               70               75               80

Ala Lys Thr Asn Phe Pro Ile Asn Ser Ser Asn Ile Pro Ala Phe Pro
           85            90            95

Phe Glu Thr Asn His His His Asn Glu Gly Phe Ile Asp Gln Arg Arg
          100           105           110

Leu Tyr Pro Met Gly Glu Phe His Asp Pro Glu Val Asn Pro Gln Arg
      115           120           125

Pro Thr Arg Ser Ser Met Ser Ser Thr Val Glu Ser Phe Ser Gly Pro
130              135               140

Arg Pro Ala Gln Pro Gln Lys Ser Ala Asp Phe Ala Val Val Ser
145           150            155          160

Thr Arg Lys Tyr Tyr Pro Arg Pro Pro Val Glu Pro Glu Asp Cys
          165           170           175

His Ser Asp Cys Asp Ser Ser Ser Val Val Asp Asp Gly Asp Ile
        180           185             190

Ala Leu Ser Ser Cys Arg Lys Thr Leu Pro Phe Asp Leu Asn Phe Pro
      195           200           205

Pro Leu Asp Glu Asp Gly Arg Ser Pro Val Tyr Cys Phe Met Ser Leu
      210           215           220

Ile Ala Met Pro Val Met Asn Asp Asp Asp Arg Leu Leu Asp Leu Phe
225              230           235          240

Phe Phe Phe Lys Lys Cys
          245

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63

```
acacagatac attcgtcgat ccaccactgt ccagtgcttg gcggttacgc acgcacgcac    60
acagatagga ttatctttta ctacaccaac tcaccaagat actagcaagc cgaatcgaca   120
aacaagcagc aggaagagga ggcatggcgc tcgcggaggg gaacgtcatc ttcggcgagg   180
agcaggaggc gctggtgctc aagtcgtggg ccctcatgaa gaaggactcg gccgacctcg   240
gcctccgctt cttcctcaag atcttcgaga tcgcgccgtc ggcgaagcag atgttctcgt   300
tcctgcgcga ctccgacgtg ccgctcgaga agaaccccaa gctcaagacc acgccatgt   360
ccgtcttcgt catgacctgc gaggcggcgg cgcagctacg gaaggccggg aaggtcaccg   420
tcagggagac gacgctcaag cggctgggcg ccacgcactt caagtacggc gtcgccgacg   480
gccacttcga ggtgacgagg ttcgcgctgc tggagacgat aaaggaggcg cttcccgccg   540
acatgtggag cctggagatg aagtacgcct ggagcgaggc ttacaaccag cttgtggcgg   600
ccatcaagca ggagatgaag cctgccgcat gatgctgctg ctgctactcg gcctccgcgc   660
tgagttcccc ctacgatgca ccaccatctc caaattcttc atcgctgt                708
```

-continued

```
<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Tyr Ala Trp Ser
    130                 135                 140

Glu Ala Tyr Asn Gln Leu Val Ala Ala Ile Lys Gln Glu Met Lys Pro
145                 150                 155                 160

Ala Ala

<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65
acacagatac attcgtcgat ccaccactgt ccagtgctcg gctcggttac gcacgcacgc      60
acacaaattg tagtacctgt gttttacacc accaaagata ctagcaagcc gagtcgacaa     120
acaaagcagc aggaagaggc atggcgctcg ctgacgggaa cggcgcggcc atcttcggcg     180
aggagcagga ggcgctggtg ctcaagtcgt gggccctcat gaagaaggac tcggccgacc     240
tcggcctccg cttcttcctc aagatcttcg agatcgcgcc gtcggcgaag cagatgttct     300
cgttcctgcg cgactccgac gtgccgctgg agaagaaccc caagctcaag acccacgcca     360
tgtccgtctt cgtcatgacc tgcgaggcgg cagcgcagct acggaaggcc gggaaggtca     420
```

-continued

```
ccgtcaggga gacgacgctc aagcggctgg gcgcaacgca cttcaagtac ggcgtcgccg     480
acggccactt cgaggtgaca aggttcgcgc tgctggagac gataaaggag gcgcttcccg     540
ccgacatgtg gagcctggag atgaagaacg cctggagcga ggcttacaac cagctcgtgg     600
cggccatcaa gcaggagatg aagcctgctg catgatgctg catgctgcta catactcggc     660
ctccgagttc cccctacgat gcaccaccat ctccaagttc ttcatcgcta tt              712
```

<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Gln Glu Met
145                 150                 155                 160

Lys Pro Ala Ala

<210> SEQ ID NO 67
<211> LENGTH: 1129
<212> TYPE: DNA
<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67

```
atccgccccc atttgttcgc tctgtatatt gaactttcct ttctcgattt tctctttgaa      60
caaaaatgat gaagatcttc aaccagactc tcaccggcaa gactatcacg ctcgaggtcg     120
```

```
agagctccga caccatcgaa ggcgccaaca ccattctcca agatggaggg agcctccctc    180
cttaccgaac ccgactgatc ttcgccggac aacagcttga ggacggactg accttgtgcg    240
attacaacat cttaaaggag gtcaactctc cacctcttcc tccggttgcg cggtgggatg    300
cttaccttcc ggaggacctt gaccggcaat accatcactc tccaggtcta aagcgccgac    360
tcgatcaagt tcgttcacgc taacatccaa gactaggaag gcgtcccccc ataccaacta    420
cgactctgct tcgaccgaaa acaacttgaa gacggccgta ccttggccga ctacaacatc    480
cagaaggagt caacgctcca tcttgtcctt cgtttgcgtg gcgggatgca aatcttcgtt    540
aagacgctta cgggaaagac gatcactctc gaggtcgaga gctctgacac gatcgacaac    600
gtgaaagcca aaatccaaga caaggaaggc atcccgccag accagcaacg tctcatcttc    660
gccggaaagc aactcgagga cgggcggact ttagccgatt acaatatcca aggaatcg     720 actcttcatc tggtcctgcg tcttggaggt gggatgcaga tcttcgtcaa gactttgacc    780
ggtaagacga ttactttaga agtggagagc tcggatacga ttgataacgt gaaagcgaag    840
attcaggaca agaaggaat tccaccagat cagcaaaggt tgattttgc tgggaaacaa      900 ctggaagacg gaaggacttt ggctgattac aatattcaaa aggattccac tcttcacctt    960
gttcttcgtc ttcgtggtgg gttctaagcc ttaaggtctc ccttaatgtg ggttttctgg    1020
ttttacgtga aggactgtgc cctgtaatgg ccttttaaat aatttctagt ctttgtttac    1080
cggttgcatc tatgtatggt ttctcttaga atggaattag catatttac                1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
       Pfam Description: Ubiquitin family
<220> FEATURE:
<221> NAME/KEY: misc_feature
<222> LOCATION: (77)..(150)
<223> OTHER INFORMATION: Pfam Name: ubiquitin
       Pfam Description: Ubiquitin family
<220> FEATURE:
<221> NAME/KEY: misc_feature
<223> OTHER INFORMATION: Functional Homolog of Ceres CLONE ID no. 2403
       Given in SEQ ID NO: 40

<400> SEQUENCE: 68

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110
```

```
Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150
```

<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69

```
aaatcaaata cctactgcaa ttaaaatccc ggaattactt aaacaacaat ggctacctat      60
gaaggtaaag ttttcactga agaacaagaa gctttggtgg tcaagtcatg gactgtaatg    120
aagaagaacg cagctgaatt gggtcttaaa ttcttcttga agatatttga gattgcacca    180
tcagccaaga aactattctc attcttgaga gactccaatg ttccattgga gcaaaacaca    240
aagctgaagc cccatgccat gtctgtcttt gtcatgacat gtgaatctgc agtgcaactg    300
cgtaaagcag gcaaagttac agtgagggaa tcaaatttga agaaattagg agctacccat    360
tttaagtatg gggtagttga tgaacatttt gaggtaacaa aatttgctct tttggagacc    420
ataaaagaag cagtaccaga tatgtggtca gatgagatga agaatgcatg gggtgaagcc    480
tatgatcgtt tggtcgcagc cattaaaata gaaatgaagg catgctcaca agctgcatga    540
tttcacaagt tccctacatt attgcttgtt aattttgggt ccaataagat tgaaagtttt    600
caatcattta aacatgtaat gtaacatagc tattgctcat cactactgtt tttttcccct    660
agtttgtttg ctcctgttc                                                 679
```

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 70

```
Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60
```

```
Lys Leu Lys Pro His Ala Met Ser Val Phe Val Met Thr Cys Glu Ser
 65                 70                  75                  80

Ala Val Gln Leu Arg Lys Ala Gly Lys Val Thr Val Arg Glu Ser Asn
                 85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71
atcgccacaa gttcgcgatc tctcgatttc acaaatcgcc gagaagaccc gagcagagaa      60
gttccctccg atcgccttgc caagatgcag atctttgtga agacactcac tggcaagact     120
atcacccttg aggtggagtc ttctgacaca attgacaatg tcaaggcaaa gatccaggac     180
aaggaaggga ttcctccaga ccagcagcgc cttatcttcg ctggcaagca gcttgaggat     240
ggccgtacac ttgcagatta caacattcag aaggagtcca cactgcacct tgtcctcagg     300
ctgcgtggag gcatgcagat tttcgtgaag accctcactg caagacgat caccctggag      360 gtggagtcat ctgacaccat cgacaatgtg aaggcaaaga tccaggacaa ggagggcatc     420 cccccctgacc agcagcgcct catctttgca ggcaagcagt tggaggatgg gcgaactctg     480
gctgactaya atatccagaa agaatcmacc ctgcacctsg tsctccgcct gcgtggtgga     540
atgcagatct ttgtgaagac gcttaccggc aagaccatca ccttggaggt ggagtcttcg     600
gacaccatcg acaatgtgaa ggcgaagatt caggacaagg agggcattcc tccggaccag     660
crgcgcctca tctttgctgg caagcagcta gaggacgggc gtaccctggc ggattacaac     720
atccagaagg agtccaccct ccaccttgtc ctgcgcctcc gtggtggttt ctgagcctag     780
tgctcctgag ttgccttttg tcgttatggt caacctctgg tttaagtcgt gtgaactctc     840
tgcattgcgt tgctagtgtc tggttgtggt tgtaataaga acatgaagaa catgttgctg     900
tggatcacat gacttttttt ttttgaaccg gaagatcaca tgactttcat ggctttaagt     960
tcctgaactc tgaaatctgg acccccttttt aagctctgaa ctc                     1003

<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
```

```
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(226)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
    130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190
```

-continued

```
Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 73
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73
acacagatac actcgtcgat ccaccagacc accactgtcc agtgctcggc tcggttacgc      60
acgcacgcac acaaatagga gtacctgttt tacaccacca agatactagc aagcccaagc     120
cgagtcgaca acaagcagc aggaagaggc atggcgctcg cggaggggaa cggcgcggcc      180
atcttcggcg aggaacagga ggcgctggtg ctcaagtcgt gggccctcat gaagaaggac     240
tcggccgacc tcggcctccg cttcttcctc aagatcttcg agatcgcgcc gtcggcgaag     300
cagatgttct cgttcctgcg cgactccgac gtgccgctgg agaagaaccc caagctcaag     360
acccacgcca tgtccgtctt cgtcatgacc tgcgaggcgg cagtgcagct acggaaggcc     420
gggaaggtca ccgtcaggga gacgacgctc aagcggctgg gcgcaacgca cttcaagtac     480
ggcgtcgccg acggccactt cgaggtgaca aggttcgcgc tgctggagac gataaaggag     540
gcgcttcccg ccgacatgtg gagcctggag atgaagaacg cctggagcga ggcttacaac     600
cagctcgtgg cggccatcaa gcnnnagatg aagcctgccg catgatgctg catgctgcta     660
catactcggc ctccgagtcc ccctacgat gcaccaccat ctcccagttc ttcatcgcta      720
tttt                                                                   724

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

```
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

Met Ala Leu Ala Glu Gly Asn Gly Ala Ala Ile Phe Gly Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Val Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Xaa Xaa Met
145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg      60
ctcaccgcct tcccaccccc ccacccaccc acctgccccc ccccccccc cgccctcgcc     120 gtccgcgatg cgccgggcga agccgccgca gccgcagccg tcgccgtcgc cggagatccg     180
gtaccgcggc gtgcggaggc ggccatcggg gcgctacgcc gccgagatcc gggacccggc     240
caagaagacc ccgatctggc tcggcacctt cgactccgcc gaggccgccg cgcgcgccta     300
cgacgccgcc gccgatccc tccgcgggcc caccgcccgc accaacttcc ccagcgccgc     360
ggcccccgcg ccgcggcaca gcaggccccc cgcccctcc gccgccgcgc aggcggctgc     420
cgcggcggca gcggccacgt ccagccacag cagcaccata gagtcgtgga gcgacggcgc     480
gacccgcgcc gcgctggcgc gtagcgctgc ctccgtcctg gcgcgcagcg ccgctccgac     540
ggaggaggaa gacgaggact gccgcagcta ctgcggatcc tcgtcgtccg tcctctgcga     600
```

```
agacactggg ggcgacgatg cggccgcctc ccgcgcgccc ctgccgttcg atctgaacct      660
gccgccgcct catgacgcgg cctccgagac cgatca                               696
```

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76

```
Met Arg Arg Ala Lys Pro Pro Gln Pro Gln Pro Ser Pro Ser Pro Glu
1               5                   10                  15

Ile Arg Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Arg Ala Tyr Asp Ala Ala Ala Arg Ser
    50                  55                  60

Leu Arg Gly Pro Thr Ala Arg Thr Asn Phe Pro Ser Ala Ala Pro
65                  70                  75                  80

Ala Pro Arg His Ser Arg Pro Pro Ala Pro Ser Ala Ala Gln Ala
                85                  90                  95

Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
        115                 120                 125

Ser Val Leu Ala Arg Ser Ala Ala Pro Thr Glu Glu Glu Asp Glu Asp
    130                 135                 140

Cys Arg Ser Tyr Cys Gly Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
            180                 185                 190

Ala Arg Tyr Asp Thr Leu Leu Arg Leu
        195                 200
```

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77

```
acacagatac attcgtcgat ccaccagacc accactgtcc agtgctcggc tcggttacgc      60
acgcacgcac acaaatagga gtacctgttt tacaccaaga tactagcaag cccaagccga     120
gtcgacaaac aagcagcagg aagaggcatg gcgctcgcgg aggggaacgg cgcggccatc     180
ttcggcgagg agcaggaggc gctggtgctc aagtcgtggg ccctcatgaa gaaggactcg     240
gccgacctcg gcctccgctt cttcctcaag atcttcgaga tcgcgccgtc ggcgaagcag     300
atgttctcgt tcctgcgcga ctccgacgtg ccgctggaga agaaccccaa gctcaagacc     360
cacgccatgt ccgtcttcgt catgacctgc gaggcggcag cgcagctacg gaaggccggg     420
aaggtcaccg tcagggagac gacgctcaag cggctgggcg caacgcactt caagtacggc     480
gtcgccgacg gccacttcga ggtgacaagg ttcgcgcttc ccgccgactt gtggagcctg     540
gagatgaaga acgcctggag cgaggcttac aaccagctcg tggcggccat caagcaggag     600
atgaagcctg ccgcatgatg ctgcatgctg ctacatactc ggcctccgag ttccccctac     660
gatgcaccac catctccaag ttctttcatt gtcttgtg                             698
```

<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 78

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Pro Ala Asp Leu
        115                 120                 125

Trp Ser Leu Glu Met Lys Asn Ala Trp Ser Glu Ala Tyr Asn Gln Leu
    130                 135                 140

Val Ala Ala Ile Lys Gln Glu Met Lys Pro Ala Ala
145                 150                 155
```

-continued

```
<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79
aatccaatct cccccgatcc ccaatcgcga attccctct ccggcaggcg aagcaatcga      60
ggggcaccct ttcatctcgt caagatgcag atctttgtga agaccctcac tggtaagacc     120
atcaccctcg aggttgagtc ctcggatacc attgacaacg tcaaggctaa atccaggac     180 aaggagggga tccctccgga ccagcagcgc ctcatctttg ccggcaagca gctcgaagat    240
gggaggacgc ttgctgacta acatccag aaggagtcca ccctccacct cgtgctcagg     300
ctcaggggtg gtatgcagat ctttgtcaag actctcaccg gcaagacgat tactcttgag    360
gttgagtcct cggacacgat cgacaatgta aaggtgaaga tccaagacaa ggaggggatc    420
ccaccggacc agcagcgcct catctttgcc ggcaagcagc tcgaggatgg ccgcactctg    480
gctgactaca acattcagaa agagtcgacc cttcaccttg tgctcaggct gaggggaggc    540
atgcaaatat ttgtcaagac tctgactggc aagaccatca cgcttgaggt ggagtcgtct    600
gacaccattg ataatgtgaa ggcgaagatc caagacaagg agggcatccc gccggaccag    660
cagcgcctga tctttgccgg taagcagctg gaggatggtc gtaccctggc agactataat    720
attc                                                                 724

<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ala Asp Tyr Asn Ile Gln Lys Glu
 50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
210
```

```
<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81
gtgtagttga aggagcagaa gaagaagaag agaaggtggt accgccttca attctctttt      60
tctctctcca tttctcatcc tcatcatctt attattcctc ttccatctct attctccata     120
acacccacca caccacttgt gaaaaacctc attaatatca cacactgaca tgtatctctg     180
agctccaatc caatacaaga ccacaccttg tcgtgtcgga cgaaccttgg tgtctgtttt     240
tttttttttt tttcattatt ttctccgaag agatgaggaa gggcaraggt ggaggcgcct     300
cggcggcggc ggtggatgtg aacggatcca ttttaaagga gcctcggtac cggggcgtga     360
ggaagagacc gtgggggaga ttcgccgcgg agatcagaga cccgttgaag aaagccaggg     420
tttggttggg aaccttcaat tctgccgagg atgctgctcg tgcctacrac gccgccgctc     480
ggactctccg aggtcccaag gccaaaacaa atttccccccc tctctcacct ttttgctatc     540
cacaccccac caccgatcct ttcttstaca ctggtttcca cgatcaacac caccaccaca     600
acaacaacaa ccttaacaac cctcaaagac ccacttcaag tggcatgagt agcmccgttg     660
agtccttcag tgggcccnnc ccttttttccc ccaccaccac cmctaccacc acaaccacaa     720
```

-continued

```
ctgcgacgcc gttttgact gctacgcgga gatacccgcg cactccccct cttgtccctg    780
aagactgcca cagtgactgc gactcttcct cctccgtcgt tgacgacggc gacgacaaca    840
tcgtttcgtc gtcgtttcga cctcccttgc cgtttgatct caacgcgctg ccgtttgatg    900
atgctgccgc ggatgatgat ctacgccgca ccgcgctttg tctctgatga tgattatcgt    960
gcgatgatga tttttaattt ctcattttt tacttgattt ttttgttatt gctatgcaga    1020
agaaatatat atttaaaatg atgatcagat gtaagattat ggtaatatga tcttaattct    1080
gtgagaggaa gattccgtgt tggttatatt ttcttctttt tattattttt ttaaacattt    1140
ttatttagaa ggaaatattg aatgaaaaga aaaagagaa agtaattatg atcg           1194
```

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

```
Met Arg Lys Gly Arg Gly Gly Ala Ser Ala Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asn Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Xaa Phe Ser Pro Thr Thr Thr Thr
    130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Ser Val Val Asp Asp Gly Asp Asp Asn Ile Val Ser
            180                 185                 190
```

-continued

```
Ser Ser Phe Arg Pro Pro Leu Pro Phe Asp Leu Asn Ala Leu Pro Phe
            195                 200                 205

Asp Asp Ala Ala Asp Asp Asp Leu Arg Arg Thr Ala Leu Cys Leu
    210                 215                 220

<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

Met Cys Glu Ala Ala Ala Pro Arg Tyr Arg Gly Val Arg Lys Arg Pro
1               5                   10                  15

Trp Gly Arg Phe Ala Ala Glu Ile Arg Asp Pro Ala Lys Arg Ala Arg
            20                  25                  30

Val Trp Leu Gly Thr Tyr Asp Ser Ala Glu Ala Ala Arg Ala Tyr
        35                  40                  45

Asp Val Ala Ala Arg Asn Leu Arg Gly Pro Leu Ala Arg Thr Asn Phe
    50                  55                  60

Pro Leu Val Ser Ser Leu Pro Leu Pro Ser Pro His Tyr His Leu Pro
65                  70                  75                  80

Gly Lys Ala Ala Ala Ala Pro Pro Val Ala Gly Pro Ala Cys Ser
                85                  90                  95

Ala Ser Ser Thr Val Glu Ser Ser Gly Pro Arg Gly Pro Arg Pro
            100                 105                 110

Ala Ala Thr Ala Ala Ala Val Pro Arg Arg Val Pro Arg Pro Ala
        115                 120                 125

Pro Pro Ala Pro Asp Ala Gly Cys His Ser Asp Cys Ala Ser Ser Ala
    130                 135                 140

Ser Val Val Asp Asp Ala Asp Ala Ser Thr Val Arg Ser Arg Val
145                 150                 155                 160

Ala Ala Phe Asp Leu Asn Leu Pro Pro Leu Asp Arg Asp His Val
                165                 170                 175

Asp Leu Cys Thr Asp Leu Arg Leu
            180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
```

```
<400> SEQUENCE: 84

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Glu Ile Arg Asp Pro Trp Lys
        35                  40                  45

Lys Ala Arg Val Trp Leu Gly Thr Phe Asp Ser Ala Glu Glu Ala Ala
50                  55                  60

Arg Ala Tyr Asp Ser Ala Arg Asn Leu Arg Gly Pro Lys Ala Lys
65                  70                  75                  80

Thr Asn Phe Pro Ile Asp Ser Ser Pro Pro Pro Asn Leu Arg
            85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
            115                 120                 125

Arg Pro Thr Ser Ser Ser Met Ser Ser Thr Val Glu Ser Phe Ser Gly
        130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Gly Gly Gly Ser Ser
        35                  40                  45

Val Pro Pro Pro Val Met Ser Pro Met Pro Met Thr Pro Pro
    50                  55                  60

Met Pro Met Thr Pro Pro Met Pro Met Thr Pro Pro Met Pro
65                  70                  75                  80

Met Ala Pro Pro Pro Met Pro Met Ala Ser Pro Pro Met Met Pro Met
            85                  90                  95
```

```
Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
            115                 120                 125

Pro Pro Ala Met Ala Ala Ser Pro Asp Ser Gly Ala Phe Asn Val Arg
            130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 86

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
            85                  90                  95

Leu Arg Phe Tyr Ala Gly Gly Ala Gly Glu Gly Phe Gln Asp His Arg
            100                 105                 110

Arg Pro Thr Ser Ser Gly Met Ser Ser Thr Val Glu Ser Phe Gly Gly
            115                 120                 125

Pro Arg Pro Val Arg Pro Met Pro Pro Ser Ala Val Thr Gly Arg
            130                 135                 140

Arg Tyr Pro Arg Thr Pro Pro Val Ala Pro Gly Asp Cys Arg Ser Asp
145                 150                 155                 160

Cys Asp Ser Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
            180                 185                 190

Leu Asn Ala Pro Pro Leu Glu Glu Gly Asp Val Ala Asn Gly Leu Gly
        195                 200                 205

Glu Asp Leu His Cys Thr Leu Leu Cys Leu
    210                 215
```

-continued

```
<210> SEQ ID NO 87
<211> LENGTH: 225
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87

Met Arg Arg Gly Arg Ala Ala Ala Pro Ala Pro Val Thr Gly Glu
1               5                   10                  15

Pro Asn Gly Ser Gly Gly Ser Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Thr Arg Val Trp Leu Gly Thr Phe Asp Ser Ala Glu Asp Ala Ala
50                  55                  60

Arg Ala Tyr Asp Ala Ala Ala Arg Ala Leu Arg Gly Pro Lys Ala Lys
65                  70                  75                  80

Thr Asn Phe Pro Leu Pro Tyr Ala His His Gln Phe Asn Gln Gly
                85                  90                  95

His Asn Pro Asn Asn Asp Pro Phe Val Asp Ser Arg Phe Tyr Pro Gln
            100                 105                 110

Asp Asn Pro Ile Ile Ser Gln Arg Pro Thr Ser Ser Ser Met Ser Ser
        115                 120                 125

Thr Val Glu Ser Phe Ser Gly Pro Arg Pro Pro Ala Pro Arg Gln
    130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                165                 170                 175

His Gly Asp Cys Glu Lys Glu Asn Asp Asn Asp Asn Ile Ala
            180                 185                 190

Ser Ser Ser Phe Arg Lys Pro Leu Leu Phe Asp Leu Asn Leu Pro Pro
        195                 200                 205

Pro Met Asp Asp Ala Gly Ala Asp Asp Leu His Cys Thr Ala Leu Cys
    210                 215                 220

Leu
225

<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Leu Ala Ala

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80
```

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180
taaccatggc cagcttcaca wgctttcctt ttgctcacat tgyctatggc tttagytcat     240
ytctctttag ctcwatctcc catgatggct ccttctggct ccatgtccat gscgckchat     300
gccatagcgg cggctctcca atgccaatga tgactccacc acctatgcca atgatgactc     360
cmccgcctat ggctatggct ccaccaccta tgcctatgac tccaccacca atgcccatgg     420
ctccgatgcc aatgactcca tcttcaagtc caatgagccc accaactact atggccccaa     480
gtccagaaac agtccctgat atggcttcgc caccgatgat gccgggaatg gagtcttctc     540
cttctccggg acccatgcca ccggcaatgg cctctccaga ttccggagca ttcaatgtaa     600
gaaacgacgt cgtagcaatt tcgttccttg ttgcagctca tttgctccta gtttgagatt     660
attattaaat tggccagcgt cgtgttgtgt aatttacttt cattttttct cgagccatta     720
gttttcatgt tttatcatat atttgggttt gtgtttgata tggtacgatt cagmc          775

<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91
gctcattagg gtttctcatc tacggcgtgg tgttcctcct tcctgctctg aaaaatggcg      60
aagagaacga agaaggttgg aatcgtcggc aaatacggaa cacgttatgg tgcgagtatc     120
aggaagcaga ttaagaagat ggaggtcagc cagcacagca agtacttctg tgagttctgt     180
ggcaagtacg gagtgaagcg aaaggctgtt ggtatctggg gttgcaagga ttgtggcaag     240
gtcaaggcag gtggtgctta cacaatgaac accgccagtg cggtcactgt tagaagcacg     300

| | |
|---|---|
| atcagaaggt tgagggagca gatcgagggt taaaagtctg ctgaggaaga tgctgagaca | 360 |
| gtatacgctt gtatcgactt ggtatcaacg ataatacaga ggaagctgag gaagatcaag | 420 |
| gagaaggact cagaccatgg aaggcacatg aaaggtttca acagattgaa ggtaagggaa | 480 |
| ccagtgattg agccggttgt ggaggatgtt gaggacagta ctgactcgag cgtaggagaa | 540 |
| gaagaagaag aggatgattt gatcaaggag attgtccgta ccaagacttt cgagatgcca | 600 |
| ccattgactg tcgctgaggc agtcgagcag ctggaactag tcagtcacga cttctatggc | 660 |
| ttccaaaatg aaaactggtg agataaacat agtgtacaag agaaagaag gaggttacgg | 720 |
| tctgataatc ccaaagaaag acgggaaggc cgagaaggtt gagccgcttc caaccgagca | 780 |
| attgaatgaa cactctttcg ccgagtagac tgcctctgca cacaccaaaa ccgataagct | 840 |
| catctctcct tacagtttac ctgtgtagga gttagggttc ttgaataaac aatgcaacaa | 900 |
| agattgtaga agtcagtgta cataaaaaaa tggccaacca ctctttgtta cttttgtggt | 960 |
| gaaaaggaag atcttaattc tctttccatc agatgatagc aatacatttt tcataaaaca | 1020 |
| agaatgttac at | 1032 |

<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92

| | |
|---|---|
| atctagcttc aacctttttt tcctctcact actcaattca atatggctgt ctcacgttac | 60 |
| attatcctac tcttatcctt cacctacttg gctgccttct ccaccgctca agctccatca | 120 |
| atgtcaccaa tgatgatgcc catggcacca ccaccatcga cgatgcccat gacaccacca | 180 |
| ccatcgacga tgcccatgac accaccacca cgcccatga ccatgacacc accaccaatg | 240 |
| atgatgccca tgacaccacc accaatgccc atggggacac caccaatgac aatgcccatg | 300 |
| ggaccgccac caatgatgat gcccatgagc ccaggaccat ccatgatgcc agcctccccg | 360 |
| ccatcaccca tgggaccgtc catggcacct gaaccagcta ccatgtcgcc tggaccctcc | 420 |
| atgacgcctg ctgagacacc agccagtggc gctatcatgc agtattctag catcactatg | 480 |
| ttgggcattg tg | 492 |

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93

| | |
|---|---|
| agatataatc gaaaaaaatt actgtttgga tatattccac tatttagaaa gcaaatgga | 60 |
| ctacgaaaac ttgagtaaca aggtaagcca cacaaatggg aatgactccc cattacaatg | 120 |
| aagggccaac ttcattttca atgaatccca ctataaaaac tttagcaatg caaaagctaa | 180 |
| aacatcaacc atttcctcat ccactttcac tggaatcaca atcctgaaac aaaaacatct | 240 |

```
tagcatttaa catactacta gacaacatga ccaccacatt ggaaagaggt ttctcggaag    300
agcaagaagc tctggtggtg aagtcatgga atgtcatgaa gaagaattct ggagagttgg    360
gtctcaagtt tttcttgaaa atatttgaga ttgctccatc agctcagaaa ttgttctcat    420
tcttgagaga ttcaacggtt cctttggagc aaaatcccaa gctcaagccc catgccgtgt    480
ctgtctttgt aatgacctgt gattcagcag ttcagctgcg gaaggccggg aaagtcactg    540
tcagagaatc aaacttgaaa aaattaggtg ctacccattt tagaaccggc gtagcaaacg    600
agcatttcga ggtgacaaag tttgcactgt tggagaccat aaaagaagct gtaccagaaa    660
tgtggtcacc ggctatgaag aatgcatggg gagaagctta tgatcagctg gtcgatgcca    720
ttaaatctga aatgaaacca ccctcctctt agactccagt ttaagcagtt cctttccttc    780
cctctcaatt ctcaaattgt tatattaata aaagtgagaa agtttaggct tgtgcttta    840 ttttgtgtga atgtaatata ctttgtgtac gtagacttgg ctattgggag ttgctaggtt    900
gggaagtgtt tcgcattcaa caattctgta gttgaaggtg attaaatgaa ttatagctat    960
ttgtttcttc                                                          970

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94
tcgtatccac ccaacctccc actgtaaaaa agagcagcgg aacgtgcgtg catccatcca     60
attccaatcc cagtcccaat cccaccagtg tccagtgctc ggggaaccga cacagctcct    120
cagcagagaa gccagcccga tcagcagaca gcaggcatgg cgctcgcgga ggccgacgac    180
ggcgcggtgg tcttcggcga ggagcaggag gcgctggtgc tcaagtcgtg ggccgtcatg    240
aagaaggacg ccgccaacct gggcctccgc ttcttcctca aggtcttcga gatcgcgccg    300
tcggcgaagc agatgttctc gttcctgcgc gactccgacg tgccgctaga gaagaacccc    360
aagctcaaga cgcacgccat gtccgtcttc gtcatgacct gcgaggcggc ggcgcagctc    420
cgcaaggccg ggaaggtcac cgtgagggag accacgctca agaggctggg cgccacgcac    480
ttgaggtacg gcgtcgcaga tggacacttc gaggtgacgg ggttcgcgct gcttgagacg    540
atcaaggagg cgctccccgc tgacatgtgg agcctcgaga tgaagaaagc ctgggccgag    600
gcct                                                                604

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95
acgccgtccg tttctggctc atcaggaggt ccaaaggccg cgcaagtcga cctatataag     60
cgcctccgct ccagcttggg atcaaatcac gaccaacacg taccggatct tgaccgaccg    120
```

| | |
|---|---|
| aaccattcag tgctcgcgct cactcacgca tcatagccaa gttaagcggg aaggaaggaa | 180 |
| ggaaggaagc catgtctgcc gcggagggag ccgtcgtgtt cagcgaggag aaggaggcgc | 240 |
| tggtgctcaa gtcatgggcc atcatgaaga aggattccgc caaccttggg ctccgcttct | 300 |
| tcctcaagat cttcgagatc gcgccgtcgg cgaggcagat gttcccgttc ctgcgcgact | 360 |
| ccgacgtgcc gctggagacc aaccccaagc tcaagaccca cgccgtgtcc gtcttcgtca | 420 |
| tgacgtgcga ggctgctgcg cagctgcgga agcccgggaa gatcaccgtc agggagacca | 480 |
| ccctgaagag gctgggcggc acgcacttga atacggcgt ggcagatggc cactttgagg | 540 |
| tgacgcggtt cgctctgctc gagacgatca aggaggcgct tccggcggac atgtgggggc | 600 |
| cggagatgag gaacgcgtgg ggcgaggcct acgaccaact ggtcgcggcc atcaagcaag | 660 |
| agatgaagcc ctctgagtag ctcatccatt gtactcatat catatgccac gcaacttccg | 720 |
| tccatatccg tccaactttc gttgcttgac cggttcactc atgtcaccat attgtgtttg | 780 |
| tattgtgtgt ttacgtgtac taacgcatat tgtaaaatgg gcattcaata aaggaacaaa | 840 |
| ttgtgc | 846 |

<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96

| | |
|---|---|
| ctcttgtctt agtctaataa acaacacgga cgcagagcct tcgatccaga aaccatgact | 60 |
| aagagaacga agaaggcagg cattgtcgga aaatatggta cccgatatgg tgctagtttg | 120 |
| cggaagcaga ttaagaagat ggaagttagt cagcatagca aattcttttg tgaattttgt | 180 |
| gggaagtatg ctgtgaagag gaaggctgtg gaatatggg gatgcaagga ttgtggtaaa | 240 |
| gtgaaagctg gcggtgccta cactttgaat actgcaagtg ctgtcactgt gcgcagcacc | 300 |
| atccggaggt tgagggaaca aaccgagggt tgagcttttt ggttgatgtt agattttgag | 360 |
| caaattaact ggagaaatga ttcgtttttg tttaggaagc tgtattgttt caacttacaa | 420 |
| tgcagtgtga attgctttcg | 440 |

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97

| | |
|---|---|
| atatawcttg actctccgca attccctgtc tcckccgccg cagcttccgt ctcccggatt | 60 |
| tcgccgcctg ccgcakccgc agcagctcgc cgsccacgcs tcctayccgt cgacgagatg | 120 |
| acgaascgca ccaagaaggc tggaattgtc ggcaaatatg gtacccgtta tggtgccagt | 180 |
| ttgcgtaagc agatccargaa gatggaggtg tctcagcact ccaagtactt ckgtgagttc | 240 |
| tgtgggaagt ttgctgtgaa gaggaaagsa gttggaattt ggggatgcaa tggactgtgg | 300 |

```
gaaggwsaag gaaaccttcg ccwkaaaccg tgagctcgaa gtgmggtcca ctccaggwgg    360
gccatgctcg gggccttggg swgcagtctt ccccgaagct attgtyccgc aacggggtca    420
agtttggaga agctgtgtgg ttcaaggccg ggtcccagat ctt                      463
```

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98

```
aacaaaccct cgttcacggt tcaacttcag cagccgcgcc tctaacttgt agcagcgata     60
cctcttctct tatcactaaa aaatgaccaa gagaaccaag aaggccggta ttgttggaaa    120
atacggcacc cgatatggtg ctagtttaag gaagcaaatc aagaagatgg aagttagtca    180
gcacagtaaa ttcttttgtg agttctgtgg aaagtacgct gttnagagga aggccgtggg    240
tatttggggc tgcaaagatt gtggaaaagt gaaggctgga ggtgcttaca cattgaatac    300
tgcgagtgct gtcactgtcc ggagcaccat tcggaggctg agagagcaga ctgagagttg    360 aaaagcagttt acacttttca tttgtttcca aagcttattt taaaattatc atacaatttt    420
ggcaggtcta tgttaggaat attagtaatg tgctactt                            458
```

<210> SEQ ID NO 99
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99

```
ctcaaaaccc taggcttcca tatataactt gactctccac aattccctgt ctccgccgcc     60
gcagctttcg tctcccggat ttcgccgccg cagccgctca ccgccacgc ctcctacccg     120 tcgacgagat gacgaagcgc accaagaagg ctggtattgt cggcaaatat ggtacccgtt    180
atggtgccag tttgcgtaag cagatcaaga agatggaggt gtctcagcac tccaagtact    240
tctgtgagtt ctgtgggaag tttgctgtga agaggaaagc agttggaatt tggggatgca    300
aggactgtgg gaaggtgaag gctggcggtg cttacactat gaacactgcc agtgcggtca    360
ctgtcaggag cactatccgt cgtttgaggg agcagactga agcataagtt gctactagtg    420
ttttgtccta gtgaatcatc tgggatttcg cagtttagac gatactttgg attcagttcc    480
attggctgtt tagtcaagga ttatctttgt acttggtgcg atgatgttct gttatgttat    540
tctcccaccc ttttgttgcc tgattccact ctgatttact gtggattctg atttgccttc    600
```

<210> SEQ ID NO 100
<211> LENGTH: 546
<212> TYPE: DNA
<213> ORGANISM: Zea mays

```
<220> FEATURE:
<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100
aagcatccac aattccacat aacctcgccc gcgccgcctc ccccacgaga cgccttcttg    60
ctctcgcttc cggtgacgcc cgccacttcc tccccgacga gatgacgaaa cgcaccaaga   120
aggcaggaat cgttggcaaa tatggtacca ggtatggtgc cagtttacgt aaacagatca   180
agaagatgga ggtctcgcag cactccaaat acttctgtga gttctgtggc aagtttgccg   240
tgaagaggaa agcagttggt atctggggat gcaaggactg tgggaaggtt aaggccggtg   300
gcgcctacac aatgaacact gctagtgcgg tcactgtgag aagcacaatc cggcgcctgc   360
gggagcagac cgaagcatga ttgcgggcag cttgaaaagg agtacctgga ttttgtagt    420 tcagccaaga gccgtgaacc attttgcctt tttagctaaa tgaacaagaa atgtttatct   480
atctgtagtg accactttgt actcatggtt tgtcatgcta aattgatggt atgcactatg   540
caatgc                                                              546

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101
atatataact tgactctccg caattccctg tctccgccgc cgcagcttcc gtctcccgga    60
tttcgccgcc gccgcagccg cagcagctcg ccgcccacgc ctcctacccg tcgacgagat   120
gacgaagcgc accaagaagg ctggaattgt cggcaaatat ggtacccgtt atggtgccag   180
tttgcgtaag cagatcaaga agatggaggt gtctcagcac tccaagtact tctgtgagtt   240
ctgtgggaag tttgctgtga agaggaaagc agttggaatt tggggatgca aggactgtgg   300
gaaggtgaag gctggcggtg cttacaccat gaacactgcc agtgcggtca ctgtcaggag   360
cactatccgt cgcttgaggg agcagactga agcataagtt gctactagtg ttttgtccta   420
gtgaatcatc tgggattttg cagtttagac gatactttgg attcagttct gttggctgtt   480
tagtcaagga ttatctttgt acttggtgcg atgatgttct gttatgttat tctctcaccc   540
tttttttgcc                                                          550

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35
```

<400> SEQUENCE: 102

```
aaaaattcat tgatcgaaaa aaagaaaaaa gaaagaaaag aaaagatgca gatcttcgtg      60
aaaaccttga ccggcaaaac cataacccta gaggttgaaa gcagcgacac catcgacaat     120
gtcaaatcca aaatccagga caaagagggg ataccacctg atcaacagag gctcatcttt     180
gctgggaaac aacttgagga tggtcgaacg ctagctgact acaacattca gaaagagtcc     240
actcttcact tggttctgag gcttaggggt gggaccatga tcaaggtcaa gactctcact     300
ggtaaagaaa tcgaaattga tatcgaacct accgatacta ttgaccggat caaggaacgt     360
gttgaggaga aagaaggcat ccctcctgtt caacaaaggc tcatctatgc tgggaaacag     420
ctagctgatg acaaaacggc aaaggactac aacatagagg gaggctctgt tcttcatctg     480
gtccttgctc tcagggggtgg ttctgactaa ataactattt gctctagagt tcctttcaat     540
ggctttggtt ggttgaatcc atgagacaaa gtgaatacaa tttggatttc gtgctttggt     600
tactatgatg ctatttcagc tggtttggat caatttacca aaaaaaaaa aaaaaaaaa      660 aaaaaaag                                                              668
```

<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103

```
aattacaaat acaaatacga ataccttct ctctcacaca aaacactagt ccctcccttc      60
ttccttgtct ctttctcttc tcaacaacat gcagatcttc gtcaagactt tgactggcaa    120
gaccatcacc ctcgaggtcg agagtagcga caccatcgac aacgtcaagg ccaagatcca    180
ggacaaggaa ggtatccctc ctgaccagca gagtttgatt tttgctggta agcagctgga    240
agatggtcgc actcttgctg attataacat acaaaaggaa tcaacacttc acttggtctt    300
gaggctcagg ggaggaacca tgattaaagt gaagactcta actggaaaag aaattgaaat    360
tgacattgag ccaactgata caatcgaccg gatcaaggaa cgcgttgaag aaaaagaggg    420
aattccacct gtgcagcaga gactcatata tgcaggtaaa cagcttgctg atgacaaaac    480
```

```
agctaaagag tacaacattg agggtggttc tgtacttcac ttggtgcttg cattgagggg      540
tggtacttat tagtgtagat gccatatcag aacccaaaga catgaaagga agctctattc      600
ctgccccgtc tctctgaaga catcattgtt cttttatgng cttggttttt gtaattgtgg      660
ctactattgg tggncagtaa ctcagtatcn ttttagntgn atgctattta aaanccctaa      720
ggtgggcctt tatatgaata tctgaaccaa tg                                    752
```

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104

```
gaaatcaaat aaaaaaatct taagcaaga aagaaagaa atgcagatc ttcgtcaaaa         60 ccctgacggg gaaaaccata accctggagg ttgaaagcag cgacaccatc gacaatgtca     120
aagccaaaat ccaggacaaa gaaggaatac cgccggatca gcagaggctg atcttcgctg     180
ggaagcaact agaagacggt agaacccttg cggactacaa catccagaaa gagtccactc     240
ttcacttggt cttgaggctt aggggtggca ccatgatcaa ggtcaagact ctcactggca     300
aagaaatcga gattgacatc gaacctaccg acaccattga tcgcatcaag gagcgtgttg     360
aggagaaaga aggcatccct cctgttcaac agaggctcat ctacgctgga aaacagctag     420
ctgatgacaa gacggcmaaa gactacaaca tcgagggagg ctctgtttct gcatctggtt     480
cttg                                                                   484
```

<210> SEQ ID NO 105
<211> LENGTH: 580
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105

```
aagaaaaagg aaattttctt gggcgttctt cggcttcgtt gtcacaaggt tcgagttcgt      60
caccgtctag tacgactgtg cgagggagga agaggcgagg agaagatgca gatcttcgtg     120
aagaccctga cggggaagac catcaccctc gaggtggaga gcagcgacac cgtcgacaac     180
gtcaaagcca aatccagga caaggaaggg attcccccag atcaacagcg actgatattc     240
gctggcaagc agctggagga tggacgcacg ctggctgact acaacatcca aaaggagtca     300
actcttcatt tggtcctcag gcttaggggt ggaaccatga tcaaggtcaa aactctcact     360
gggaaagaga tcgagatcga cattgaaccc actgactcga ttgacaggat caaggagcgt     420
gttgaagaga aagaaggcat tcctcccgtg cagcaaaggc tcatctatgc tggtaagcag     480
cttgctgatg acaagaccgc aaaggactac aacatcgagg gtggatctgt cctccatctt     540
gtncttgctc tgaggggtgg ttactagtct aaacctgatg                           580
```

```
<210> SEQ ID NO 106
<211> LENGTH: 987
<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106
attccatcaa cttcagacac acagatctct tctcaatcac attacttctg gttctcccac      60
catgaggaaa gggagaggct cttccgccgt tccacccgcc cttcccggat ctgtgaagga     120
gccgaggtac agaggcgtta ggaagagacc ttggggccgt ttcgccgccg agatccgtga     180 cccctttgaaa aaatcccgag tctggctcgg cacgttcgac tccgcggagg aagccgcacg     240
cgcctacgac gcagccgctc gtaacctccg cggtccaaag gccaagacca acttccaaat     300
cgactgttct ccttcctctc ctctccaacc actccatcat cggaaccaga tcgatcccctt     360 tatggaccac cggttatacg gcggagagca ggaggttgtt atcatcagcc ggccggcgag     420
tagcagcatg agcagccaccg ttaagtcgtg cagcggagtg agaccagcgt cttcttccgt     480
ggcgaaggcg gcgacgaaga gatatccacg gactccgccg gtggcgccgg aggattgccg     540
cagcgactgc gattcgtcgt cgtcggtggt tgaagacgga sacgacatag cttcgtcgtc     600
ttcgcggcgg aaaccgccgt ttgagtttga tcttaatttt ccsccgttgg atggcgttga     660
cttattcgta ggcgcggacg atctccactg caccgatctg cgtctttgat ctttgagcac     720
aatgacaaca aagatgatga agaagtgata gggagagaga gtttgtgtta agatctgttg     780
ttgtaagaac cagatctgtg tttcattcac ttgtctgttt cttataaaga tcaaaccttt     840
gttacatgta acacttatat agctgctgat gattcttaat tattcaaaat ccaaagtctg     900
tagaatttat acagtatcta tcactgatgt gcttatggat ggtttggagt atgaggctac     960
attttcataa atacattcaa tgtgtgt                                         987

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107
ctctccttcc ttcacggatt cccaaatact cgcttccaat accaattctc cgatccacgt      60
tcgttcccgc accctcgcgc tccgctgatc cggcggcatg cggcgccgcg gcgtggcggc     120
ggctgatgcg gacggtgacg tggagttgcg gttccgcggg gtgcggaaga ggccgtgggg     180
ccggtacgca gcggagatcc gggacccggc gaagaaggcg cgcgtctggc tcggcacatt     240
cgactccgcc gaggacgccg cccgcgccta cgacgccgca gcgcggatgc tgcgcgggcc     300
caaggccagg accaacttcc cgctccccgc cgcagccgcc ctccaccacc ccacatgcc     360 cgctgctgcc gccgcagcag ctccaccata caacacatat cccaccgcca cgggcgtcgt     420
ctcgacgccg ccggtcgcca gaccggcttg cagcagcctc agctccaccg tggagtcctt     480
cagcggcgcg cggccgcggc ctgtgctccc gccgcggttc cctccgccgt cgattcctga     540
```

```
tggcgactgc cgcagcgact gtggttcctc ggcctcggtc gtggacgacg actgcacgga    600
cgcggccgcc tctgcgtcgt gccccttccc gctcccgttc gacctcaacc tgccccccagg   660 cggcggcgga gccggcgtcg ggttttacgc cgatgaggag gatgagctca ggctcacggc    720
gctgcggctg tgacgtcgag ctcaatcgag ccgctgctta gaagaggaa aaggagaaaa     780 atatttggtt cttcccttct cttgtagccg acacgaactc tccatccact acgatgttgt    840
tgtttacttg atctgattat gatatttgcc tgaatcctag tcaacttacc tgcatgcatg    900
cctgcttgtt ttctggcgat tgaggattat cgccaaacgc caaatcttgc agcagctgtt   960
gtactgtaat atatcaacat tttacttcct tcctcttatg aggaaagaga cagataaagt   1020
aacttatttc aatc                                                     1034

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108
aaacaaaaaa ccaccagggg aagaagggaa agacacacgc cactgtgacc aaaccctagg    60
ccggccgcga tgcgcaaggc gaggccgccg cagccccagc cgcagccgtc gcagcagtcg   120
ccggagatcc ggtaccgcgg cgtgcggaag cgccctcgg gccgctacgc cgccgagatc    180
cgggaccccg ccaagaagac gccgatctgg ctcggcacct tcgactgcgc cgaggacgcc    240
gcccgcgcct acgactccgc cgcccgatcc ctccgcgggc ccaccgcccg caccaacttc    300 ccgcccctcct ccgccacgca gccgccgccg aggcccctc cccccgcggc cgcggccgcg   360
gccgccacgt ccagccagag cagcaccgtc gagtcctgga gcggcggcgg gccccgcgcc    420
cccgccaggg cccgcagcgc cgcccgagcg ggcacggcca aggaggggga ggaggactgc    480
cgcagctact gcggctcctc gtcctccgtc tcctcgagg agggcgcgga cgacgcggcc    540
gcctcccgct ccccgctgcc cttcgatctg aacatgccgc cccgcagga ggggcgctt     600 gacgccgagg ccgatcagat gacctgccgg tacgacacgc tgctccgcct ctagctccac    660
gacgacgaga gcaaggattc gtgggagggg aactgggaaa aggaacgaga aaagcgcttg    720
cccccgctcc gctccggtcc gtcttccgat gatctcgtgg tgttctctct ttgttagaaa    780
tggataattc ttgccattt ttttcttac tttctttcct tcttcttttt tttttcttct     840
taccactttg attcgatatg tgaataattg agtcatgtaa gctgcgagca aggaaatctg    900
agcttttcct t                                                        911

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
      Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 109

Met Glu Ser Glu Gly Lys Ile Val Phe Thr Glu Glu Gln Glu Ala Leu
1               5                   10                  15

Val Val Lys Ser Trp Ser Val Met Lys Asn Ser Ala Glu Leu Gly
            20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
        50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
            115                 120                 125

Val Pro Glu Met Trp Ser Pro Glu Met Lys Val Ala Trp Gly Gln Ala
        130                 135                 140

Tyr Asp His Leu Val Ala Ala Ile Lys Ala Glu Met Asn Leu Ser Asn
145                 150                 155                 160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110
gtctcttaaa aaggatgaac aaacacgaaa ctggtggatt atacaaatgt cgccttatac      60
atatatcggt tattggccaa aagagctatt ttaccttatg gataatggtg ctactatggt     120
tggagttgga ggtgtagttc aggcttcacc ttctggttta agccctccaa tgggtaatgg     180
taaatttccg gcaaaaggtc ctttgagatc agccatgttt tccaatgttg aggtcttata     240
ttccaagtat gagaaggta aaataaatgc gtttcctata gtggagttgc tagatagtag      300
tagatgttat gggctacgaa ttggtaagag agttcgattt tggactagtc cactcggata     360
ctttttcaat tatggtggtc ctggaggaat ctcttgtgga gtttgatatt tgcgagtata     420
atctttgaac ttgtgtagat tgtacccaaa accgaaaaca tatcctatat aaatttcatt     480
atgagagtaa aattgtttgt tttatgtatc atttctcaac tgtgattgag ttgactattg     540
aaaacatatc ttagataagt ttcgttatga gagttaatga tgattgatga catacacact     600
cctttatgat ggtgattcaa cgttttggag aaaatttatt tataatctct cataaattct     660
ccgttattag ttgaataaaa tcttaaatgt ctcctttaac catagcaaac caacttaaaa     720
atttagattt taaagttaag atggatattg tgattcaacg attaattatc gtaatgcata     780
ttgattatgt aaaataaaat ctaactaccg gaatttattc aataactcca ttgtgtgact     840
gcatttaaat atatgtttta tgtcccatta attaggctgt aatttcgatt tatcaattta     900
tatactagta ttaatttaat tccatagatt tatcaaagcc aactcatgac ggctagggtt     960
```

```
ttccgtcacc ttttcgatca tcaagagagt tttttttataa aaaaatttat acaattatac    1020
aatttcttaa ccaaacaaca cataattata agctatttaa catttcaaat tgaaaaaaaa    1080
aatgtatgag aattttgtgg atccatttt gtaattcttt gttgggtaaa ttcacaacca    1140
aaaaaataga aaggcccaaa acgcgtaagg gcaaattagt aaaagtagaa ccacaaagag    1200
aaagcgaaaa ccctagacac ctcgtagcta taagtaccct cgagtcgacc aggattaggg    1260
tgcgctctca tatttctcac attttcgtag ccgcaagact cctttcagat tcttacttgc    1320
aggttagata ttttctctct ttagtgtctc cgatcttcat cttcttatga ttattgtagc    1380
tgtttagggt ttagattctt agttttagct ctatattgac tgtgattatc gcttattctt    1440
tgctgttgtt atactgcttt tgattctcta gctttagatc cgtttactcg tcgatcaata    1500
ttgttcctat tgagtctgat gtataatcct ctgattaatt gatagcgttt agttttgata    1560
tcgtcttcgc atgtttttta tcatgtcgat ctgtatctgc tctggttata gttgattctg    1620
atgtatttgg ttggtgatgt tccttagatt tgatatacct gttgtctcgt ggtttgatat    1680
gatagctcaa ctggtgatat gtggttttgt ttcagtggat ctgtgtttga ttatattgtt    1740
gacgttttgg ttgttgtatg gttgatggtt gatgtatttt tgttgattct gatgtttcga    1800
tttttgtttt tgttttgaca gct                                              1823
```

```
<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111
atagagtttt actatgcttt tggaatcttt cttctaatgt gccaactaca gagaaataca      60
tgtattacca ctaggaatcg gaccatatca tagatatcag gattagataa ctagttctcg    120
tcgctatcac ttcgcattaa gttctagtaa ttgttaaaga ttctaatttt ttactaaaca    180
aaaactaaat caacatcaaa tatgcaaagt gtgtgttgtc cacacaagtg actcaaagta    240
tacgcaggtg ggattggacc atattattgc aaatcgtttc cgaaccactc atatttcttt    300
ttttctctcc tttttttatc cggagaatta tggaaccact tcatttcaac ttcaaaacta    360 atttttggt tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt    660
ttcttctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgctttga acctaaatct agcccagcca    900
acgaagaaga cgaagcaaat ccaaaccaaa gttctccatt ttcgtagctt ctttaagctt    960
tttcagtatc atagagacac ttttttttttt ttgattagaa                          1000
```

```
<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112
ttagtgaaat tatgacatta agtaaggttt tcttagttag ctaatgtatg gctattcaat      60
tgttatgtta ggctatttta gttagtatat gaatttaggc agtctatgca aatgatttcg     120
ttttcatttt ttcatatgta aacatcaaga tcaagtaacg ccattcgagt tgatattttt     180
tttttaaatt agtgtgtgta aattttggac cgcttatttg agtttgctaa tgaagttgca     240
tatatattac gttaaaccat aggcaaacta atttgaaaca tccgattcga tttcctgtaa     300
tttttcttgg ttaattgacc aaaatcaaga tcttcagaaa taaaataaaa gacgaaagaa     360
agctgtcgca aagcagattg tgttaaaaaa aagtggattg ggctcaaacg caacttgtcc     420
agcccgtgac aattacccta tacgcaagta agagtaacgt atcactggca aaagttggta     480
ttagttacga tatctttgtc atgggggcat gcatgggcat ggcttaagag ttaagcctta     540
agaagagtcc cacactcgtg actctcatga tcacttgttg tttcttacgg gcaaatacat     600
ttaactttat tcttcattta ttcacctata ttcttttgga taataacttt tctctatata     660
aaataacaaa catcgtacgt ttcatttatt tacaacaagc gatgagaatt aaaaggagac     720
cttaattgat gatactcttc ttttctctcg gttacaacgg gattattaca gataatgata     780
atctatatgg atgctgacgt ggaaaaacaa aatttggtga aacacgtcaa ttaagcacga     840
cttttccatg gctagtggct aagatcgttt catcacatgg ctatatcata taatacttgg     900
atgaattcaa aataaacgac tgagaaaatg tccacgtcac ggcgcaccgc tttggactta     960
agtctcctat aataaataca acaccaaaca ttgcattcca                         1000

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113
tgaagtcatt taatatgagt ttgacattag gtaaacctaa tctatgagat tatagaatgt      60
agcaaaacta tcaatgtttc ttttccaaaa tattttgtgg ttttttcttt tggttcatta     120
tgttttgtta tttgtgaatt attttaatat gaagtaatta tattgatttt atatgatata     180
catattattt tgatataaaa tttaacactt atccattaaa atagcatggg cataatcaaa     240
atcgggacta ttacgatgaa aaagatagtt aaattgtatg ataaaataaa atgtgtaaga     300
ttaaaatttt gggttttaga aaattactaa acaaaatata gacaaagtat gttgactatt     360
atttaaaatt taaatatcat caataagata tagttaaagt cattaagtgt atagcaaaat     420
gaaaattcta agattaaaat tcgattaaaa tttttttttac taaattaaat atttaaaaat     480
agggattatc atttactatt tacaattcta atatcatggg taaaaattga taactttttt     540
taaacccgcc tatctaggtg ggcctaacct agtttactaa ttactatatg attaacttat     600
taccactttt acttcttctt ttttggtcaa attacttttat tgtttttttat aaagtcaaat     660 tactctttgc attgtaaata atagtagtaa ctaaaatctt aaaacaaaat attcaacctt     720
```

```
tcccattatt ggaatggtaa tgtcttcaac accattgacc aacgttaagg aatgtctttt        780
aatatttttg gaacctaaat gctaatactg tataccacaa tcacttatga gtattgaagt        840
tgagatagag gaggtacaag gagaccttat ctgcagaaga caaaaagcca ttttttagcaa       900 aactaaagaa agaaaaaaga ttgaaacaca aatatgcgcc actcgtagtc caccootatc       960 tctttggcaa aagccacttc actcttttte ccttttat                                999
```

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114

```
ttaatactaa cattgtagaa agccacaaaa aagaaattga aatgtgagta gatgctgagt         60
cagaggtttg gtcaatacac aacagctaat tgagataata ttatacacgt cacgatgact        120
tgttttttct cctcccaact tgttaatttc tttattctta aaattaaacc atcgcaaaaa        180
cagaagaaca cagctgtttt tctcgactcc caatttctat tttgctgcta aggacatttc        240
atttcattat ttcccaattc aggactcctt agattttcct aaatttgttt tcctaacttg        300
ctctctctca ttctaacatt ttctcatttt tttagattat cttgtacttt ttagtagatt        360
attttatcag gttttacaaa catacattga cattctaaaa agggcttcta aaaattcagt        420
gtggaatgct gatatactaa aaaaaggtca tgcaaaatta tctacgattt atctaaaatt        480
agataatttg ccatatataa ctattaacta ataatcgatc ctttgatttt ttgttttagat       540 aaaacgaaac agctatatct ttttttttg ttatcggatt ttaatcgaat aaaagctgaa         600
aaataacagt tatatcttct tcttttttaa ctaatgaaac agttatatct taaacaaaca       660
acagaaacag taaatatatta atgcaaatcc gcgtcaagag ataaattta acaaactaat       720 aacaattgag ataagattag cgcaaaagaa actctaattt tagagcgtgt aaacacaaac       780
acgtcttgaa agtaaacgtg aattacacgc ttctaaaacg agcgtgagtt ttggttataa       840
cgaagatacg gtgaagtgtg acacctttct acgttaattt cagtttgagg acacaactca       900
agttatgttt gatatctaag gacttgcact gtctccaaat ctgcaggaag gactttttga       960
ttggatcaat ataaatacca tctccattct cgtctccttc                             1000
```

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115

```
gatcatgatc agtttcaact cgctgtgccc acgtgtcgag agatcggcac gtgcctgagc         60
tctcagccgc tcataaatac acttgtttag tagcaacagt atactatagt agtcctctcc        120
tgtttggctt ttagcttgca tcgatggatg gatggatgga tcgcatgaga gggcttcgcg        180
aaggtacgga accttacaca acgcgtgtcc tttctacgtg gccatcgtgt aggcgtctcg        240
ccatgctacg tgtcccggag gatgtctcga tgccaaccct tataaatact gttccattcc        300
aatcccatcg ccacagccag tgcaaatctg atcgatcaag ataatcgagc a                 351
```

```
<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116
cccgatcggc cttaatctga gtcctaaaaa ctgttatact taacagttaa cgcatgattt      60
gatggaggag ccatagatgc aattcaatca aactgaaatt tctgcaagaa tctcaaacac     120
ggagatctca aagtttgaaa gaaaatttat ttcttcgact caaaacaaac ttacgaaatt     180
taggtagaac ttatatacat tatattgtaa ttttttgtaa caaaatgttt ttattattat     240
tatagaattt tactggttaa attaaaaatg aatagaaaag gtgaattaag aggagagagg     300
aggtaaacat tttcttctat tttttcatat tttcaggata aattattgta aaagtttaca     360
agatttccat ttgactagtg taaatgagga atattctcta gtaagatcat tatttcatct     420
acttctttta tcttctacca gtagaggaat aaacaatatt tagctccttt gtaaatacaa     480
attaattttc gttcttgaca tcattcaatt ttaattttac gtataaaata aaagatcata     540
cctattagaa cgattaagga gaaatacaat tcgaatgaga aggatgtgcc gtttgttata     600
ataaacagcc acacgacgta aacgtaaaat gaccacatga tgggccaata gacatggacc     660
gactactaat aatagtaagt tacattttag gatggaataa atatcatacc gacatcagtt     720
tgaaagaaaa gggaaaaaaa gaaaaaataa ataaaagata tactaccgac atgagttcca     780
aaaagcaaaa aaaagatca agccgacaca gacacgcgta gagagcaaaa tgactttgac     840
gtcacaccac gaaaacagac gcttcatacg tgtcccttta tctctctcag tctctctata     900
aacttagtga gaccctcctc tgttttactc acaaatatgc aaactagaaa acaatcatca     960
ggataaaagg gtttgattac ttctattgga agaaaaaaa tctttggaaa aggcctgcag    1020
gg                                                                  1022

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117
catacttaat tctaaaaaaa caacacttat agtttataag cagctcttat gataaaaatc      60
tttctgagtt atagctctgt taaacttgta ttcaccccaa aaacggatgt ttcatttctt     120
atttttact tggagtattt tattgtaatt tgtaaaaaaa aatgtaaagt gggggatatc     180
atgaaaaaca acgtcacttt gtttggtcac aatatacatt tgataaaata atggtcgtcg     240
cgtgatttag ttgattttg ttttatcaac cacgtgtttc acttgatgag tagtttatat     300
agttaacatg attcggccac ttcagatttg ggtttgccca catatgacat accgacatag     360
aaggttaaat ccacgtggga aatgccaata ttcaatgttt ggttttcaaa agagaatcat     420
ttctttatat gatctcaaaa gtatggaatt gaaatgacta atgagcacat gcaattggtg     480
ctatcttaaa aaccgaacgt ctttgaattt aatttgtttt tcaccaaagg tacctaatga     540
aacccttca ttaaaaaata aaggtaacaa acaaaatttt gtattggaaa aaacatttt     600
tggaatatat aatttggtaa tagaattatg agcaaaaaag aaaagaaaa gaaagaataa     660
```

| | |
|---|---|
| tgagcataat aaagcctttta cagtattact aattgggccg agcagttttg ggctcttgat | 720 |
| catgtctagt aatcttaaac agacgataaa gttaactgca atttagttgg ttcaggtgag | 780 |
| ctaccaaatc caaaaatacg cagattaggt tcaccgtacc ggaacaaacc ggatttatca | 840 |
| aaatccttaa gttatacgaa atcacgcttt tccttcgatt tctccgctct tctccactct | 900 |
| tcttctctgt tctatcgcag acattttgt ttatatgcat acataataat aatacactct | 960 |
| tgtcaggatt tttgattctc tctttggttt tctcggaaaa | 1000 |

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

| | |
|---|---|
| caagtcaagt tccaatattc taaggagaaa taatagtata ctaaacatac attagagagg | 60 |
| ttaaacttct ttttggattt aagtgtgtat gcataggcta tttattctta agtataacta | 120 |
| ttaactgtag ctagatttat acaagaaata cataaaactt tatgcatgtg aggtagccat | 180 |
| gaatatacgt acatgttgca atcgattata catgttgtat ttggatttct ctatacatgt | 240 |
| tttaacttgt cattctctaa gtatatacat accattaata ctgtgggcat gagtttatga | 300 |
| taagactttt cttttggaga ccagttttgt tttccttcc acctatattt gtctataggc | 360 |
| ttcacggtac actagtttac aagtgttttt atatgttcta aataaaattg agattttccg | 420 |
| gaacggtatg atctgtttgc aaataaggac gtatatataa cagtatcaaa tatatttgtt | 480 |
| gttataaggc aataatatat tttctgagat attgcgtgtt acaaaaaaga aatatttgtt | 540 |
| aagaaaaaaa aagatggtcg aaaaagggga gtaggtgggg gcggtcggct tttgattagt | 600 |
| aataaaagaa accacacgag tgacctaccg attcgactca acgagtctac cgagctaaca | 660 |
| cagattcaac tcgctcgagc ttcgttttat gacaagttgg ttttttttttt tttttttaat | 720 |
| ttttcatct tcttgggttt ggttgggtca ctcttcaggt caggtgtgta aaaaagaaag | 780 |
| aaagaaaaga gagattgttg tgttgtaacc cctttgacta aaatctaatg aacttttta | 840 |
| acacaacaaa actccttcag atctgaaagg gttcttcttc tctcttagtc tcttcgtcct | 900 |
| tttattctcc gtcgtcgttt catgatctga ctctctggtc ttctcttctt cttcttcttc | 960 |
| ttctatttt tcttacttcg tcactgttgt gtctgaac | 998 |

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

| | |
|---|---|
| aaaaaggatg ggtaatggga cctatttcc ccaacatccc acatgcacac ttccctctcc | 60 |
| attctctcac atttatttct ttcattctaa tttatccatt ccgtgtgtaa catattcact | 120 |
| aataatctca tctcactaac tcattcattg attgtgatat gtttatctag aattagtgtt | 180 |
| ttaacactgt gtctacatat gatttccttt tcattgtatg tgaacatgtt aactcactaa | 240 |
| tcattttgta ttttcgagtt aacatgagtc tccacttcgg tagactaaag taagatagg | 300 |
| tttgagtata ataaagttta aaatttgctt taaaatcaat atttataaat aagttttat | 360 |

| cataagtgat ttttgtatgt tatattggac cttgtataaa cagactacag aagaaaatta | 420 |
| tttatgagaa cttgtaatgt tagagtggac ctcgtataaa ctaattatgt gggcttttac | 480 |
| cataaactat ttatgaaaat tattatggcc cacaccacta taactaaagc ccacatattt | 540 |
| agcagcccag tttcattgta agagacatgt tcgctctgga actagaattt tctggttttt | 600 |
| gggtatttgt tttcttatgt gtagagaaat gatggtaacg attaaatgtt gtgtattaca | 660 |
| atttacaatg gtaagacgat taatatattt acacacaatt ttgttgttgc tgtaacacgt | 720 |
| tagtgtgtgt gatgatagaa tttcataaag ctttaactac gaggggcaaa atgttaattc | 780 |
| taaatagttg acagcagaaa aagatatgta tacataatat aaggattaaa acgtaaataa | 840 |
| taataaataa ggcgagttaa attaaaaccc tgttaaaacc ctagcttgaa acacatgtat | 900 |
| aaaaacactt gcgagcgcag cttcatcgcc atcgccattc tctctctcat caaaagcttt | 960 |
| tctccttgat tttcgcattc tttagagtct taacgcaaag | 1000 |

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120

| cagccgtaaa tcctccataa atttattttg caagttttgc tcattatata atgagcggaa | 60 |
| tttatgatat aatcgtttgt aataatgtta tgttttgatc aaaatttgaa attaaaagta | 120 |
| ggtgagaact tgttatacag tgtagataag gtggatcttg aatataaaaa taaaatttat | 180 |
| aagatgtatt taaagcagaa aagcataaaa ctttagataa aataatgtaa aaatgtgtta | 240 |
| gcatcaatgt tgggatattg gccgacccga acttaatcaa tgtcggaagc cattacttct | 300 |
| ctcccaaaag acctttttcc ttcggagaac taggaacttc ctcactacct ttcgcttaac | 360 |
| gtgaaagcca taaatttcat atattcataa aaatcagaaa atctaaaact gtttagtatc | 420 |
| acctgttttt ggtatagact attggttttg tgttacttcc taaactatat gatttcgtac | 480 |
| ttcattggat cttatagaga tgaatattcg taaaaagata agttatctgg tgaaacgtta | 540 |
| cttcagtcat gttgggtcta gatttacata ctactatgaa acattttaag ataataatta | 600 |
| tcctagccaa ctatatgttc tatattatgg gccaagaaga tatagaacta aaagttcaga | 660 |
| atttaacgat ataaattact agtatattct aatacttgaa tgattactgt tttagttgtt | 720 |
| tagaataaat agtagcgtgt tggttaagat accatctatc cacatctata tttgtgtggg | 780 |
| ttacataaaa tgtacataat attatataca tatatatgta tatttttgat aaagccatat | 840 |
| attactcctt gacctctgcc cccatttcct tttactataa ataggaatac tcatgatcct | 900 |
| ctaattcagc aatcaacacc aacgaacaca acctttttcca aagccaataa taaaagaaca | 960 |
| aaagctttta gtttcatcaa agacgaagct gccttagaa | 999 |

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

```
aagatagtac agtttcagtg ttttgagaaa aaaagctgaa ctaaaactaa aatgtttaag      60
gacacaatat ttagtttcaa ttagataatt caacagtttg aacaattttt tttttttttt     120
tttgaagtca tttatttata caatgtttta aaacgcatta agcatttagg cagccgacaa     180
acgcctattg tctaactgta aataggcgct tccacttagg ttcatattgc atatttacta     240
tatgtgtata gtgacaaaaa ccaatatttc tcttattttg gatgaaggta tagtagttgt     300
taaatgttca atataattaa gcattaatga caaataaaat aaaattaatt tagttgataa     360
aaagataatc ttataaaaag atcgatgaat agatataatg gtttactgaa ttctatagct     420
cttaccttgc acgactatgt cccaaggaga ggaagtacct taactataat tctgaacata     480
attttgtcta tcttggtgag tattatatga cctaaaccct ttaataagaa aaagtataat     540
actggcgtaa cgtaataaat taacacaatc ataagttgtt gacaagcaaa aaaacataca     600
taatttgttt aatgagatat attagttata gttcttatgt caaagtacaa ttatgcctac     660
caaaattaat taatgatttc aacaggaagt ctgagatgat gggccgacgt gtagttacgt     720
ttcttgaatt gtgagagatg gtatttatta tactgaagaa acattatttt actaaataaa     780
ttttcatttc acatcttctg taatcaatgc gggtagatga agaagttgtt aatacgatgg     840
ccaaccatat ggatctcttt tttggcgttt ctatatatag taacctcgac tccaaaggca     900
ttacgtgact caataaaatc aagtcttttg tttcctttta tccaaaaaaa aaaaaaagtc     960
ttgtgtttct cttaggttgg ttgagaatca tttcatttca                          1000
```

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

```
aattaaatga aaccgcccct aaattaggag ggatttgggt aagtggtaac acattcactg      60
gaaacatgtg aagaaaggag gatgtcaagt agctgaaaac tcagtatagt aaccaacggc     120
ttctcaccaa cctttcatta ataatttggt catccctata ttttttattca acattttgtt     180
tttcaatagc ttagagcacc ttaatacctt tcagtgtttt tttataaaaa aaacaaaaat     240
tgggattaat catcaatccc caaatgtaac gtttacttag attatgttca tttttctata     300
cacacaaatc atattctttt gtttaatct tcgaaaaacg agaggacatt aaatacccct     360
aaaaaggag gggacattac taccaacgta cattaacatg tttgatagca aacgatttat     420
tttgttcgtt ttgaaaaggg gaaagtaatg tgtaaattat gtaaagatta ataaactttt     480
atggtatagt aacattttcg aataataaga gagggaaaac actcgccatt gtcggcaatt     540
tagaaccaat attagaaggg ttttttttaga gaaaaaggac ttaaaagttt agagacctta     600
acaacaactt atttagaaat agacatgctt aagttgacaa cagcgagttt attttctata     660
tcgaagaaaa atacgaactt tttcttaatt agatttcgaa tgcatgcact atcgagaatc     720
gaccgtcaca agaaaaaact aatatacata ctgtacatat ctatattcaa tattggtggg     780
gatgggttta atgtgtattt ataattcatg gataaattca cacaataagg tccatgaaac     840
tagaaggtac caaaaataag cattaatgac tctttgccac ttatatatat gattctctca     900
```

```
tagtaccatt ttattctccc aaacctatct tcttcttcct ctcttgtctc tctcgctctc      960
tctcttctac attgtttctt gaggtcaatc tattaaaa                              998
```

<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123

```
gattgaatga tgagtgtgca cccttgtatt actaataaaa aatttagcaa cagttataag       60
ctaacgtcat ccatgagtca ttcattagat tcactatttg cgttctcaaa aatcgaattg      120
ttaaaatttg agaagctcta atatacgagt caatgagatg tggcaaaagc atgtccttga      180
ccataaaatt tcgaggggtc aactcattag ataaggacaa gaatcaacca attgaaggcg      240
tcttctataa caagtttctt tattactaat attaaagtcc aatggggtga ggggagaag       300 aacttaaata aaaggaaata attggtaagt gaataaaatc taaatacgat actagatgat      360
tgatttgtgc tagtgcatgg tattagatca gatatgtgtt actattcgaa ttcaaattgg      420
catattccat gttgttgata agaaaattgt agaagtgtaa aagctgagtt actatattca      480
aactagtggt ttacataaag tgagacaaca actgtttcac aaaaatgact ataaaatagt      540
aagtagtatt aggtcaattg atttttaaaat tttaatcaaa ttcaaatttg tgatataatc      600
aaatttgttt atagaaaatg ttaagaaatc aattttggca gaactaattc agtgagaaac      660
aatcatttac aaaaacaatt ttaacattat ttaacagtaa gatttgacat ttaacccgtt      720
cgtgtgaacc catcatatct aacatggctc tacccatgac gcctccatgc catggacaat      780
tttgacagat cagaagttct gaacgtggac gaggtaagaa caccatgatg atacgattgg      840
agttagttat gtcgccaccg acatcactgc caatctcatt aataaaagtg gtactaaatc      900
tctaatctct attaactata aatataacaa agaaccaaaa gaaagtttct tatctctctt      960
atctttcata atttccaaga aacacaaacc ttttctacta                           1000
```

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124

```
acgttcagag gcatcgcttt tgtacaaatt gaagcgggtt tgttcaatat ttaaaataac       60
acaggaaaca ttcaaatgta ttattgatgt tgcttaggtt tgtgaaatga tatgaaccat      120
atcgtatata ttactagatt tttcttatat gttttaaggg tagtggggct gacctatcat      180
tctgtttggc attaccaatc agactatcag agtattcacc attcaggatt ccataactag      240
aaaaagaagg ggtttacatt ttctcatact gtataatttt ctactatcag agatttatc       300 gattacatta atctccatagt gattattctg atttataaaa aagttgacaa ataattaaa      360 accagtattt tataacaaga ttgtctctct cccatggcca ttattttgac ctctgactta      420
tttaaatctt aattaacagc ataatactgt attaagcgta tttaaatgaa acaaataaa       480 agaaaaaaag aacaaaacga aagagtggac cacatgcgtg tcaagaaagg ccggtcgtta      540
ccgttaaggt gtgtcgaact gtgattgggc cacgttaacg gcgtatccaa aagaaagaaa      600
```

```
gggcacgtgt atagatctag gaaaaaagaa agaatggacg gtttagattg tatctaggta      660
ccaggaaatg gaacgtcaca ccaaacggta cgtgtcggat cctgcccgtt gatgctgacg      720
gtcagcaact tccccttatt catgccccccc tgcccgttaa ttacgtgtaa cccttccatg     780
cgaaaatcaa accctttttt tttttgcgt tcttcttcaa cttttctttt taaatcaaac       840
cttttctttt taaatcaca ttgcatttcc taacgctcaa caaaatctct ctctactaat       900
atctctctct ctctctctct attgttgaag aagactcata atcggagatt gtttgttttt     960
ggtttgctct gtaaattgga gaagttttgt tagagatcaa                           1000
```

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125

```
aacattttct ttaacttact cttaaatttt aatagtaagt tgatgcatgt tatgttgatc      60
cgtcttgatc acaaatattg ttttatggac gaattctttg acagtaaatg gctatagtga     120
ctcagcttgg agcatcccga tatgaaaaca aagtgcagta ttgtgtcgtg gtcatcacta     180
acgcactttc ctagaactat cgcgcgtgtt tgacctatgc aacacaccag atgtcatgaa     240
cgtatactta aatagaaaca atgatataga caattggcta tattctgtca tggaacgcaa     300
accggataac atgtctatta gattcatcgg acttgatcat ggttatgtct taatagacga    360
attctttgtt aacgattggt taaaacggct cacgttagag catcctacta tgacttcaaa     420
attgataaat attacatgga aatcactttta attttagtta gaaggtagtt aatttagata    480 ttcttatttta ataaattaaa aaatagaaga aaaaagatg agaagagttt tgtttataa     540 aataagaaat atcttttatt gtaattttaa aattaaacaa atttaattta tattaaaatt     600
atctttgttt tattgttaag gcaataatta ttttttttggt gggaattgtt aaaacaataa    660
ttagtatact gttaagtggt cctttaataa taagataacg tgatttaaaa aagaacgaga    720
caggctaata tagtagagag gaaaaaatac aatttaggcc caataaagcc caatatagag    780
ttgtgctcaa acacaggtct tcgccagatt tcctatgacg ccgtgtgtca atcatgacgc     840
caagtgtcat tcaagaccgt cacgtggcgt tgtttctaca cataggcgat ccatacaaat     900
cagtaacaaa cacgaaaaga gcattcatat gtacgaaagt agaaaagaag agactctttg     960
tgataaaact aagtaagaaa tagcataaaa gtaaaaggga                         1000
```

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

```
gtttccaaaa ctagtattct ttatttgctc tattcattat atttttatat ttgtaacgtc      60
ccgaccgtct ttattaggtt tcgacaatca cttctcggaa ggtcgtccat cctgaaatta     120
ctctatccta aacatgttta actataaaat tctctcgaaa cttttgtaac gtatataacc    180
acataaattc tcttaaactt atttgcatac accattatat ttctgaaatc gatatgttac    240
aatattattt aatatttaga ttacttttac tgaatcgaat taaatatcaa atcgaaacaa     300
```

```
atctaatcta ccaaaaataa ttttgttata aacatttctt gcctagttct acctcatata    360
cattttagtt aaagaaagaa atcacaacaa ttcccataat tcaataatta aatccacaaa    420
atcttggagt aagtaagaga aataaaaaga tagtatctta acataaacaa ttcaaagatg    480
ctctctcaca caattcacac acacttacaa aacaaaagac agaaacaatg ttttcattca    540
aatcaaaaga agttataaca ctagtacaaa aaaagctcaa attctaatag taactctttt    600
tatttcccaa ttacccaaag attctctctc acttcacaaa actagctttg agagtcgtgt    660
tccacaaaat ccattaaagc tgaaacggtt ttgctcacca ttcaaacaaa tacaaaattg    720
caaaacccca aattataaca aaataatata aaaattaaac cgctaaaaag agtgaaccaa    780
caaaaatcgc cgaatgtgtg tgtaatgaga aaaccgaccc atcatcccaa tcatctcttc    840
ccgtgtcact ctcttcctct cccacgtttc ttctctcttc cctttatggg ttttaacttc    900
tccttcttct tcttcttcaa tcttcagttt tcaaattcaa caacaattca cattttgatt    960
tcttcatcat ctctctctct ctcgcttctc tctcaaatcg                        1000
```

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127

```
tagtgcgcgt ggggagaggg aatggtgaaa ccttagtggt taagttatga ggaaaatgat     60
aaaaggataa aacaatcaaa tgcagcttga aacggccata acataaagta ccttatggtg    120
gtgcgaatat ttttgtgttt ctttcactct tttattgctg aaagctacga cacttgtctt    180
aatatattgt ttccgcaagt cacatgatct acttttatt taacgtctag aaacgccgag    240
atatatgatg attagtatat cacgtctatg caaattgtta gttcgtgttt ggccaaaaga    300
tatcgagaca tgtctgaaga accgagtctg gttttgagat atttcttcaa gcattactat    360
acaatagaaa aaggagacac gcgaatatga taatagcaaa aggcataaaa aggcgaaaat    420
taaagaaaaa cgtaaagtga tttggcctca atcaacggga acgtatctta attttagagg    480
ttcttctttt acttttgaga cgagagagtt tgcgtctttg cgagctgctt tggttgacta    540
aacattatca tattgaaaac caaaatacaa cggaggaata tttgtcacag tttcactttc    600
acattgtttc cttaacgttt aatcaacctt gttcaaaatt tctatagttg taatcatcat    660
tgtttacaaa attttcgttc aaagatgatt ttaaataaaa ttgtgaaaga aaaccttttc    720
tgaaataagg attggatgat agtgttaaaa gaaaaatatg aactgaggca aaaagaggag    780
tggtccccgg aagattgtga aatgtgtcat ctaaaccagc cagacgtagt cacgtgttct    840
ctctagcttt atgaacttcc ttagccagca ccatcattgt gattgtagta tatatgtaac    900
cctaccttca tctctcccat tttccattct ccatatagac tcctttacaa tatacaaaac    960
ctatccaaaa gcgaagaagc caagcaaaca tattataaaa                        1000
```

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128

```
gtcatatctt atcaacacgt caacgatcaa aacctttagc ctattaaatt caacggctta      60
gatcaaaacg aaactaggtg ggtcccactt ttaatatcgt ggctgcataa catttcctcg     120
ataactgaag ccgttgtggt ctttctcaga atctggtgct taaacactct ggtgagttct     180
agtacttctg ctatgatcga tctcattacc atttcttaaa tttctctccc taaatattcc     240
gagttcttga tttttgataa cttcaggttt tctcttttg ataaatctgg tctttccatt      300
ttttttttt tgtggttaat ttagtttcct atgttcttcg attgtattat gcatgatctg      360
tgtttggatt ctgttagatt atgttattgg tgaatatgta tgtgttttg catgtctggt      420
tttggtctta aaaatgttca atctgatga tttgattgaa gcttttttag tgttggttg       480
attcttctca aaactactgt taatttacta tcatgttttc caactttgat tcatgatgac    540
acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt ttgctgattt gcgactgttt cattttttct    780
caaaattgtt ttttgttaag tttatctaac agttatcgtt gtcaaaagtc tctttcattt    840
tgcaaaatct tctttttttt tttgtttgta acttgtttt ttaagctaca catttagtct     900
gtaaaatagc atcgaggaac agttgtctta gtagacttgc atgttcttgt aacttctatt   960
tgtttcagtt tgttgatgac tgctttgatt ttgtaggtca aa                      1002
```

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

```
tgtggccact aaagatttac ccttaaccgg gcccatataa gcccacgtca agtggcgctt     60
atacgctctc cgtaagagag ccaacatttg gtatgtaatg ttgcaaatta ttcttcaaga   120
caataaattc aaatataatt caatattgtc caaatatagt gatgtacttc agttgtgcac   180
atagaaactc cactaaacca acttttagat agatgcattc acaaattttc aacaatgtcg   240
cgaaagtcta atccatcacc agattctaac attttaatta ttatatttaa ctatacatac   300
tctaatcagc atgagtcaaa cgtgtacaat agcccaagca tataataaga ccaaagtcaa   360
actcaaataa atgtctccaa actcaaaact tgaaaaagac ctaattatta catggtagat   420
atgactttgt cgacaagtaa accaactaat cctcgaagct accttctctt cccagttatt   480
atgtgtgatc gatttataaa tctcttcttc taataacacc tatattttc ttatgatgtg    540
aataaatata aaacttttaa ctttaaaaca tatttatccg aaatattgca cttagatttc   600
aaatagataa ataatagtac tatctaactg atattgaaaa gacctaacac ggaaaacagt   660
tttataaaaa atcccaaatg tgggtaatta tcttgatttc ttgggggaaa cagaaaatgg   720
attaagatta atcggagtcg tgtcaagcag ctcgttaata actgtagcaa gttgactgag   780
taagcatcaa cgtgtcatct ccgtaaagcc cattatttct agtctcgccg cgtcttctct   840
tccacgtagc acttcacttt ttctctcctt ttgtttcctt tggaacacaa acgtttctat   900
```

```
ttataggaat aattacgtcg tccgtatctg tgtcggaaca tagatccaaa ttaaaagcga    960
cttacttaat tacatatcgt tcgtgttttt ttcttcaaaa a                       1001
```

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130

```
tcgattggcc cgatcggccc caaaatcaag ctgagccgct tcaaacttca gcttttgaaa     60 tcaccccaa actcatgtcc tcttatcatt ataactaaag gatctttcat tttatttaac    120
tcatcgtctt gcactaccca acccaaaggt tccaactata cccgaagctt tctaaaggtc    180
caaagacttt tttttcgag ccagactatt caagccaaga aaagccaaac cccacaagcc    240 agtactttc aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaaagaaaaa agaaactgat cgagatagaa    720
cgtttgcagt tttataaaca atttaaaaaa caaaaaaaat taaactcaat gtatttttta    780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                               1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt     60
gatcatttgg aataaaattt ataaaaggaa cgaaagcgcc ttctcacggg tccatccat    120 tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
```

```
tacatgatat ttagttatta tagcgtaatt aactaagata agaaattaac taaagtgata    600
ttctgattat tattatttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900
ctttccctta ctttattgtt gcttttaaac cttcaatttg ctcataaacc aaatatataa    960
tatcaaaaca aacaaacaaa aaatcagaat tcccctaata                         1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg     60
atattttatt ttcttggttt cgtctattgt tgttttttcta tttatggttg ggcttttaga    120
actctggaca ggcccatgtc atatgttttc ccttctcctt atattttca ttttcatt      180 tgttaaatta atgcataata tccaaaaaca atttaaattt ttgaaggaac cctttagtta    240
cggctccgaa gctttcacaa gtgagaatgt gagatcaaag aaggcaaatg gaggatttta    300
aaagttaaaa tcatcttta tctgcaaaag ttgacaattt ttttgtatca aatctaaatc    360
atcaaactct cttaaactac aagagcataa caacctctat gtaatccatg aaataatctg    420
cttgaaggac ataacataaa tcattatggc tagagtgact aacttcaatc aaatcctctt    480
aactctagct cccttacaat ggtatcgtaa aacattatgc attagggatt gttgtcctag    540
gaaaataaaa taaaaatccc cacagaccaa ctaccatttt aacttaaaaa taagcttcgt    600
ccgcgacgaa ttgttttcca tcctaaaaat agaatggtgt aatctgctaa tggtttagtt    660
ccattaactt gcaagttcta ttgaaagcct aaatgtcaat aaagatatta aaattcggag    720
tcaaaagaca aatgaatcaa aagcaacaag acaagtcagc tccattcttc actacccatc    780
ttttacaata aatcatctct cttttcacaa atttcaaact actctcattg ccctttagct    840
ttgttataga gccaacacta cagagagact cacacacttg tttcaataat taaatctgaa    900
tttggctctt cttataaact a                                              921
```

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133

```
aactacaagg gagacataat atcaccatct ggttcctgtt atcatctgaa gatttcttgt     60
tttaccttcc agtgataaaa tgatccttat aatacatata gatatattaa attgctgtat    120
tttaagatta tagatatata aggtacatga gagtgtttat ttaaaaaaat tcacttggaa    180
ttcatgtttt gtgatacgtt agattggaat ccatttggga aaagaagaat catctgttct    240
tatgtctcaa attttgactt cattcacttt tcttcttgtc ttttaagaaa gcttccacaa    300
```

```
tctaactgtt cgatgtgaaa actgagattc gagtaagaaa atgtgaactg tgttatactg    360
ttttttaatt agataattta gattgcactc agataaatta ataacattcc tcgaatactt    420
ttatgtgatt ggatatatta ggtatatctg ccaaccaacc aataaactgc tatgtttaaa    480
caaattaaat aaaattagtat atgtttactc aagaataaag aagatagaaa agaaaattct   540
atatgagcta aatttgctgg aggaggcatc ggacgtgggt accagacctt ccaagcaca    600 cgagtagtgc ttagccatgt catgctaaca tacaccattt ggttcataca aaatccaaat   660
caaaatctat ttttaaaatc ttttgcacac gtctttgaaa aacacctctc atactatagc   720
tacggaagct tcaatttcaa ggtttgtcta aaagctaacg att                      763
```

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134

```
atactggtat gcttaaggtt gaagccaaga tctctgtctt acccaagtaa ccactttcta    60
ttagaaggga tcaacactaa gaatatggag atttaagcct aagggctaag gcggttctca   120
acaatacatg atgtgaatac aatcacagac gatttactga ggtttgttga taagatcttg   180
atcagtctct gcatcatctg ttcaacaatc tcaatctttg actgtttgct ttcggagcca   240
taaacagagg aatcccttat tccctgttat aggagcaata caccaagtat tatttccatg   300
gctgaaattc tcttatggaa acctaattgt tccattgaag ctgtaaaatc gaatctggtg   360
aatattctcg agcaaagccg catgctaatt atgtcaattc agaagagttt gattaggaga   420
ctcgaagcga gtttgatgat cttcttgat gttcaactcc gattgtaagg gtataattga    480
cttttcatgt attacggctc caccacctga cactaaggca ctctttgtcc atctcgttgg   540
tatcatcgga ttcggatggt aaaaataaaa agagcagagg aaacttgtta ctcatgcaag   600
cttctcaggt gccacgtcac tccattacgt gtcatcttca cacaccatct cgctcaaaac   660
cgatctcatt tttcaaacct taaggcaga agcaactgat taagttaaca ctcttgagaa    720
gctctcgatt aagcttgaac ttggaggatc a                                   751
```

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135

```
tctctttaaa tcagttaact aaccgtttat atatttacga taaggtttga agagattatt    60
gataaaataa tacatttcat aatcccgcgt tcaaccgttt aaagtaacat ttaagttgac   120
tatatctaat ttttttttcca ttaaatatgg agctggtaaa ctttatcaac ttctaaaaag  180
tgtaacaaca aaaattaggt caatcacaat tctgttttttt ttattatttt ggattgactt  240
ccaattgcaa atagtcttag tgatcaccat tatcatacat atatacatca gtaggtttc    300 atcatgatat accacaaagt attgacaag ccatatggtt ttggatcaaa aagtcggtcc    360
aaaattaatg tttatgtgc aagaaccgac ccattgtaca cacgtgttaa catcttcaag    420
actttcatct ctattttct tttggtcatt aagataccca ttgatccgaa tctgttacat    480
```

```
tcccacctac ttttttaatt tttactatcc actccaaatt aaacacaacc gatgatttta    540
ataattggaa gcttttaaaa atatttcaaa acaagcctct ttgtgtttgt ctatatatat    600
acacgtaata agaaggtgaa tgaatctcac agcttacttg ttctaaggct tccaataacg    660
aaaacagta                                                           669
```

```
<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136
cgggaaacga caatctgatc tctagtccag tcgattggcc cgatcggccg attataaact     60
tacatgagac aagtataaat aattattata aacttattaa gtttaagatc aaggcttttg    120
tgcaatgtat caatgaatgt tagatgtgat atgatgaaag caatgtttta aacacataca    180
tagtcattga tcggaatgtg tgttattaga aatgcatgcc taagccgata gggttatcta    240
tgtttggtct tggacattat agccaaattt cgaatctaat tcttccaata tatattttt    300 ttttttgct tagggccact actagtattg cttatcaatt ttaagagctc atgaaaatgc    360
aacaatatag tagttgcaaa tccttgtttc aagagaaatc aaagggccac ttgtgaattg    420
aataataata atatttgcaa ataaccttc actaaaccat accaacaaaa ccacacagat    480
ttggcaaaga cataaccttt gggagacgtg aaaaggctca aaatttgaca attgtcctta    540
caaattcgct cattagtgca attgtgagat tgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                      702
```

```
<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137
ttctaggaag actggtcaag ctaagctgtt tctgtttttt gttttttgtac tttacttttt     60 gtttgctagt gggaactggg tttattgggc cttgaagttg ataaagatg aataaaagac    120 atatcgccta aagcccatat gagaagcaga agacaaaaac ctccaacttt ggcataaat    180 tttgattata gttaaaagtc cagacccaat ttggcacctg gcttagttac gattctaagg    240
catgacacct gcctaatatg tttattacag aaaataaaga gaatcagcta ggtgtccctt    300
attgaacaca ttaacaaact ccaacgacac tacgtgtctt cgtgactctt actatatcca    360
aaaacctata gctaaagctg aattttccat gattagtata gtcccaacca aaaaaatact    420
gaagaaggca taagc                                                    435
```

```
<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886
```

-continued

<400> SEQUENCE: 138

| agtgtatttg | aaaacgacat | tgaagaatta | atatatttt | ttttaatttt | agttttttat | 60 |
| agtacaaata | ttaaaacaaa | caatcctacc | atatcataac | atttgtaaat | aacattttaa | 120 |
| gttttgtttt | gagttttaat | taattttcta | tgacaaaaaa | atgaagtcaa | tagactaagt | 180 |
| gaatcatata | gtataaataa | acacaattta | aatagtttca | ataaattta | gaaagaataa | 240 |
| aacaaataga | aatcagaagg | tgtctgtttc | ctcctcgcaa | catacgatca | aagagaaaca | 300 |
| acttgacccct | ttacattgct | caagagctca | tctcttccct | ctacaaaaat | ggccgcacgt | 360 |
| ctccaaccctt | ctcccaactc | cttcttccgc | catcatc | | | 397 |

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139

| agcagaacaa | ctatatttat | tgtgtcacat | aaatctgaga | tcatttataa | ccaccaaaga | 60 |
| acctatacac | agtaaatgac | aaatgtatct | ccctctatct | ctattgccca | tatgtagatg | 120 |
| ctaaagtaag | atttctcttt | tttttaatgt | acttttttt | gtataaagta | tattccataa | 180 |
| gaaaaaggaa | aagcttgttt | atggatcaat | tgaccccaaa | aaaagttttt | agatcaaagc | 240 |
| ccaatataaa | aaaaaacac | agtagtgaca | caaaggaact | taaataaacc | atgaattgat | 300 |
| ctataaacag | tagagatcga | taaggcgaac | attttccatg | tgaagtgtct | tctttcatct | 360 |
| ataatatttt | tgcatccaa | taatttcctc | tataatatca | ttcacataat | tgatagaaac | 420 |
| attatgttag | aattgtccac | atcatttgag | ctgtaatata | ttctgtttta | acaaattata | 480 |
| tggtagttgc | ttaatcttat | gtccatcttc | ttctatgcat | cgttttcgcg | cctagttgtc | 540 |
| cagtccattt | caactaccta | cctctaattc | ttatcttaaa | acaacatttt | ttaatttaag | 600 |
| tattatgctc | aaagactaac | tagatagaaa | accgttatta | aacattaaac | gaattaaaag | 660 |
| tcttacatgg | aaaatgtagg | tttataaacc | acgagttatg | attgacaata | aaaaaaatgc | 720 |
| aaatcatcaa | tcaaaagaga | cttgagtgcg | actctatatc | aaccattgca | attaaaatta | 780 |
| tctatcacaa | aaatttttaga | cagattaagt | taatttagtc | taaattcact | aatttatttt | 840 |
| ctataattag | taattaacta | tatttattta | tttacacatt | ttctgataat | ttagaaattt | 900 |
| gcatgaataa | caaatataag | attttggaaa | ttagtagcaa | atttaattaa | taattatttt | 960 |
| tgcctaaatg | aaccaaacta | taaaacctcc | acatacacca | gtcatcaaat | ttacagagac | 1020 |
| aaca | | | | | | 1024 |

<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140

| ctcgagagat | gaagtcttag | taatgtttga | acaaacaata | atcacgtttt | ccatcaaatt | 60 |
| cgagcattta | agtttatat | tactacatgc | cccaagatga | taccgtccat | ctcatccgaa | 120 |
| aatatttctg | aaattgcgct | aagacaacaa | tgtttgctca | aattcgatca | tttaaagttt | 180 |

| | |
|---|---|
| acaaatctct catcaatctt acaaacttct cacactaaac agaggtacat attttcttat | 240 |
| aaagacaaaa ggttcgaaca gctggcttct caactcgagt tgtttgtcag ggcctctctt | 300 |
| cactaactac aagttggtac ttcaaatatt ggtggctagc ttcacgtgat attgtctaca | 360 |
| aattaaaccc atgaaaaagc tgcattaatt gttccaagtg aaccctgagg agtgtcaata | 420 |
| gtctttgctt tagtgtgatc attaaaccaa atctctaaat tcctaatttg tactaacatt | 480 |
| tggaacgtat ttcctactct ctccctgct ccaactccca aaaataagat tagttagatt | 540 |
| tctataacta atatacatgt atactcccaa aaacagtaaa accatattaa taaagctaat | 600 |
| tttgcataga tttatttcgg taaaccggcg gttcaagttg gggaaaaaaa agacaaacgg | 660 |
| tctaaagtca tccaaagaca aaaaaccaaa gacaagttga gagagacgag accaatcaca | 720 |
| acattgcttc gtagattgcg tgacatcatc cttgacggct actttcattt gtgtcttatt | 780 |
| tggataaaac gcacgtgttt aattcacgaa ccttcatagc aataagaaat ttccattact | 840 |
| ttcatatttt caactttttt tattacccat tacatgctta aaatattaat tcacaagtct | 900 |
| ttgtcaaaat tcaatatttt ccaggttcat gaacccttttt tatctcaatc tactctataa | 960 |
| tatctcccta taaattacaa caaaacctct ttatttttca | 1000 |

<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141

| | |
|---|---|
| gatataagta gaatcatttt ttgccgccgt ttctcgctaa cacaccgaaa actgaatcaa | 60 |
| atctcctagc tcttctacgc aaaatcgagt gcatcgacaa tggcggaacg tggtgtcgaa | 120 |
| cgtggtggag atcgcggcga tttcggacgt ggattcggtg gtcgcggcgg tggaagaggt | 180 |
| ggtccgagag gtcgtggtcg ccgtgcaggt cgtgctccag aggaggagaa atgggtgcca | 240 |
| gtgactaagc ttggtcgtct cgtaaaggaa ggtaagatca caaagattga gcagatctac | 300 |
| ctccattctc tcccagtcaa ggagtaccag atcatagatt tactcgtcgg tccttcattg | 360 |
| aaagacgaag tgatgaaaat catgccggtt caaaaacaaa ccagagccgg tcagagaacg | 420 |
| agattcaagg ccttcatcgt cgtcggagat agtaacggtc acgtcggatt aggagtcaaa | 480 |
| tgctccaagg aagttgcgac ggcgatcaga ggcgcgatca ttctcgcgaa attgtctgtg | 540 |
| gttccgatac gaagaggtta ttggggtaac aagattggaa aaccacatac ggttccgtgt | 600 |
| aaggtaaccg ggaaatgtgg atctgttact gtacgtatgg ttccagctcc gagaggttct | 660 |
| ggtattgtgg cggctagagt tcctaagaag gttcttcaat tcgctggaat tgatgatgtc | 720 |
| tttacttctt ctagaggatc caccaaaact cttggaaact tcgtcaaggt atgtactttc | 780 |
| acaatggctg ttttggtttg atgaactctg aattaggcag tgaaaaagta atcattacca | 840 |
| gttaagtgaa tttatattga agattaggat ttagctgatt gtattggttt gagcatgtga | 900 |
| gtttgtgttt aagattgctt gaattgaaat gctttaggtt gtttgattac gctaaattct | 960 |
| gactaatgta attcaaattg ttgttgtttt tttttggtc | 999 |

<210> SEQ ID NO 142
<211> LENGTH: 1024
<212> TYPE: DNA
<213> ORGANISM: Arabidopsis thaliana

```
<220> FEATURE:
<221> NAME/KEY: misc_feature
<223> OTHER INFORMATION: Ceres Promoter YP0028

<400> SEQUENCE: 142
gtcagtgaag tcgattggta gtacttgaaa cacttggttg gtttcatgta tttggcctat      60
atataaacaa acatcgtaat tatatacgga ttttttttcgg aattttacgc catatctgta    120
agtatatata acatgcatgt cgttttcaaa ttcatatgat gaacgatcca cgtaagtgct    180
actactccta caatattgca tgagagagat atgtatttat aaattttatt ttgaagaaga    240
aataagaggg aaggttactt gggtggatcg atgtgaaaac aaaagaagaa aaagcgaaac    300
ccactaagcc attacatgat atcgaccttc ttatctttt cctctttatt ttattttttct    360 catcttcttt ttgtcaggac tttttctac ttaatgaaac ctccaaacta tctaactaat    420
acactcccat gtagaataaa gaaaattata taagatattg ttgatatttt gtaactagaa    480
aatatatttg ctctgtaatt tttcgtaagt taaatcaaca ttttaaagta gaaacaaata    540
ttactgcaaa aagtaggatc attattttg tccaaaatct cagttagcta tagggttgta    600
gtaaaaacaa aacacattct tgatttgccc caaaaaataa agagagagaa gaatattgtt    660
caaaagtggt ctcttctctc tctaattatg ttttcactaa acccaattag attcaaacag    720
tctacaaagt ccaaaagata aacatgggac aacaattcga tgcaaaaaat cctcttttca    780 tgctctttt ttattctcta gtcttttaaa ttactaataa aaactcacaa atccaccaaa    840
cccattctct acaactcacc ttcatctaga tttacccact cccaccgaga aacacaagaa    900
aaaaaatata catatataaa tatacaagac aacacatgat gctgatgcaa tatacacaac    960
aaagtattaa atcttagata ttgtgggtct ccctttcttc tattcatttt cttattcatt   1020
aaaa                                                                 1024

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143
ccgttcgagt atttgaaaat ttcgggtaca cccgcctaaa taggcggacc ttatctagta      60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagttttt    360 tgttgtcacc aattattttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
```

```
aagttcatca ctggtggaaa atgttaaacc ggttttttct cattttttcc gccatgttaa    840
ccaccggttt aaaaagaccg taacacattg aaagattaat aagggtatat ttgtaattac    900
ggtttgctgg caattttaa ttattatttt aattagagaa aatagagaag ccctatcaat    960
gtacatggta tatatataaa aggcaaaacc ctagaaaacg atactattcg actcagccgt   1020
cctt                                                                1024
```

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144

```
aatctgatct ctagtccagt cgattggtac ttgagggaaa catcatattt ttaaaccttg     60
tctcagtaag ctaacacaca ccccttgtga ttacttatcc atgtttatcc acaagaatgc    120
agttggattg agatattttc ttctttgttg aaatcaggcc tcaaggtgtt catgtggtct    180
gcaaaaaaat tcccaaaaat aaagatagtg acatctgaaa tcgataatgg attagacgaa    240
gagtttcgtg ttattccttg gtatgggcgg gtttggggac agatattttg cacagacga     300 ggactaggcc actgtggtcc tgcagcatta ggtgtcccttcc atgtcctg cattacatttt    360 tattgatgga ttcatcaccc tatctactac aacggctaca caaactatga agagtttgt     420 ttactaataa atgcccaagt gaggggtcga tcgaacccgg gacacgtttt tcagtttacc    480
atatagaatt atccttggaa cccttgatac tccatagaac atcaccacct ctgttgtcat    540
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagttttt ggttgcacac tcgtgtggtt gaagtgtgtg tgagaggtac    720
tatacaatac actctgcttt tgttttgtac ctatctcttt ctcttctcca catatccaag    780
actttgggga taaagctgag atcattggtt gccatttggt tgtgtagaag caatcaccca    840
tttgctttat ccgaggttga taaatttcct cgggttctcc ttctgacacg tatgacaaat    900
tctaatagta tattcctcgt agatattacc tatatattct caatagttgc aggtacttaa    960
ggctttgtct tggcatcctc gtcctcttca gcaaaactcg tctctcttgc actccaaaaa   1020
gcaa                                                               1024
```

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145

```
cttatccttt aacaatgaac aggttttttag aggtagcttg atgattcctg cacatgtgat     60
cttggcttca ggcttaattt tccaggtaaa gcattatgag atactcttat atctcttaca    120
tacttttgag ataatgcaca agaacttcat aactatatgc tttagtttct gcatttgaca    180
ctgccaaatt cattaatctc taatatcttt gttgttgatc tttggtagac atgggtacta    240
gaaaaagcaa actacaccaa ggtaaaatac ttttgtacaa acataaactc gttatcacgg    300
aacatcaatg gagtgtatat ctaacggagt gtagaaacat ttgattattg caggaagcta    360
```

| | |
|---|---|
| tctcaggata ttatcggttt atatggaatc tcttctacgc agagtatctg ttattcccct | 420 |
| tcctctagct ttcaatttca tggtgaggat atgcagtttt cttgtatat cattcttctt | 480 |
| cttctttgta gcttggagtc aaaatcggtt ccttcatgta catacatcaa ggatatgtcc | 540 |
| ttctgaattt ttatatcttg caataaaaat gcttgtacca attgaaacac cagcttttg | 600 |
| agttctatga tcactgactt ggttctaacc aaaaaaaaaa aaatgtttaa tttacatatc | 660 |
| taaaagtagg tttagggaaa cctaaacagt aaaatatttg tatattattc gaatttcact | 720 |
| catcataaaa acttaaattg caccataaaa ttttgtttta ctattaatga tgtaatttgt | 780 |
| gtaacttaag ataaaaataa tattccgtaa gttaaccggc taaaaccacg tataaaccag | 840 |
| ggaacctgtt aaaccggttc tttactggat aaagaaatga aagcccatgt agacagctcc | 900 |
| attagagccc aaaccctaaa tttctcatct atataaaagg agtgacatta gggttttgt | 960 |
| tcgtcctctt aaagcttctc gttttctctg ccgtctctc | 999 |

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146

| | |
|---|---|
| tcgattggga ttactacttc atctagtaag gttctgaaaa cgtttgttgt tgataaggaa | 60 |
| gattcgtctc aggttattac tgttgatctt caaggtttgt gattgtgacg cttatacatg | 120 |
| tgctgaaact gtggtgttta tttattgaaa acaaaaaaaa agtctctctt gtagtttcat | 180 |
| tgtactaaat agaaaacaag aaacgttttt ttctttaatc ttctacattg ataatattgg | 240 |
| atcaaaggat tgtttctgca agacacaaca caaacatact tatactagtt tacttctact | 300 |
| aagtactaac tacataccca tacacacact tgcacctaga ctttacttct agacatcatt | 360 |
| accctaaggt agaaccaagc ttacaagcaa gttttaccga caactcttac attacaactc | 420 |
| tagtctgtag tctttaacgt agacttacta actagtcatt agtggtttaa ttttttaaat | 480 |
| tttcatccat atgttttgt tgtagatata aactaaagtc ggtcacattt ataattgtc | 540 |
| attatgtccg cgtaaaagtc aattcagcta ttggacattt atgaaatgta agattttctc | 600 |
| tctcatttcc ccgtgcgtga agacatgcat tggttttct gtaataatca acaaatccaa | 660 |
| acccctttc gatctttatt tggacattgt tagagacaaa atttctctat agtcttttc | 720 |
| ctaatttgat accatgtttt tgtttctgca caaattact cactggttta actaactatc | 780 |
| cacttattta tgattttacc attaggcgtc agctagccct agtcaaattt gtaaacaagc | 840 |
| caagctatct acataaatcg agatgtcatt aacgttaatc gtcgttaatt cgaatttgaa | 900 |
| aacatagata gctttagcag tacaatgggc aatggtaaga agaatagcaa aaggcccaat | 960 |
| atttggtttg cagaaattaa agccttaaaa aaagcccac agatatttgt caagaaccc | 1020 |
| taat | 1024 |

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147

```
aaagattgag ttgagagaga tggtggagac gcagaacaga caaagggagt ttaccatata    60
gtgctctaaa gggcaatgag attgcagtga tgtggctatc cggggaatca tcgcaggtta   120
ttccttccca tgagcaacaa tcaatggatg ggttccaatt cagaggagaa acagaagaag   180
aaacgtttcc agagaaccac agtagggatt ctcgatcttg cgagttgcag agagcctctg   240
aaactgcaat agaaaggaca ctgatgaaaa gaacacactg aaggagtatg ccaatcatgt   300
gaaaactcag agcttgtatt ggtcttgtgg ttgatgaagt tctcacaaaa cctttggctt   360
tgaatctccc ctcattagtc atggtgagaa caagaacaag acgagaaaca gacaaagaag   420
atgaaaaaac ttgttggcca gtgttgacta aggggggaata gccccagaca taacaaaatt   480
agacttgtcg tacatcttta atattttttt atctgtttct ttgtcctgac gctttcatta   540
ttcctgtgat caattttctc ataccattgg tccatcgtta atcctttctt aatttcattt   600
tctacgtaac atgagaggag accaagtcct atgagaacag ttgacgtaac agtggttgtt   660
aagttaagtt aaaagagga agctagtgag agtgaccgtt aggtagagaa gtgagatctt   720
taaccactct tctttctctc tctctctgct ttttttcgtcg tctttcacat ctactgttcg   780
caaactctct tatgcttcca ataatggtga taccaattga gcttgcagg agaatctcct   840
cttctccaca ctctatcaac tggtcagcca tggaatggtc gtttcagttt caatattcct   900
ggattctttt taaggattcc tgtttctctt ctgttcctgg tatattctta acgacgaaat   960
tagtatcgga tcctggtaat acattttgaa gcttttaagt accattgcac tgggatccaa  1020
caat                                                              1024
```

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148

```
gaggtcagtg agtcgattgg tgcaaaattg aaaaattgaa gggtgaaaca aatttaaaga    60
taatatctat taaatcctct aattttaaaa atttagcaaa aattgtatttt tcttatggat   120
ctgttagttc acacgtatct taattagtac caaatcatat ctaatgatta gtgataaaac   180
tagttagata tctatatgtg tctttaccat ttaacttgaa tccttcttct ttttttacg   240
taaacaactt gaatccttcg ttaatacata aatttaaagc attttttctt taattctatt   300
gatcggtata tatttactat aagttttagc tcatatgcaa tttcaaatga tatgcttta    360
aattttgtct aggtgtgata gttgtatctt taacataaat cttatagcaa aattatactt   420
gatattctaa atttatctat ttgctcttgt gaacctcata ttagtctaga gaaactttga   480
aatcctttca attagttgta tgtccaatac attttttacta acatttatta gtcttttta   540
ttaagattat tgttagaaaa aaaaagattt tttaaaaata aataatatgt tttagataca   600
atgtgagtta ggcttcttat attttaaaaa ataaatttat ttcatactta aaaatagttt   660
ggaatttcaa tttatttggc tgaataccat aaaatatgtc aatttgaacc ttatacccat   720
tgactatttg gtgttagaaa ccctttaaca aaaaaaaact atttggtgtt agatatcaaa   780
ataaaaaaag tttaaccatt ggtttcttat attgaattgg atattgttac atgtattaaa   840
gttttttttgg tttaattttg aaacgttgat agaaactatt aagtttaagt ttggtagtat   900
```

```
atttatttgt ggaaaattta attgccatta aatataacgt caacttttt tggttttttt      960 tgagaagtta cgttgtgatt ttgatttcct atataaagt tagattacgt cattttttaa    1020
```

<210> SEQ ID NO 149
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 149

```
ttcatcttta tatttaagag tttaaaaact gcaacttttg ttttctttc actaagtctt       60 atggccacag ttaattaaaa gcagatgaaa ggtggtccaa tggaaaagga gaatgtgatt     120
gggctagttg ggagagttct gatgtctagt gttgggtaca cgtgtccgtc agttacacat     180
agcattaaat cagacggcat gtcattattc aaatctagtt cacatagtac gactaatagc    240
tgataaatta atgattatac agcatatgaa ttatgaattc aaaaaaaaaa aaaaattgaa    300
aatgttaagg agatgctata ttttacaaaa ttcatcgcaa tgctttctac taatttgcta    360
agtggtcttc tccagttagt cttgtcgatt ccaagcgata ttattaaatc ttgaagcatc    420
gctcaaagca ttatagctta agataaccaa attgttatta aaacaccta gtgaaatttt    480 taaattaaaa caattttgat atctttgtaa tatctaatac tactcttcct gtgtctaaaa    540
ggattaattt tcaaaattt cacacatatt aaaaaaaaaa aaaattact agctaaacaa    600 ttttcaataa tcataaaaca atagtaactt aataatttt ttttattttc aaaatagtcc    660
ttcaagttta caattcattt tagtattata atcaacaaaa tttgtattaa aaagttggaa    720
aattaatctt tgtggaacaa aaaaatctag aaatcatttt ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat atttccat atgaaatccc    960 tatataaacc catcatcatc tcccactttt ttcatatcca                         1000
```

<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150

```
ttctcgttct ctagaatatt gctggaccgg attaggtcaa tattattggg ccagattaga     60
tattgaattg tcgacgttgc ttacgttacg ttatatcttg tttaagaatt aaacctatcg    120
acttagtctt aattaagaaa acattgcctt aaattctctg gtctgcgacc gttttttga    180 ccgttaaccc ctaattaaag aaacaaaata attatagaaa gagcactgaa atgtgattat    240
tttaacagta ctcttatgag aaaattcgta cttttttagtt tttttttttgt acaaatctct    300 aagaaaaaca ctactactaa ttaagaaacg tttcaaacaa tttatttc gttggctcat    360 aatcttcct tctcggtccg ggactaaccg ttggcaaaaa aaaaaaaaaa gttgacaata    420
attattaaag cgtaaatcat acctctcaaa taaaaacttg aatttggaaa caaagacaac    480
taaaaaactc gaatttaaga gaattcctaa aatcaagtga agtatcatca cttggtaaaa    540
tttcataacc gttggcttct atttctatgt gtgccttggt ttgcaggaga taatatttca    600
```

```
tttccaacca atgatattcg tacacatagt caaacaaatg tttgtctttg ttattatatt      660
gagaaagaaa caagaaagag agagagagat agataagacg aaggaagtga agcttccaag      720
cgcccaccgt taaaaatctc gtgtgcaagt ttcaaataca agtggccggt ggtctccata      780
atttgatcgt catccaatta aaaggaaga aaaagcgtgt tttatacaag aaaactcatt       840
aaaatagcaa gtctagaaat atctcaacac taatctacca cgtctattac acacacacac      900
acacacactt gatcttaatt tattttcaag attcaagaaa atacccattc cattaccaca      960
acttgaccac acgcctatat ataaaacata aaagccctttt cccc                      1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat       60
accaaaataa ttaaatgatt ggttagtgcc ttagtggaga cttttttaacc gattctaata     120 gactaatgat gtagctaagc atttatttgg gatcatcact gtttgaaaac gtgaaatgtg     180
ataaaagtta tgaaacgatt aaaatataaa ataaccgtac aaaacattat gtaccgtttt      240
tttctctgtt cttttggcga tttggtttag ttcgttacac tctaaatgtt attgcagata      300
tatatataat gatgcatttg catctgagga acatataatt ccggttaaca cttccaaatc     360
ttatatccgt ctaggtaggg atttttataaa tcatttgtgt catcatgcgt tatgcttgtc    420
ggctttgacc ataacgcaga gatatagaac tagcttttac ttaacttttta gatttattat    480 ttgatctaga gttaagtgga gatatatagt gttttttgtta gattattggt ggatgtgaga    540
gtttgtcttt agtttcaagt tgagaatata aggcaagagg agactctgag gcaatcagag    600
gttttgattg gcaaaatatc caaaaggccc aaaccaagtc gaagcccatc tcgtacaaaa     660
aaagaaagag atctgtaaga aaaaatattc tttgatattc ttacaaaaat aagtgtaaaa     720
cttttattag tcaaaatctt caatctttaa aaactctcat cactcctacg aaagcgcgtg    780
agagttatga gacattcctt aatagcatta ctcacaagtc acaagttcaa aacgtctgac    840
tgaaacagaa acaagccttt gttgaagtct tgaagaagag acattagtac tcgtcgtata   900
gccataaaag gtaatatacg aaatttcttc gctaatctct tcaccttcct ctacgcgttt   960
cactttcact ttataaatcc aaatctccct tcgaaaacat                            1000

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152
gttttgaaga acaatctgga tcgaaatcta acataaggtc atcgtattca agttacgcag      60
tcaaggactt gacatcatcc tactctggtc tgaggttacc acttccaaag atgggatttt    120
tcgactcggt atgcttccta agaaattcgt tttattgaac ctagcaaata tcttgtaatg    180
taagattcct gagatgatga agaaaaaaca aactttttgtt acagcaggag aacggagaga   240
aagaaaacag agaaccaaat gctcttgaag caaacagaag aagaagacac aaatccaaac   300
```

| | |
|---|---|
| ttgagacttc ttctacacca gaaaaccgca gcattctggg acaacgcaaa acacgaaagt | 360 |
| gaaacgggca atgatatata tgtcttgggt gcgttacaag gcatcgtttg caactgttga | 420 |
| gttggataag tcaactgtct tctttteett tggttgtagt agctgcettt ttttteettt | 480 |
| gttgctttaa gaaatagccc gaaaaaaaga atgttctaca tttcggagca gaaaactaac | 540 |
| cgaatgagtt tttggtcgga tcatcggatc gatcagatat attttgagtt acgaactgtt | 600 |
| ataaaaaaag ccataatttt gtgttgagtt tgcaaaatac cttataactt gttatttgag | 660 |
| attgcacctc catatatatt aattcgtaag agtatttatt aagtaagctt tagtataaat | 720 |
| cctttttttcc tttaaagtaa gttaatgttc tactaaataa tagtaaagtt gaagaaccgc | 780 |
| tccgttttta caccatgcac gtgttatcta acaaagaaaa tatggtacac ctaatggcta | 840 |
| atgcaaagga caacacaatg aaactaactt gactctgtgt tatagaaacc catagacatc | 900 |
| tgcatacatc ctagtatttg tataaattgg actcaaattc ctgaggacaa tcatagcaaa | 960 |
| caatcacatc atcgcaatat acataaacaa aagaggaaga aaaa | 1004 |

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153

| | |
|---|---|
| taacaatcct tgggaacatt gcatccatag atatccggtt aagatcgatc tttgaactca | 60 |
| taaaaactag tagattggtt ggttggtttc catgtaccag aaggcttacc ctattagttg | 120 |
| aaagttgaaa ctttgttccc tactcaattc ctagttgtgt aaatgtatgt atatgtaatg | 180 |
| tgtataaaac gtagtactta aatgactagg agtggttctt gagaccgatg agagatggga | 240 |
| gcagaactaa agatgatgac ataattaaga acgaatttga aaggctctta ggtttgaatc | 300 |
| ctattcgaga atgttttttgt caaagatagt ggcgattttg aaccaaagaa aacatttaaa | 360 |
| aaatcagtat ccggttacgt tcatgcaaat agaaagtggg ctaggatctg attgtaattt | 420 |
| tagacttaaa gagtctctta agattcaatc ctggctgtgt acaaaactac aaataatcta | 480 |
| ttttagacta tttgggcctt aactaaactt ccactccatt atttactgag gttagagaat | 540 |
| agacttgcga ataaacacat tccccgagaa atactcatga tcccataatt agtcggaggg | 600 |
| tatgccaatc agatctaaga acacacattc cctcaaattt taatgcacat gtaatcatag | 660 |
| tttagcacaa ttcaaaaata atgtagtatt aaagacagaa atttgtagac tttttttttgg | 720 |
| cgttaaaaga agactaagtt tatacgtaca ttttatttta agtggaaaac cgaaattttc | 780 |
| catcgaaata tatgaattta gtatatatat ttctgcaatg tactattttg ctattttggc | 840 |
| aactttcagt ggactactac tttattacaa tgtgtatgga tgcatgagtt tgagtataca | 900 |
| catgtctaaa tgcatgcttt gtaaaacgta acggaccaca aaagaggatc catacaaata | 960 |
| catctcatag cttcctccat tattttccga cacaaacaga gca | 1003 |

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag    60
tgcaatggta atataaaaca agaaaacaag agattttata ggacaatcac taaatgacat   120
ttaattgatt aaacatttat tcattaataa ttgtatgtta ctaacttcaa catttaataa   180
ttttgtttaa gatacgttta catcagagac tattaatatt tttacaggtt gtaactttaa   240
actttgtctt gaatcgaaca tgactataga ttttgggcaa acttaaagat aacaacattt   300
ccgttttttt tcaaattatt acaaatcaaa ctgatatatt agacacaaca cgattacacg   360
taatgaaaaa agaaaagat aaaagataa aagaagggat cgattctgtt tggtctggtt   420
tagtgagatt caaagttaag ctcttccttt caagacatgc cttcttaaac cgggaatgtg   480
aacgtttgta atgtagtccg tccagttaat gcttccaaca tcaaatccaa attctctctt   540
ctcgtcctct gacatattct ccattaatct ctggggtatt gctgttatca aatctgtaaa   600
agaaaccaaa aaaaaagat gaaactttg cgggtaccgg ttttgtctgc tctaagaatt   660
agaatgttaa tgagttctgt cttaccttcc accatagaaa gtgtatggct cataaatagt   720
agcaaggtgt ttggcttgtt caacagattt cttgcatata aactttagct tctgcatcat   780
cttactatcc actgaactca taccactcat caacccactc cgttcttgag catctctcca   840
caaatgatcc gagaaatcat caacggaatt gaaaagtttc atcaaacgca ccataatagg   900
atcacccttta gagtccatgc atggagatgt tttgtagtgg ttataaagaa gctccgctaa   960
gtcttcgaaa accagcgggt ttatcgccga agaagcgatc tgatacacgt ttatttcagg  1020
ttcc                                                                1024
```

<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

```
cgattggatt tagtctatac attatagggc gcaagtttgt ggatttaaga attatataaa    60
aacttgaaat atatagtttt tatgcattct cctcttgtgt aatacataaa ccaaatatga   120
gataggttaa tctgtatttc agataatatt aaattccaaa caatattttt acttgttata   180
agaaggcaat taatatctct ctgttaatgg caagtggtac caagtagtat taaactatta   240
atgcaatgga agagtactgt tggaaattat aatcctctat cacacattca aacagatctc   300
ctgaaatctt ctcttccaaa cttgtacttc tctgatccaa atgtaggctc caaaatatag   360
acatttacca tttactaagt ccacaactcc tttcttgtct ccttcaaaaa tgactcttgt   420
gtaaccacca tatgactccg acagttcggc attgccatga tgagagctta aaaattcacc   480
ttcctgagca tttcaagtct tcactccctt agcttgacct gaaccaagat aaaatgcctt   540
tgtcgtcccg taatatccat cctgctttgg acggcatcat agttacattc gatccatcct   600
atttacaatg ttattttagt attaaaaaca tgacaataaa tttgttgtta acatattca   660
aatacaatat gattggattt ataagtaatt gtaatatgaa atgtccttag taatatgtta   720
aaaaatacat agatacacac acgtactaaa agaggcaacg cgggagatgt cattagagga   780
agaactagga agcagagcgt tcatgcaaaa tgctaccaaa aacgttaatg caatatctca   840
actaatcagc acagtccatt tcatactgag aatgtaaaaa ccaatcagca tcgtccattt   900
```

```
tttcatctaa ttatttgtta actcttaatt ggccacaact tccaaccaca tgacgctctt      960
tctattccct ttatatattc ccatctcaaa tgttcttgga gacacaaaat atcataaaca     1020
tata                                                                  1024
```

<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156

```
gtcgattgga tgatgaacat tctacatata taattattat gtttaagcac ttagacagca       60
taaattcttt ctaattatat aaatctaacc ttgttacatt gtacatctat aaattacttg      120
aagaaataac gagttctatt tcttttttaaa aattaaaaat actataccat atctcagtga     180
ttaagttgaa ccaaaaggta cggaggagaa acaagcattt gattcttcct tatttttattt    240 tattcatctc tcactaatga tggtggagaa aaaagaaaa tacctaacaa acaaatatat      300
attgtcatac aaaaatattt ctatattttt agttaattag tttatattcc tcacttttca     360
gggcttatat aagaaagtga gcaaacacaa atcaaaatgc agcagcaaat actatcatca     420
cccatctcct tagttctatt ttataattcc tcttctttt gttcatagct ttgtaattat      480
agtcttattt ctctttaagg ctcaataaga ggaggtacta ttactacact tctctctact    540
tttacttgta ttttagcatt aaaatcctaa aatccgtttt aaattcaaaa ataaacttag    600
agatgtttaa tctcgattcg gttttttcggc tttaggagaa taattatatg aaattagtat   660
ggatatcttt actagtttcc attcaaatga ttctgatttc aatctaatac tctcactctt    720 taattaaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggttttttaa aagaaaaatc taaaactgaa ttatatcgtt taaccaagtt   900
gtaaaagtca taaaacgtag tatcttgtaa atcgctcttc cacggtccaa atagacttct   960
agtaataaac aagtaaaaact aattttggtt tcttac                              996
```

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157

```
gtcagtgagt cgattggatc acagtccttt atgataaaac aaactcataa ttattccacc       60
gacaacatgc gttttaaatt attttttctt aaattatatt atattatatt gatatcaacc      120
tagctaaaat aattcggatg gcgaaatcgg acaattttta atagaaaaaa tgggtatgaa      180
gatagtctat gattccgttc ttagcgacta gagggacctg ctcaaatctc ccgggtgata     240
cgcgatgtca agctcaatag aaccccacaa ccgacgagac cgagaaatcc ttgatttggg     300
ctagaagatt ttgaaataaa tttaatatat tctaagtaac ttgcttaaat ttttttttcaa    360 actctaaaga cataactaac ataaagtaaa aaaaaaaaag ttaatacatg ggaagaaaaa     420
aattaaacta atgattagct ctctaacgtg tttaatctcg tatcaagttt ttttttaaaa     480
attatattgc tattaaaaca ttgtactatt gtttctattt tgtttagcta ttattcttgt     540
```

```
gaaatgaaaa gttgtgttta ttcaattact aaatggcaat atttatcttg gaaaactata      600
cctctaattg gattaggccc tagacatcct ctttagctta ttgacgttaa aattattccc      660
aaaactatta aagtttagta gtttgaaaga tgcatcaaga cctactcaga taggtaaaag      720
tagaaaacta cagttagtgt gattatattt taaaatatat aaaacaatct tattaaacta      780
aatattcaag atatatactc aaatggaaga taaaaacatt tagtctgtta ccactaccag      840
cctagctagt cactaatagt cactttggaa ctgagtagat atttgcatct tgagttacca      900
tggactcaaa agtccaaaaa gagaccccga gtgaaaatgc taccaactta ataacaaaga      960
agcatttaca gcggtcaaaa agtatctata aatgtttaca caacagtagt cataagcacc     1020
attg                                                                  1024

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158
taccaaaaat aaggagtttc caaaagatgg ttctgatgag aaacagagcc catccctctc       60
cttttcccct tcccatgaaa gaaatcggat ggtcctcctt caatgtcctc cacctactct      120
tctcttcttt ctttttttct ttcttattat taaccattta attaatttcc ccttcaattt      180
cagtttctag ttctgtaaaa agaaaataca catctcactt atagatatcc atatctattt      240
atatgcatgt atagagaata aaaagtgtg agtttctagg tatgttgagt atgtgctgtt       300
tggacaattg ttagatgatc tgtccatttt tttcttttt cttctgtgta taaatatatt       360
tgagcacaaa gaaaaactaa taaccttctg ttttcagcaa gtagggtctt ataaccttca      420
aagaaatatt ccttcaattg aaaacccata aaccaaaata gatattacaa aaggaaagag      480
agatattttc aagaacaaca taattagaaa agcagaagca gcagttaagt ggtactgaga      540
taaatgatat agtttctctt caagaacagt ttctcattac ccaccttctc cttttttgctg     600 atctatcgta atcttgagaa ctcaggtaag gttgtgaata ttatgcacca ttcattaacc      660
ctaaaaataa gagatttaaa ataaatgttt cttctttctc tgattcttgt gtaaccaatt      720
catgggtttg atatgtttct tggttattgc ttatcaacaa agagatttga tcattataaa      780
gtagattaat aactcttaaa cacacaaagt ttctttattt tttagttaca tccctaattc      840
tagaccagaa catggatttg atctatttct tggttatgta ttcttgatca ggaaaaggga      900
tttgatcatc aagattagcc ttctctctct ctctctagat atctttcttg aatttagaaa      960 tcttttattta attatttggt gatgtcatat ataggatcaa                          1000

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159
tagtttttga tttaatctac gtttttctta atcataaatg ggtaattatt agtttttgca       60
aaatcaaaat ccaaaaattg ttctaaacac tgcaaccatt taaggcctat atcactcaga      120
aaatttctgg tgggagaact aatcgtttgt cctttctaaa tctcacatat tagaatttag      180
```

| | |
|---|---|
| aattagtgtg ctacataaga atattagttc agctcggaac aactattttt tggtaaaaca | 240 |
| gagaacttaa acaaatgcat tattttatca acatgcattt tgaattgaat ataaaatttc | 300 |
| ataattgtaa agacataaat tacataaaat tttacatgaa aaaatagata tagaaagaaa | 360 |
| atgaaactaa ctgatgatat gctctctaaa ttttttaatc tcataacaag aattcaaatt | 420 |
| aattagttca tattttttggt taatataaca tttacctgtc taagttggaa ctttcatttt | 480 |
| tttctgtttt gtttagtcag tattcttaat gtgaaacgga aagttgaatt tattcaaact | 540 |
| taaattcaat agcattaatt aaaggcgaaa gctattatct ctacatgtgg ttcaaactag | 600 |
| acatccaatt taattagctt attgacgttg aaatgtttc caaaactact atagtttggc | 660 |
| aatttgaaag atgcatcaga actactcaga caggtaaaag tagaacctct agctgtgtga | 720 |
| attgtatgtt agtccataaa gaacatcttg taaacttcat acttaagata tatattacaa | 780 |
| tatatacttg aatggtagat aaaaacgatt agtctgattg ctagcatact cacaactatt | 840 |
| tggaaatgag taagatattg gcattctaga gttactacta tggagacaaa agtcgaataa | 900 |
| aagagacctc acgtgaaaat gttacgagct agtaaaaaaa gcatttacac taacggtaaa | 960 |
| aaaagtatct ataaatgttt acacaaggta gtagtcatt | 999 |

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160

| | |
|---|---|
| ttggattttt tttttgttga gtcagcagac catctaatct ctcttttccc accacagcct | 60 |
| gctttctatg aagcatttgg gcttacggtt gtggaatcaa tgacttgtgc actcccaacg | 120 |
| tttgctacct gtcatggtgg acccgcagag attatcgaaa acggagtttc tgggttccac | 180 |
| attgacccat atcatccaga ccaggttgca gctaccttgg tcagcttctt tgagacctgt | 240 |
| aacaccaatc caaatcattg ggttaaaatc tctgaaggag ggctcaagcg aatctatgaa | 300 |
| aggttggccc attctccttg acaggcttaa caatacaact tgtatcgctt caacaagatg | 360 |
| atggcttaat aaggattttt gcatgtatag gtacacatgg aagaagtact cagagagact | 420 |
| gcttaccctg gctggagtct atgcattctg gaaacatgtg tctaagctcg aaaggagaga | 480 |
| aacacgacgt tacctagaga tgttttactc attgaaattt cgtgatttgg ttagtgtaac | 540 |
| ccactgttat tcttttgatg tctacatcta ctttacttac attattcttt tcttcggttt | 600 |
| gcaggccaat tcaatcccgc tggcaacaga tgagaactga tcatgacagg gtaggatttt | 660 |
| atttcctgca cttttcttag atcttttgtt tgtgttatct tgaataaaaaa ttgttgggtt | 720 |
| ttgtttcctt cagtggtttg atttttggact tatttgtgtt aatgttgttt tggctgttct | 780 |
| cttaatatca ataacaaata aatttactgg ttggtatcta agatctaaca atagttacta | 840 |
| tttttagagg taaagacacc aaccttgtta tattggtcag agagctaaaa ccttgacttg | 900 |
| ttgggaaaac aaaactctaa tgacagaaaa tctgacatga tgccttataa ttcacagcct | 960 |
| catgttctac ataaatccta acaatagcac tttgtttct | 999 |

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161

```
gataaactga taatggaaaa gaacaaagaa accagttttt aactatttgc atatgtaatt      60
tatttgttgc aaattatatt tagttaaaat gtttcctcta tttatatata tatatatcag     120
tcaagcacta tgtataagaa atgtcaattt ataaatttt acatgtcctt aacagaaag      180
aaaatgaatt tttacatgtc attcatagag agtcactcgt ttatttctta tatagagaat     240
aacacactca catgcatatg catgcaatat gatacatttt atgacaaaga taatcaacgg     300
aaacggtcaa gacataattt gataaacaac ttgcacgatg cacagatctg atcaaatata     360
taactcttta acatatccaa aatattcaaa aagaaaaact cgatccaaac tagcaacatc     420
acgctcacgc ggtaggctaa aaatttatta atctccaaaa gtctttctta tgaacactgc     480
aaacacaaca acttgaaaag tcatataggt ttagatgatg acgcgtattg gctatcgctt     540
accggagtgg ctcataaata caataaacaa tacgtaaaag tcaaagtcaa atatatttag     600
tcaactataa ccattaatcg ggcaaaacct ttagctgtca aaacaacgtg aaaacgatat     660
ttgtatatat catcaagaat cagtagataa gagaatgatt taatcccctg actattacaa     720
ttttggtgta ataaacagtc tctattggtt tttattcttt gttttaattt ctcatgacct     780
atagagagaa ttaggtagtt tcgaaaattg gctaatcaac ttttgaaaac tactgtctac     840
tttgcttaaa ttctctacac ttagtttcgg ataagataat tgtcggacta atagttaatc     900
ccttgacaat ctttgatatt ataaaaggtt tagttaatct cttctctata taaatattca     960
tacaccagct ttcaaaaata tataatccaa acaccaaaaa caaa                    1004
```

<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162

```
gtggcacatg ctgaaacccc gagcatctct ccggaagaca cgcgtcgttc gctccaaaga      60
aaacagtcac agctgccgga gaatctccgc cgtcttcttc tgccaccgga aaaactctct     120
ccaccacttt cagtgcccac ctcgtgttat atccactgta tcctcgtagc accatatcag     180
cctaataaaa ttttatgtat caaattttaa gacatagccg aaactacact atactagaca     240
ataataatat gatttgtttc ctgaaaaatt atggtttcat gagaaacatt aatcatctat     300
aaaacaaatt agctatggca tcgaagagtt atcaatcaaa actgatgaat ctttacttaa     360
tatatacaac atatctttac cttgcggcgg agaagatcgg cgagagaagc accccagcca     420
ccgtcactaa aggattcttc agtgatgaaa tcaccaaaga gaaaaacctt ccgtctcatc     480
atcttccaca caatcttctt gagaaaatct gagagataag aaaggtgtag tggttttgct     540
gaagtgatcg tgtttgattt agtaaagaaa tgctttattt attgttgggg gaaacataaa     600
taaataaagt aaaagtggat gcactaaatg ctttcacccca ctaatcaccg acctttcatg     660
gtttattgtg aaatacactc atagatagac atacaatacc ttatgtacgt aaataacatt     720
ttatttgtcg acacttatgt aagtaacgca tagattattt tctatgtgat tgccactctc     780
agactctcag tttcaaccaa taataacaat aactacaaca acattaatca taaacatatg     840
```

```
ctctggttta caattaaagc ttagattaag aaactgtaac aacgttacag aaaaaaaatg      900
ttatttacgt tttgtaagat tagtctctag aatcatcacc gttttttata tattaatgat      960
tctttcttat atataaaacc tttctcgaaa tacccatgaa a                         1001
```

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163

```
atacaacaga tggcagatat cgagttaaat acgtgaatca gccgttacga tattttaaaa       60
ctagaaaatt atttaaaaat attgcaaaat accatttaat ttcattgttc ataaaaaaaa      120
gaaattcaaa aacttaaaaa ctgattcaaa aatttggatt aattctcatt aacagtcttc      180
aacactacaa caacatgttt ctaatttatt ttatatttta ataattaaac aatatatacg      240
tctgcacatt gttgctccga cataatctag tataaaaata gttgcagcat atgtgaaaag      300
caagcagcat ttatcactca atactttttaa ttttatctgt tgtatgtatt aaggttttgt      360
agctttaaga aaacgcttat aatataaaat aacttctaaa agatatttca tgcgtataca      420
ataaatattt gtgaaaaaac atttcgaaaa cgtgtacaat atataaacta ttgtgttatc      480
ttttgacatt caaacaaatgt ttgacaatgt aatttatcc atgatatgat tggccaatta      540
gctgcgaggt aaaaatccgt atacgagtaa aagtaagata aaatttcgca agaagatttt      600
tagcaggaaa tctaagacaa gtgtcatgaa cgtgtcaatc aacaaacgaa aaggagaatt      660
atagaatcca gattcgacgt accacattaa taaaatatcaa aacattttat gttattttat      720
ttttgctctg gcagttacac tctttttcat tgctccaata aaaaaatcac tcgcatgcat      780
gcatatatat acaccatagt aaactccgcc tcttcttcat tttaaaagta tcagtttaca      840
ctgacacaat ccttaactat tttcctttgt tcttcttcat ctttattaca catttttttc      900
aaggtaacaa ataatctttt taagtcactt ttatactctt taaatcttag attgatatat      960
gaatgcatgt taatatttca agattatag gtctaccaaa c                         1001
```

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164

```
aaacgttgca agattattga ttgtgagaaa gagtgctcaa ggtagtactg atttctgtaa       60
agctcacggt ggtgggaaac gatgttcttg gggagatggg aaatgtgaga aaatttgcta      120
gaggaaagaa gcggtttatg cgctgcgcat aacactatta tgtctcggga gaacaaagat      180
ggaagcaaga gcggtttgat tggaccggga ctctttagtg gccttgtttt tggctctact      240
tctgatcatt ctcagtctgg agctagcgct gtctctgatt gtactgattc tgttgaacga      300
atacagtttg agaataggca gaagaacaag aagatgatga taccgatgca ggttctagta      360
ccttcatcaa tgaaatctcc aagtaattca catgaaggag aaacaaacat ctatgacttc      420
atggttccgg aggagagagt tcacggcggt gggctagtaa tgtctttact tggtggctcc      480
attgatcgaa actgaaagcc atttatggta aaagtgtcac attctcagca aaaacctgtg      540
```

```
taaagctgta aaatgtgtgg gaatctccga atctgtttgt agccggttac gttatgctgg      600
atcaaaaact caagatttgt tggatattgt tatgctggat cggtggtgaa accacttccc      660
ggttgctaaa taaataaacg ttttttgtttt ataatctttt tcactaaacg gcagtatggg     720
cctttagtgg gcttccttta agcgaccaat acaatcgtcg caccggaatc tactaccatt      780
tataggttta ttcatgtaaa acctcggaaa atttgagagc cacaacggtc aagagacaaa      840
aacaacttga agataaaggg ataaggaagg cttcctacat gatggacaac atttctttcc      900
acacaaattc tcataataaa aatcttataa tacaaatact tacgtcataa tcattcaatc      960
tagtccccat gttttaaggt cctgtttctt gtctgataca aat                        1003

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165
ttggtttgca ttgtgaagat ttgtattaac tatagaacat tgaattgatg gtgttaagtt       60
cttacacaag cgtgcttctc ggtttgaact gtttcttttg tatgttgaat cagagcttag      120
tttataggaa ccagagtatc tacttagtca ttctctgatg ctaagtgcta aggttctacc      180
tagttgccct ctaggccctt atgttattga taacttatga agctatttga acacttgatt      240
cttaggagac ctaagttggt acagccagat agagtgtatg ttcttgttct ctatgtgaca      300
ggatcaagct gccacacata gttcaagggt atgctctgtg tgggtttgct cagattgagg      360
acaaatctat acaaggaagt agagtctttg acattttgat gttgtatgat aagaagaaga      420 aggagagta ataaagaaag agaaaaggga aacagaaaca cgtgggagaa catcccaaag       480
aggaagcaca cgcggatctt catgcaaagc tccccgattc tcccatgtgg tcccttctc      540 cctttgtccc cctcctcttt cttctttttct cattttactc cttttttac cattatacaa      600 cgaatctttt ttatcataat ttttttggttt tggtttattt tccaataaca ctttcttggt     660
tacttcccat tctcactttt tcatataaga aactcacttt gggaaactta tgtttgagaa      720
tgacaagtct ttttagagaa agtgatgtaa caaatctaaa gtgattatat aataaccttg      780
cacaatgttt ttgattttttt gtaagattcg aatattaggt ttattattcg tagggaataa     840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                       1004

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166
ttattagatt aatagattgc attgcattgc ttgtgctttc aatttacaaa ttgtctccca       60
actccatcga cacatctctt tttgtgtata taagattcag acttgttata tttttttat       120 aaatatgtta ttagcatctt aagttaaatt gattttttat atctgcatta aggattacac      180
gactatattt gcgattgtgt gttggttaaa atataattta ggattgtctt taactacatt      240
```

```
taggattata tgactatatt tggttaaata taaaatctag ctgtgattat tagtattcaa    300
aaataagtag cctaaccaat taaaacaacg gctattgggg caaattagaa cattttagtg    360
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt cattttctt gtttaccatt tttagctaaa ttatttacga ttacaaaga     540 tatcaaaagt tggatcataa tacaatttat agacttactg tagaaaattc gtatgtacaa    600
gtacaacaaa ttcttcataa taaattttga aaattctatt acaaatgttg taagaaatag    660
aatttgaaat atatataaac taaggagaaa aaaaagaga acatgcattg ctctagtcag     720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt tttttttct tttgtctgaa tggaacaaaa     900
gcatgcgaca tctctgtgtc tttatcttct ctctcctctt cttgaaaaac tgaaccttta    960
attctttctt cacatctcct ttagctttct gaagctgcta                         1000

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167
gattggtatg aaatttcgga gaccaacaaa aaaaacttta ttgagcttgg agtgaagcta     60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300 attttttgttc ctacgacttt aaacggactt tgcttaagtt gtgtgcatgt aagctcgtcg    360
tccctcgatt gtcatcaaca ttcaccaata tcagcctcta tcacacgagt gaaggtggtg    420
attcggctta atgaaaacag agaaatattt caatatgatt cctattaaat tttaaatctt    480
ttttctcaat ctctagattt tcattaaaag catcatgatt ttttttccact atgttcatat   540 atctctatca cagttttagg tacattgtag aaattggata agatacgtca tacgtctaac    600
atgaatttgg tctagcaagg aaggtttgag ataataagtg aaaagaaaac acaagataat    660
aaattataat ttataaatgc tttatagtat tgaaaaataa gatgattttt tttttttta    720 ataccggatt ggctgatcca cttatgatga ctcaaatgtt attaagtttc aagacaattt    780
atgatgacac aaatcacaat gagtcaatag tagccacgaa gccagaaaaa aaaaatgtac    840 tacaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                  1005

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190
```

```
<400> SEQUENCE: 168
taaatagtga cattggtaag aagaaaaaaa acactattaa atagtgaaaa aatggtttat      60
aactctctta attaacatta cttattattg ctagcaccta aaatctccca caaaatattt     120
gttgtaaaac acaaatttac aaaatgattt tgttttaaa ttagtaacac atgttcatat     180
atacgttaat aagaacatac cctatatgat tttatataaa aaaatttctt tgagacgtct     240 tattctttt tctttaataa tatgcaattg tgagagtttg gatttgaatg gtagcattag      300
aagcaaactt gaaccaaaca tatttcatga agtcaaactt gaaccaatgt gatcactaat     360
cacagtgttc gcagtgtaag gcatcagaaa atagaagaag ggacatagct atgaatcata     420
taatcttgac acatgtttta taggttttag gtgtgtatgc taacaaaaaa tgagacagct     480
ttcttctaat agacttaata tttgggctaa atgtaccaca gttgtgaatt cttacaaaa      540 atgggccgag ctacaaaaaa ctacaggccc actctcaact cttatcaaac gacagcgttt     600 tacttttta aaagcacaca cttttgttt ggtgtcggtg acggtgagtt tcgtccgctc      660
ttcctttaaa ttgaagcaac ggttttgatc cgatcaaatc caacggtgct gattacacaa     720
agcccgagac gaaaacgttg actattaagt taggttttaa tctcagccgt taatctacaa     780
atcaacggtt ccctgtaaaa cgaatcttcc ttccttcttc acttccgcgt cttctctctc     840
aatcacctca aaaaaatcga tttcatcaaa atattcaccc gcccgaattt gactctccga     900
tcatcgtctc cgaatctaga tcgacgagat caaaacccta gaaatctaaa tcggaatgag     960
aaattgattt tgatacgaat tagggatctg tgtgttgagg ac                       1002

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169
agtcgattgg tacactctta atttaattag agtaagagat caacaaaaat atagaatttt      60
ctttatatcg aagtgctacg accttatata tatagaaaaa aaagcatagg tgaatctcta     120
aattgagatt gtgctgtagt aaacatatta agttttagt tttttaaga aatgaatctt      180 tttgttgatt aattcaaact agtagtcatt aagattccgg agattccaat ttagaaaagt     240
caaagattca aagaacaagt ccaggtccac atgttgaatc cgattcatca tccactcatc     300
cttcatatct tcctccaccg tctccgccca aaaaatcaat aacaataaaa atcctaaaa      360 aaacatattt gattttgaaa aaactttatc atatattata ttaattaaat agttatccga     420
tgactcatcc tatggtcagg gccttgctgt ctctgacgtc cttaattatc attatttta     480 aatttgtctc tctcagaaaa ttacgccaca atcttcctct tccctttc cgaaaacagc      540 taatatttgt ggacctaaac taaataacgt agcctctaga ttttatataa ttactaatac     600
tatatgctac tacttgttat tatttactcc aatcatatat gataccaatc aagaatcact     660
acataagtag aaaactttgc aatgagtcca ttaattaaaa ttaagaataa acttaaaatt     720
ttatggtatt ttaagattcc ctttggattg taatgacaag aaatcagcaa attagtcgta     780
actcgtaaga ataaacaaga tcaattttta ctttctttac aaagattccg ttgtaatttt     840
agaaattttt ttttgtcact gtttttttat agattaattt atctgcatca atccgattaa     900
```

```
gaagtgtaca catgggcatc tatatatatc taacaggtaa aacgtgtatg tacatgcata    960
aggttttacg tgcttctata aatatatgtg gcagt                               995

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170
ccagtcgatt ggcgcctcgc atgcctatca tatttaaccg tcaataatgg atttggcggt     60
tttggtaggc cgggtcaacc ggattaaaag aaaacggttt ggagtccttc cttgcaattg    120
aattttcaca cattcgggtt ttgtgatttc tctgtcataa tgggcccggc acatatggtt    180
cataacccat gtgggcctat ggtataattt ttccaattaa aactattgtt aggtcgataa    240
aacaaaaaac aataaaaacg agtggaatac acataccaaa aagaatgtga tgaacattag    300 taatttatt ttgatggtta atgaaaaaca aaataaatgc atcttggcat cttccgttgg     360
aaagcgcaaa tagggcagat tttcagacag atatcactat gatgggggt gagagaaaga    420 aaacgaggcg tacctaatgt aacactactt aattagtcgt tagttatagg acttttttt    480 tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agcccttgt tggtgtatac gtattaattt ttattctttt    660
atcacaagcg atacgtatct aagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa aacccaccat    840
tcaatcttgg taagtaacga aaaaaaaggg aagcaagaag aaccacagaa aaggggggcta    900 acaactagac acgtagatct tcatctgccc gtccatctaa cctaccacac tctcatcttc    960
tttttcccgt gtcagtttgt tatataagct ctcactctcc ggtatatttc cccattgcac   1020
tgga                                                                1024

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca aacataagga gaacctaatt acattattgt tttaatttcg tcaaactggt    180 ttttacctt tagttacata gttgattctt catttgtttt agtagttatg gagcacaata    240
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgagggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
```

| | |
|---|---|
| gatcggacga aaattgtaaa ctagtatagt ttcaaaaact agttgaacag gttatgtacc | 600 |
| ttaaacattt atttcaaact taaacactaa agaacatata tgaatagaag tttatataaa | 660 |
| ttactatata tctaccataa atctcttata attatgatgt cacgatgagg aagtgttgaa | 720 |
| acgttaaaat gccaaaatat aagcatgcga cggaattttg gcagaagatt gtagagttgt | 780 |
| aatctgtcgc aatcattact cgtgctagca tttttcattt tcccttcatt tgtggataac | 840 |
| gcacgatata acattctaca caccaacaag attctataaa aacgcaaagg ttgtctccat | 900 |
| agaatatcgt c | 911 |

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172

| | |
|---|---|
| aaacattaat atgtagtaac tatgggcgta tgctttactt tttaaaatgg gcctatgcta | 60 |
| taattgaatg acaaggatta aacaactaat aaaattgtag atgggttaag atgacttatt | 120 |
| tttttactta ccaatttata aatgggcttc gatgtactga aatatatcgc gcctattaac | 180 |
| gaggccattc aacgaatgtt ttaagggccc tatttcgaca ttttaaagaa cacctaggtc | 240 |
| atcattccag aaatggatat tataggattt agataatttc ccacgtttgg tttatttatc | 300 |
| tatttttga cgttgaccaa cataatcgtg cccaaccgtt tcacgcaacg aatttatata | 360 |
| cgaaatatat atatttttca aattaagata ccacaatcaa aacagctgtt gattaacaaa | 420 |
| gagatttttt ttttttggtt ttgagttaca ataacgttag aggataaggt ttcttgcaac | 480 |
| gattaggaaa tcgtataaaa taaaatatgt tataattaag tgttttattt tataatgagt | 540 |
| attaatataa ataaaacctg caaaggata gggatattga ataataaaga gaaacgaaag | 600 |
| agcaattta cttctttata attgaaatta tgtgaatgtt atgtttacaa tgaatgattc | 660 |
| atcgttctat atattgaagt aaagaatgag tttattgtgc ttgcataatg acgttaactt | 720 |
| cacatataca cttattacat aacatttatc acatgtgcgt cttttttttt ttttactttg | 780 |
| taaaatttcc tcacttttaa gactttata caattacta gtaaaataaa gttgcttggg | 840 |
| gctacaccct ttctccctcc aacaactcta tttatagata acattatatc aaaatcaaaa | 900 |
| catagtccct ttcttctata aaggtttttt cacaaccaaa tttccattat aaatcaaaaa | 960 |
| ataaaaactt aattagtttt tacagaagaa agaaaaca | 999 |

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173

| | |
|---|---|
| gggattatat atgatagacg attgtatttg cgggacattg agatgttttcc gaaaatagtc | 60 |
| atcaaatatc aaaccagaat ttgatgtgaa aacactaatt aaaacatata attgacaact | 120 |
| agactatatc atttgttaag ttgagcgttg aagaaaatg aaagagtgta gactgtagta | 180 |
| cgtatgagtt tcccaaaaga tggtgctgaa atattattgg gaagagactt tggttggttc | 240 |
| ggttgaatga agatttttac ctgccatgtt gatagagaaa ggcaaataaa tgtaggggtc | 300 |

| | |
|---|---|
| gatgtctaac gtaaagactg gatcaaccaa gagtcctcct cctcgtcttc accaaaaaaa | 360 |
| aagagtcctc ctcgtggaaa cttatttctt ctccagccaa gatctcatct catctcttca | 420 |
| ctctatgaaa tataaaggaa tcttatggtt tttctaaaaa ctatagtacg tctatatacc | 480 |
| aaaggaaaca atataaaatc agttaatctg ataaattttg agtaaataat aaagttaact | 540 |
| ttgtacttac ctatatcaaa ctaattcaca aaataaagta ataataacaa agaatttta | 600 |
| gtagatccac aatatacaca cacactatga gaaatcataa tagagaattt taatgatttt | 660 |
| gtctaactca tagcaacaag tcgctttggc cgagtggtta aggcgtgtgc ctgctaagta | 720 |
| catgggctct gcccgcgaga gttcgaatct ctcaggcgac gtttcttttg ttttcggcca | 780 |
| taaggaaaa agcccaatta acacgtctcg cttataagcc cataaagcaa acaatgggct | 840 |
| gtctctgtct cactcacaca cgcgttttcc tactttttga ctattttat aaccggcggg | 900 |
| tctgacttaa ttagggtttt ctttaataat cagacactct ctcactcgtt tcgtcaacat | 960 |
| tgaacacaga caaaaccgcg t | 981 |

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174

| | |
|---|---|
| gaaaacaatc ataggttacg ctattatcat cgaaaggtat gtgatgcata ttcccattga | 60 |
| accagatttc catatatttt atttgtaaag tgataatgaa tcacaagatg attcaatatt | 120 |
| aaaaatgggt aactcacttt gacgtgtagt acgtggaaga atagttagct atcacgcata | 180 |
| catatatcta tgaataagtg tgtatgacat aagaaactaa aatatttacc taaagtccag | 240 |
| ttactcatac tgatttcatg catatatgta ttatttattt attttaata aagaagcgat | 300 |
| tggtgttttc atagaaatca tgatagattg ataggtattt cagttccaca aatctagatc | 360 |
| tgtgtgctat acatgcatgt attaatttt tccccttaaa tcatttcagt tgataatatt | 420 |
| gctctttgtt ccaactttag aaaaggtatg aaccaacctg acgattaaca agtaaacatt | 480 |
| aattaatctt tatatgagat aaaaccgagg atatatatga ttgtgttgct gtctattgat | 540 |
| gatgtgtcga tattatgctt gttgtaccaa tgctcgagcc gagcgtgatc gatgccttga | 600 |
| caaactatat atgtttcccg aattaattaa gttttgtatc ttaattagaa taacattttt | 660 |
| atacaatgta atttctcaag cagacaagat atgtatccta tattaattac tatatatgaa | 720 |
| ttgccgggca cctaccagga tgtttcaaat acgagagccc attagtttcc acgtaaatca | 780 |
| caatgacgcg acaaaatcta gaatcgtgtc aaaactctat caatacaata atatatattt | 840 |
| caagggcaat ttcgacttct cctcaactca atgattcaac gccatgaatc tctatataaa | 900 |
| ggctacaaca ccacaaagga tcatcagtca tcacaaccac attaactctt caccactatc | 960 |
| tctcaatctc tcgtttcatt tcttgacgcg tgaaaa | 996 |

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

```
<400> SEQUENCE: 175 taatttttt attttttggaa ctaacactta ttagtttagg tttccatcac ctatttaatt      60
cgtaattctt atacatgcat ataatagaga tacatatata caaatttatg atcattttg     120 cacaacatgt gatctcattc attagtatgc attatgcgaa aacctcgacg cgcaaaagac    180
acgtaatagc taataatgtt actcatttat aatgattgaa gcaagacgaa aacaacaaca    240
tatatatcaa attgtaaact agatatttct taaaagtgaa aaaaaacaaa gaaatataaa    300
ggacaatttt gagtcagtct cttaatatta aaacatatat acataaataa gcacaaacgt    360
ggttacctgt cttcatgcaa tgtggacttt agtttatcta atcaaaatca aaataaaagg    420
tgtaatagtt ctcgtcattt ttcaaatttt aaaaatcaga accaagtgat ttttgtttga    480
gtattgatcc attgtttaaa caatttaaca cagtatatac gtctcttgag atgttgacat    540
gatgataaaa tacgagatcg tctcttggtt ttcgaatttt gaactttaat agttttcttt    600
tttagggaaa ctttaatagt tgtttatcat aagattagtc acctaatggt tacgttgcag    660
taccgaacca atttttacc cttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgtttc atgagccacc tgccacctca    840
ttcacgtcgg tcattttgtc gtttcacggt tcacgctcta gacacgtgct ctgtccccac    900
catgactttc gctgccgact cgcttcgctt tgcaaactca acatgtgtg tatatgtaag     960 tttcatccta ataagcatct cttaccacat taattaaaaa                         1000

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176
ttagttcatt gaaacgtcaa cttttttactt gcaaccactt tgtaggacca ttaactgcaa    60
aataagaatt ctctaagctt cacaaggggt tcgtttggtg ctataaaaac attgttttaa   120
gaactggttt actggttcta taaatctata aatccaaata tgaagtatgg caataataat   180
aacatgttag cacaaaaaat actcattaaa ttcctaccca aaaaaaatct ttatatgaaa   240
ctaaaactta tatacacaat aatagtgata caaagtaggt cttgatattc aactattcgg   300
gattttctgg tttcgagtaa ttcgtataaa aggtttaaga tctattatgt tcactgaaat   360
cttaactttg ttttgtttcc agttttaact agtagaaatt gaaattttta aaaattgtta   420
cttacaataa aatttgaatc aatatcctta atcaaaggat cttaagacta gcacaattaa   480
aacatataac gtagaatatc tgaaataact cgaaaatatc tgaactaagt tagtagtttt   540
aaaatataat cccggtttgg accgggcagt atgtacttca atacttgtgg gttttgacga   600
ttttggatcg gattgggcgg gccagccaga ttgatctatt acaaatttca cctgtcaacg   660
ctaactccga acttaatcaa agattttgag ctaaggaaaa ctaatcagtg atcacccaaa   720
gaaaacattc gtgaataatt gtttgctttc catggcagca aaacaaatag gacccaaata   780
ggaatgtcaa aaaaaagaaa gacacgaaac gaagtagtat aacgtaacac acaaaaataa   840
actagagata ttaaaaacac atgtccacac atggatacaa gagcatttaa ggagcagaag   900
```

```
gcacgtagtg gttagaaggt atgtgatata attaatcggc ccaaatagat tggtaagtag      960
tagccgtcta tatcatccat actcatcata acttcaacct                          1000
```

<210> SEQ ID NO 177
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

```
aagcacccg taaatgttgt catgtagaag aaactagaaa cgttaaacgc atcaaatcaa       60
gaaattaaat tgaaggtaat ttttaacgcc gcctttcaaa tattcttcct aggagaggct     120
acaagacgcg tatttctttc gaattctcca aaccattacc attttgatat ataataccga    180
catgccgttg ataaagtttg tatgcaaatc gttcattggg tatgagcaaa tgccatccat    240
tggttcttgt aattaaatgg tccaaaaata gtttgttccc actactagtt actaatttgt    300
atcactctgc aaaataatca tgatataaac gtatgtgcta tttctaatta aaactcaaaa    360
gtaatcaatg tacaatgcag agatgaccat aaaagaacat taaaacacta cttccactaa    420
atctatgggg tgccttggca aggcaattga ataaggagaa tgcatcaaga tgatatagaa    480
aatgctattc agtttataac attaatgttt tggcggaaaa ttttctatat attagacctt    540
tctgtaaaaa aaaaaaaatg atgtagaaaa tgctattatg tttcaaaaat ttcgcactag    600
tataatacgg aacattgtag tttacactgc tcattaccat gaaaaccaag gcagtatata    660
ccaacattaa taaactaaat cgcgatttct agcaccccca ttaattaatt ttactattat    720
acattctctt tgcttctcga ataataaaac ttctctatat cattctacat aataaataag    780
aaagaaatcg acaagatcta aatttagatc tattcagctt tttcgcctga gaagccaaaa    840
ttgtgaatag aagaaagcag tcgtcatctt cccacgtttg gacgaaataa acataacaa     900 taataaaata taaatcaaa tatataaatc cctaatttgt ctttattact ccacaatttt      960
ctatgtgtat atatatacccc acctctctct tgtgtatttg                         1000
```

<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

```
tataaaccat tcctataaca ccatatttaa acataacaat gaattgcttg gatttcaaac      60
tttattaaat ttggatttta aattttaatt tgattgaatt atacccccctt aattggataa    120 attcaaatat gtcaactttt tttttgtaag attttttttat ggaaaaaaaa attgattatt    180
cactaaaaag atgacaggtt acttataatt taatatatgt aaaccctaaa aagaagaaaa    240
tagtttctgt tttcactttta ggtcttatta tctaaacttc tttaagaaaa tcgcaataaa    300
ttggtttgag ttctaactttt aaacacatta atatttgtgt gctatttaaa aaataattta    360
caaaaaaaaa aacaaattga cagaaaatat caggttttgt aataagatat ttcctgataa    420
atatttaggg aatataacat atcaaaagat tcaaattctg aaaatcaaga atggtagaca    480
tgtgaaagtt gtcatcaata tggtccactt ttctttgctc tataacccaa aattgaccct    540
gacagtcaac ttgtacacgc ggccaaacct ttttataatc atgctattta tttccttcat    600
```

```
tttttattcta tttgctatct aactgattttt tcattaacat gataccagaa atgaatttag        660
atggattaat tcttttccat ccacgacatc tggaaacact tatctcctaa ttaaccttac          720
ttttttttta gtttgtgtgc tccttcataa aatctatatt gtttaaaaca aaggtcaata          780
aatataaata tggataagta taataaatct ttattggata tttcttttttt taaaaaagaa         840 ataaatcttt tttggatatt ttcgtggcag catcataatg agagactacg tcgaaaccgc          900
tggcaaccac ttttgccgcg tttaatttct ttctgaggct tatataaata gatcaaaggg          960
gaaagtgaga tataatacag acaaaacaag agaaaaga                                  998
```

<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179

```
acaagtacca ttcactttt tactttttcaa tgtatacaat catcatgtga taaaaaaaaa           60
aatgtaacca atcaacacac tgagatacgg ccaaaaaatg gtaatacata aatgtttgta          120
ggttttgtaa tttaaatact ttagttaagt tatgatttta ttattttttgc ttatcactta        180 tacgaaatca tcaatctatt ggtatctctt aatcccgctt tttaatttcc accgcacacg         240
caaatcagca aatggttcca gccacgtgca tgtgaccaca tattgtggtc acagtactcg         300 tcctttttt ttcttttgta atcaataaat ttcaatccta aaacttcaca cattgagcac           360
gtcggcaacg ttagctccta aatcataacg agcaaaaaag ttcaaattag ggtatatgat         420
caattgatca tcactacatg tctacataat taatatgtat tcaaccggtc ggtttgttga        480
tactcatagt taagtatata tgtgctaatt agaattagga tgaatcagtt cttgcaaaca         540
actacggttt catataatat gggagtgtta tgtacaaaat gaaagaggat ggatcattct         600
gagatgttat gggctcccag tcaatcatgt tttgctcgca tatgctatct tttgagtctc         660
ttcctaaact catagaataa gcacgttggt tttttccacc gtcctcctcg tgaacaaaag         720
tacaattaca ttttagcaaa ttgaaaataa ccacgtggat ggaccatatt atatgtgatc        780
atattgcttg tcgtcttcgt ttttcttttaa atgtttacac cactacttcc tgacacgtgt      840
ccctattcac atcatccttg ttatatcgtt ttacttataa aggatcacga acaccaaaac        900
atcaatgtgt acgtcttttg cataagaaga aacagagagc attatcaatt attaacaatt       960
acacaagaca gcgagattgt aaaagagtaa gagagagag                              999
```

<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180

```
cacggtcaaa gtattgctaa catggtcatt acattgaaaa agaaaattaa ttgtctttac            60
tcatgtttat tctatacaaa taaaaatatt aaccaaccat cgcactaaca aaatagaaat          120
cttattctaa tcacttaatt gttgacaatt aaatcattga aaaatacact taaatgtcaa         180
atattcgttt tgcatacttt tcaatttaaa tacatttaaa gttcgacaag ttgcgtttac         240
tatcatagaa aactaaatct cctaccaaag cgaaatgaaa ctactaaagc gacaggcagg        300
```

| | | |
|---|---|---|
| ttacataacc taacaaatct ccacgtgtca attaccaaga gaaaaaaga gaagataagc | 360 | |
| ggaacacgtg gtagcacaaa aaagataatg tgatttaaat taaaaaacaa aaacaaagac | 420 | |
| acgtgacgac ctgacgctgc aacatcccac cttacaacgt aataaccact gaacataaga | 480 | |
| cacgtgtacg atcttgtctt tgttttctcg atgaaaacca cgtgggtgct caaagtcctt | 540 | |
| gggtcagagt cttccatgat tccacgtgtc gttaatgcac caaacaaggg tactttcggt | 600 | |
| attttggctt ccgcaaatta gacaaaacag cttttttgttt gattgatttt tctcttctct | 660 | |
| ttttccatct aaattctctt tgggctctta atttcttttt gagtgttcgt tcgagatttg | 720 | |
| tcggagattt tttcggtaaa tgttgaaatt ttgtgggatt ttttttttatt tctttattaa | 780 | |
| acttttttt attgaattta taaaagggga aggtcgtcat taatcgaaga aatggaatct | 840 | |
| tccaaaattt gatattttgc tgtttttcttg ggatttgaat tgctctttat catcaagaat | 900 | |
| ctgttaaaat ttctaatcta aaatctaagt tgagaaaaag agagatctct aatttaaccg | 960 | |
| gaattaatat tctccgaccg aagttattat gttgcaggct | 1000 | |

<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181

| | | |
|---|---|---|
| tttaaaaaat tggataaaac accgataaaa attcacattt gcaaatttta ttcagtcgga | 60 | |
| atatatattt gaaacaagtt ttgaaatcca ttggacgatt aaaattcatt gttgagagga | 120 | |
| taaatatgga tttgttcatc tgaaccatgt cgttgattag tgattgacta ccatgaaaaa | 180 | |
| tatgttatga aaagtataac aacttttgat aaatcacatt tattaacaat aaatcaagac | 240 | |
| aaaatatgtc aacaataata gtagtagaag atattaattc aaattcatcc gtaacaacaa | 300 | |
| aaaatcatac cacaattaag tgtacagaaa aaccttttgg atatatttat tgtcgctttt | 360 | |
| caatgatttt cgtgaaaagg atatatttgt gtaaaataag aaggatcttg acgggtgtaa | 420 | |
| aaacatgcac aattcttaat ttagaccaat cagaagacaa cacgaacact tctttattat | 480 | |
| aagctattaa acaaaatctt gcctattttg cttagaataa tatgaagagt gactcatcag | 540 | |
| ggagtggaaa atatctcagg atttgctttt agctctaaca tgtcaaacta tctagatgcc | 600 | |
| aacaacacaa agtgcaaatt cttttaatat gaaaacaaca ataatatttc taatagaaaa | 660 | |
| ttaaaagggg aaataaaata tttttttaaa atatacaaaa gaagaaggaa tccatcatca | 720 | |
| aagtttata aaattgtaat ataatacaaa cttgtttgct tccttgtctc tccctctgtc | 780 | |
| tctctcatct ctcctatctt ctccatatat acttcatctt cacacccaaa actccacaca | 840 | |
| aaatatctct ccctctatct gcaaatttttc caaagttgca tcctttcaat ttccactcct | 900 | |
| ctctaatata attcacattt tcccactatt gctgattcat tttttttttgt gaattatttc | 960 | |
| aaacccacat aaaaaaatct ttgtttaaat ttaaaacca | 999 | |

<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182

```
actcaacaat aggacaagcc aaaaaaattc caattattgt gttactctat tcttctaaat      60
ttgaacacta atagactatg acatatgagt atataatgtg aagtcttaag atattttcat     120
gtgggagatg aataggccaa gttggagtct gcaaacaaga agctcttgag ccacgacata     180
agccaagttg atgaccgtaa ttaatgaaac taaatgtgtg tggttatata ttagggaccc     240
atggccatat acacaatttt tgtttctgtc gatagcatgc gtttatatat atttctaaaa     300
aaactaacat atttactgga tttgagttcg aatattgaca ctaatataaa ctacgtacca     360
aactacatat gtttatctat atttgattga tcgaagaatt ctgaactgtt ttagaaaatt     420
tcaatacact taacttcatc ttacaacggt aaaagaaatc accactagac aaacaatgcc     480
tcataatgtc tcgaacccte aaactcaaga gtatacattt tactagatta gagaatttga     540
tatcctcaag ttgccaaaga attggaagct tttgttacca aacttagaaa cagaagaagc     600
cacaaaaaaa gacaagggga gttaaagatt gaagtgatgc atttgtctaa gtgtgaaagg     660
tctcaagtct caactttgaa ccataataac attactcaca ctcccttttt ttttcttttt     720
ttttcccaaa gtacccttt taattccctc tataacccac tcactccatt ccctcttctt     780
gtcactgatt caacacgtgg ccacactgat gggatccacc tttcctctta cccacctccc     840
ggtttatata aacccttcac aacacttcat cgctctcaaa ccaactctct cttctctctt     900
ctctcctctc ttctacaaga agaaaaaaaa cagagccttt acacatctca aaatcgaact     960
tactttaacc accaaatact gattgaacac acttgaaa                            998
```

<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183

```
catagtaaaa gtgaatttaa tcatactaag taaaataaga taaaacatgt tatttgaatt      60
tgaatatcgt gggatgcgta tttcggtatt tgattaaagg tctggaaacc ggagctccta     120
taacccgaat aaaaatgcat aacatgttct tccccaacga ggcgagcggg tcagggcact     180
agggtcattg caggcagctc ataaagtcat gatcatctag gagatcaaat tgtatgtcgg     240
ccttctcaaa attacctcta agaatctcaa acccaatcat agaacctcta aaaagacaaa     300
gtcgtcgctt tagaatgggt tcggtttttg gaaccatatt tcacgtcaat ttaatgttta     360
gtataatttc tgaacaacag aattttggat ttatttgcac gtatacaaat atctaattaa     420
taaggacgac tcgtgactat ccttacatta agtttcactg tcgaaataac atagtacaat     480
acttgtcgtt aatttccacg tctcaagtct ataccgtcat ttacggagaa agaacatctc     540
tgttttttcat ccaaactact attctcactt tgtctatata tttaaaatta agtaaaaaag     600
actcaatagt ccaataaaat gatgaccaaa tgagaagatg gttttgtgcc agattttagg     660
aaaagtgagt caaggtttca catctcaaat ttgactgcat aatcttcgcc attaacaacg     720
gcattatata tgtcaagcca atttttccatg ttgcgtactt ttctattgag gtgaaaatat     780
gggtttgttg attaatcaaa gagtttgcct aactaatata actacgactt tttcagtgac     840
cattccatgt aaactctgct tagtgtttca tttgtcaaca atattgtcgt tactcattaa     900
```

```
atcaaggaaa aatatacaat tgtataattt tcttatattt taaaattaat tttgatgtat      960 tacccctta taaataggct atcgctacaa caccaataac                            1000
```

<210> SEQ ID NO 184
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184

```
tttcgatcct cttcttttt aggtttcttg atttgatgat cgccgccagt agagccgtcg       60
tcggaagttt cagagattaa aaccatcacc gtgtgagttg gtagcgaatt aacggaaagt      120
ctaagtcaag atttttaaa aagaaattta tgtgtgaaaa aagccgttg tgtatattta       180 tataatttag aaaatgtttc atcattttaa ttaaaaaatt aataatttgt agaagaaaga      240
agcatttttt atacataaat catttaccctt ctttactgtg tttttcttca cttacttcat     300
ttttactttt ttacaaaaaa gtgaaaagta aattacgtaa ttggtaacat aaattcactt      360
taaatttgca tatgttttgt tttcttcgga aactatatcg aaaagcaaac ggaaagaact     420
tcacaaaaaa ccctagctaa ctaaagacgc atgtgttctt cttattcttc atatatcctc      480
tgtttcttgt gttctgtttt gagtcttaca ttttcaatat ctgactctga ttactatatc     540
taaaagggaa catgaagaac ttgagaccat gttaaactgt acaatgcctt caaacatggc      600
taactaaaga tacattagat ggctttacag tgtgtaatgc ttattatctt taggttttt      660 aaatcccttg tattaagtta tttaccaaat tatgttcttg tactgcttat tggcttggtt     720
gttgtgtgct ttgtaaacaa cacctttggc tttatttcat cctttgtaaa cctactggtc     780
tttgttcagc tcctcttgga agtgagtttg tatgcctgga acgggtttta atggagtgtt      840
tatcgacaaa aaaaaaatgt agcttttgaa atcacagaga gtagttttat attcaaatta     900
catgcatgca actaagtagc aacaaagttg atatggccga gttggtctaa ggcgccagat      960
taaggttctg gtccgaaagg gcgtgggttc aaatcccact gtcaacattc tcttttctc    1020 aaattaatat ttttctgcct caatggttca ggcccaatta tactagacta ctatcgcgac     1080
taaaataggg actagccgaa ttgatccggc ccagtatcag ttgtgtatca ccacgttatt    1140
tcaaatttca aactaaggga taaagatgtc atttgacata tgagatattt ttttgctcca     1200
ctgagatatt tttctttgtc ccaagataaa atatcttttc tcgcatcgtc gtcttccat     1260 ttgcgcatta aaccaaaaag tgtcacgtga tatgtcccca accactacga attttaacta    1320
cagatttaac catggttaaa ccagaattca cgtaaaccga ctctaaacct agaaaatatc    1380
taaaccttgg ttaatatctc agcccccctta taaataacga gacttcgtct acatcgttct     1440
acacatctca ctgctcacta ctctcactgt aatcccttag atcttctttt caaatttcac     1500
cattgcactg gatg                                                      1514
```

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185

```
gtgggtaaaa gtatccttct ttgtgcattt ggtatttta agcatgtaat aagaaaaacc    60
aaaatagacg gctggtattt aataaaagga gactaatgta tgtatagtat atgatttgtg   120
tggaatataa taaagttgta aaatatagat gtgaagcgag tatctatctt ttgactttca   180
aaggtgatcg atcgtgttct ttgtgatagt tttggtcgtc ggtctacaag tcaacaacca   240
ccttgaagtt ttcgcgtctc ggtttcctct tcgcatctgg tatccaatag catacatata   300
ccagtgcgga aaatggcgaa gactagtggg cttgaaccat aaggtttggc cccaatacgg   360
attccaaaca acaagcctag cgcagtcttt tgggatgcat aagactaaac tgtcgcagtg   420
atagacgtaa gatatatcga cttgattgga atcgtctaag ctaataagtt taccttgacc   480
gtttatagtt gcgtcaacgt ccttatggag attgatgccc atcaaataaa cctgaaaatc   540
catcaccatg accaccataa actcccttgc tgccgctgct ttggcttgag caaggtgttt   600
ccttgtaaag ctccgatctt tggataaagt gttccacttt ttgcaagtag ctctgacccc   660
tctcagagat gtcaccggaa tcttagacag aacctcctct gccaaatcac ttggaagatc   720
ggacaatgtc atcatttttg caggtaattt ctccttcgtt gctgctttgg cttgagcacg   780
gtgcttcttt gtaaagctcc gatctttgga taagagcgga tcggaatcct ctaggaggtg   840
ccagtccctt gacctattaa tttatagaag gttttagtgt attttgttcc aatttcttct   900
ctaacttaac aaataacaac tgcctcatag tcatgggctt caaattttat cgcttggtgt   960
atttcgttat ttgcaaggcc ttggcccatt ttgagcccaa taactaaatc tagccttttc  1020
agaccggaca tgaacttcgc atattggcgt aactgtgcag ttttaccttt ttcggatcag  1080
acaagatcag atttagacca cccaacaata gtcagtcata tttgacaacc taagctagcc  1140
gacactacta aaaagcaaac aaaagaagaa ttctatgttg tcattttacc ggtggcaagt  1200
ggacccttct ataaaagagt aaagagacag cctgtgtgtg tataatctct aattatgttc  1260
accgacacaa tcacacaaac ccttctctaa tcacacaact tcttcatgat ttacgacatt  1320
aattatcatt aactctttaa attcacttta catgctcaaa aatatctaat ttgcagcatt  1380
aatttgagta ccgataacta ttattataat cgtcgtgatt cgcaatcttc ttcattagat  1440
gctgtcaagt tgtactcgca cgcggtggtc cagtgaagca aatccaacgg tttaaaacct  1500
tcttacattt ctagatctaa tctgaaccgt cagatatcta gatctcattg tctgaacaca  1560
gttagatgaa actgggaatg aatctggacg aaattacgat cttacaccaa cccctcgac  1620
gagctcgtat atataaagct tatacgctcc tccttcacct tcgtactact actaccacca  1680
catttctta gctcaacctt cattactaat ctccttttaa ggtatgttca cttttcttcg  1740
attcatactt tctcaagatt cctgcatttc tgtagaattt gaaccaagtg tcgattttg  1800
tttgagagaa gtgttgattt atagatctgg ttattgaatc tagattccaa tttttaattg  1860
attcgagttt gttatgtgtg tttatactac ttctcattga tcttgtttga tttctctgct  1920
ctgtattagg tttctttcgt gaatcagatc ggaa                               1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcctttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc catttttttg tagtcttgct     720
agttgagata ttacctcttc tcttcaaagt atccttgaac gctcaccggt tatgaaatct     780
ctacactata gctctgtagt cttgctagat agttagttct ttagctctct ttttgtagcc     840
tagttctttta gctctccttt tgtagccttg ctacagagta agatgggata ttacctcctt     900
gaacgctctc cggttatgac caatttgttg tagctccttg taagtagaac ttaggataga     960
gtgagtcaac tttaagaaag aacctagtat gtggcataac cagattgcag gctctgtctc    1020
ggctacagta acgtaactct atagctcttt gttttgttca gaaagaacca gtgattggat    1080
gattcgtcct tagaaactgg acctaacaac agtcattggc tttgaaatca agccacaaca    1140
atgcctatat gaaccgtcca tttcatttat ccgtttcaaa ccagcccatt acatttcgtc    1200
ccattgataa ccaaaagcgg ttcaatcaga ttatgtttta attttaccaa attctttatg    1260
aagtttaaat tatactcaca ttaaaaggat tattggataa tgtaaaaatt ctgaacaatt    1320
actgattttg gaaaattaac aaatattctt tgaaatagaa gaaaaagcct ttttcctttt    1380
gacaacaaca tataaaatca tactcccatt aaaaagattt taatgtaaaa ttctgaatat    1440
aagatatttt ttacaacaac aaccaaaaat atttattttt ttccttttt acagcaacaa     1500
gaaggaaaaa cttttttttt tgtcaagaaa aggggagatt atgtaaacag ataaaacagg    1560
gaaaataact aaccgaactc tcttaattaa catcttcaaa taaggaaaat tatgatccgc    1620
atatttagga agatcaatgc attaaaacaa cttgcacgtg gaaagagaga ctatacgctc    1680
cacacaagtt gcactaatgg tacctctcac aaaccaatca aaatactgaa taatgccaac    1740
gtgtacaaat tagggtttta cctcacaacc atcgaacatt ctcgaaacat tttaaacagc    1800
ctggcgccat agatctaaac tctcatcgac caattttttga ccgtccgatg gaaactctag    1860
cctcaaccca aaactctata taagaaatc ttttccttcg ttattgctta ccaaatacaa    1920
accctagccg ccttattcgt cttcttcgtt ctctagtttt ttcctcagtc tctgttctta    1980
gatcccttgt agtttccaaa tcttccgata aggcct                               2016
```

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187

```
acagttttct tttctcatct tacaacaagt ttccaggagg atagagacat aaacgaagct    60
cggattgtat cgttctttt agcttttatt cacatccgaa agtcctgtag tttagattct   120
gttatcttgc ggttttgagt taatcagaaa cagagtaatc aatgtaatgt tgcaggctag   180
atctttcatc tttggaaatt tgttttttc tcatgcaatt tctttagctt gaccatgagt   240
gactaaaaga tcaatcagta gcaatgattt gatttggcta agagacattt gtccacttgg   300
catcttgatt tggatggtta caacttgcaa gacccaattg gatacttgct atgacaactc   360
caactcaaga gtgtcgtgta actaagaacc ttgactaatt tgtaatttca atcccaagtc   420
atgttactat atgttttttt gtttgtatta ttttctctcc tacaattaag ctctttgacg   480
tacgtaatct ccggaaccaa ctcctatatc caccatttac tccacgttgt ctccaattat   540
tggacgttga aacttgacac aacgtaaacg tatctacgtg gttgattgta tgtacatatg   600
tacaaacgta caccttttctc ctctttcact tcatcacttg gcttgtgaat tcattaattc   660
ctgcgaa                                                             667
```

<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188

```
gcctctcgac cacgagttta gcacttgtgc aacatatatg cgtgcgatga acatctactg    60
atgcgccatg cgaattttag cgttcgttca tgacgcttcc aacggcacag aggctgagca   120
gcagcatgca tgcatggctc ttgtgaaaac aaaaaaggtt actggtaaat gacatgctgc   180
tgtagctagc tagcagaatg caaggcccat gcatatgcaa tgctatgcga caagtacagt   240
accagcatgt atggtagcca gctaactaat ctatcagcag aggcagcaag ctcgtgcatg   300
gtgtgatgca cttctctcca gtaatctagt ggtaattttc acccaaagcg ttgctcatat   360
ggacagtaat tagtaatatt accaaggttc acaatcccgt tacctgacca aatactactc   420
acgaatggta tctctggttt tcgttaaaac cgttggtaaa ccagcaaaaa tagacaaaat   480
ttgtcaaaat tttaaatttt agttttttt ttttaactta gccgggaaac cttgaagttt   540
gtgctgtcga gctgtcctgg gaaggacggt tttggttggg attgtgaacc ctggttactg   600
cacttcattt ttgaacagat attagtgcaa cagacaaatg ccaacgcatt ttttctgtt   660
taccggcaag ctgaagcttt tacgatcccc atacagccgt tgctgcaaac ctgccaagaa   720
agagcagcag aaacaggtgt cattttgtgg tggaaagcca agtaaagtaa acagaagatg   780
gaagatagtg aggaccaggg agtgaggcag gggacacatg gcccacgcct ccctgcacat   840
tttcgtgtat aaatacaggt ggatgcatcg ctctcccagc atccatcggt tctctgctct   900
gttcatccat agagttctt cctcttctcc tttagtgcaa ggtagagaag agcatgtgtg   960
tgtgtgtgtg tgtgtgaact gtgaagtgca gagtgcttct gtagttctgt gttatgtcca  1020
tagtgatctt gttaggattg ttgctatgga tgcatgatgt tatggttgat ctctgaatta  1080
cagtagggac ttttctgaga tctctggatt agtgggggt gctaaatttt tttctggttg  1140
catcagcttg ggtttctggt attggtgtgg gttcttgctc tgaattttgg ttcagaatgt  1200
cgatttgttt gtgtttgttc tctgaagttg agagtagcta tgatccatcc agcacagaac  1260
```

-continued

| | |
|---|---|
| tgcaggtcct gcctgccggc tgcatataca ggacatgcca ttttgcaagc tctgggctta | 1320 |
| tggtttctct tttggagttc ttcttcttgc atgatctgtg ttctctaaca aaggaagcaa | 1380 |
| gatttagcaa ctttattcag agacaagaaa aggatctggc aaccttttgt ttctgtttta | 1440 |
| tcctactcgt aaagattgtt atttaagcaa aaatttccca aaagttttaa atataatttc | 1500 |
| catgatgtgc cactctcatg tccttgaacc tggcactcat tatgggctcc tcagaagtgc | 1560 |
| tgtagctaat gtcactaatc ttttgtatct ttgttcatag tcttgtattt tatgatgctt | 1620 |
| atccctttgt gctttccatg tttgatgtcc aaatgtcatg gcaatgtttt tgacttctag | 1680 |
| taggggtttt agtaccttt tgttagataa gtacatccaa attctgttta tttattcaaa | 1740 |
| aatcattctg tttattcact gaaaacattt gtccattcaa tggactcata aactgtctgt | 1800 |
| gtttttcagg cttgaggatc catctagaag atagca | 1836 |

<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189

| | |
|---|---|
| gcttaacaca tgaactacca aaatatactg atcactttgt tctagtcata catacCttaa | 60 |
| gtcattttat tctgcagtgt ttggattgga gggagcattc tagcatccct tgggtcgttc | 120 |
| cagcaaatgt ggttctccaa agcagagtaa gcacaacaca gtattttagg ttatgtttcc | 180 |
| cctatctcgt cacggacagc tcacaagtta atgtgattta tctcactata gatacgaaga | 240 |
| acatggagta tcctacatcc aaaggaagtg cccatgaagt tgtggagcat cgctacgatt | 300 |
| tgtgaccaaa tttgggtgca tgtgggcaat cgtattacag ccaccctgtt gttgatctat | 360 |
| atcgactatt atccgacgat atttatcatt atattatgac tagttagttt gtagattttg | 420 |
| agagggcaac ataagaagca atccagctta acctgttatg ttcttgatgg tagattctag | 480 |
| ttcatgtgtt gaatctgttc tccctgctgt agaatgtatc gagttgctgc tctctactct | 540 |
| gtacttttag aataccttt caatcatttg gagtcagctg attgttgtac tacttatacg | 600 |
| ccacctgatt agtcatgtca acaattaaac ttgagcactg gttaagttaa gagtggcctg | 660 |
| attgtagttg ataatcacat tttattcgta gacattgtat gctggatctt tatcagccac | 720 |
| cgtcagatca tcctctgtaa taaatcttca tcagacgtgt gtgccaatcg caaggaacac | 780 |
| gaaatgcatc cgaaatgtta ctctgagtta atcaatacta taattcttgg tcaaattaat | 840 |
| tatttatatc tataaagttt aaattaaatt taggaaaatg aattcatgca aatcttgtgg | 900 |
| taagttgtca atttcataaa aaatccagct tactactccc tttttaggag tgtgttgtgg | 960 |
| ctgcacactt ctgccttttg atatatacgg ttctattctc ggtgtactcc tttattatta | 1020 |
| ttaaaacaat cccagttact tggtaagtgc taatcacgaa tcaaagtcaa cataacaaat | 1080 |
| catgtgcgta cagctataac tcgattacac aaacaacaaa attcatattt gaacataaat | 1140 |
| ccagttgtag catatctggt agtataaagt ttttttttg tatagaagag ttttaatttc | 1200 |
| tgtaagtttt ggaaagcatt taatcctaga aattgtagtg tagctcaact aaaaaataaa | 1260 |
| tgaacttgaa tcgaaattgg gttgtatcat aaatctttac cactcaaacg aatatttatc | 1320 |
| ctaaaccaca aatgactctt ttcatcaagg aatgtttgt tttcagcatt ttaaaaaaaa | 1380 |
| acttttctaa tatggttttc atgtttcgtt cttttgaaat ttaacatcta tttaatttgc | 1440 |

```
acggctccat aaattcaacg gatacatatt ctgaataatt actaaggagg catatatcgg   1500
ctctcttaat acaaccgctt gtttctcaaa atttattttg agttttgtct acacattctc   1560
aaggacggta caaacacact atagatgttc acaattttt ttttctaaag ttgattgatg    1620
gacaaatgtt tgaacatata acatataag cactgaatat ttgcttatgc aggaggtatt    1680
tatatcaagt tcgatacttt actaccatag tccctaggac actaaaatgc cttcaatgat   1740
ctgatgaagc ctaagagaga atattgatca gtggagcgac ttgcaactac acatggcaca   1800
agtagactag acacggtata tattcatatt aacttgttaa aatttactac ttaacagtt    1860 cacttgtggt gcatccatat caattcttac ttacacaata tttgtaaaaa caacctaaca   1920
ctataggatg acctagacaa cctttatgtc aatcacactt agaagatgat cgtcttttta   1980
ataaataatg tgtactacac accatgctct ccatatagat caagatctac aaacccttcc   2040
acttataaac cttaccacca aaactcatt aagttgcttc atttatctat gctattaaga    2100
aaaaaactta tttcgtttat gccatttcta gaaatggcta gtcacactat tcacaatatt   2160
atataataaa taaagtttc aaatattcat ccaccaaaaa tcatcaagtc gtgggactta    2220
tatgttaatt agagaagtcc ctttgggtgc aatcgatttt ggaaaccctta aattttttct   2280 atacatagaa gagagagatg tctagttgca attgcttttg cgatgtgcca accacccttc   2340
tagctttcat ccacgtctac ttaattgcca ttcttcttct tctttttctt cactattact   2400
acctcctatc ttagcgaatc ttcttcttct tcactattac tacctcccac ttagtgaat    2460 tcatcctcat tgttcacaat gacattgcta agttaactag gtatgctaag tacacaatta   2520
gaatataacc tagagccttt gtttccatca tacttaaaag atgacatttt tatatagata   2580
aagtgtgcta ctcacaaggc ttactatata tatgtatgat acacacaaac tccacaaccc   2640
aaaactcttt caagttgtgt ggcccatcta tgctattaaa aagcccattt agcccatcca   2700
acatgagaaa ccctagggtt ttttccctat aaaagatacc taggttattg ttgcttttcc   2760
accccgcccg ccgccgctcc ctattcctat ttaatcccat ctctcttcct catcaccgct   2820
ctcctctctc caggcaagag gtacgcactt tttgtttcgg atttgaaatc tttgcttcgt   2880
tttactatca ttggtcataa gttctttttt gaagatgttt gagaataagt ttatcattga   2940
gattatcgtc acttgtgata ggaagtacgc aacctcaagc cggacaagac gtgagcaaag   3000
```

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

```
gagagcagaa catagtagcc gctgttttct gggggtgcaa tttgtgcaag atcgctatcc     60
ttatggacca tgcaagcacc aagcaatatt aagccaggtc caacagcggt cttggggaat    120
tcagaaatga gcttaaaaac ctccttgagc tggccagctc agccaaggag gtccatcatg    180
catgtgcatg ctcaatactt ggaattattg caaaatgatc ggtcattgac tggaagactt    240 tgcgccctt  ctcagccaac cttatgtggc tgcatgcata gagtaccaac aggaaggtag    300
cgtttgttgg aataaggttt gcatccagca tgtccttgta gagcttcaaa gcctcagcac    360
cttggcccat gaaggccata tccagctaat tgcattccat gagaccacat tcttgctatc    420
catactgttg aagtgaagat gctccgagct tcggaaatgc ttccacacta tgcatacatg    480
```

```
tcaatgagca ctgtcatgac ataaacattg gccccaagt cctcctcagc gataatccta    540
tgcagccact ttcccaggga caaagctcca agctgtgcac acgctgaaag agagctagaa    600
atgatgattg gatttggtca cacgctaagt accagcattt gctcaaagag ggcaattgcc    660
atctccgtcc agccattcta ggcataccct ggtattattg ctttccatga ttccgattcc    720
gtggtcttct atggcatcgc attgaaggcc ttccttgcag actccatatc atttaaccta    780
cagtacaata tggtaattgc tgtcgacact ggagaattcg cagtaaatcc agacttgaga    840
ggaccatgta agcattgatc aagcagttca ttcccaaaca gactatacgg gatcagtgcc    900
agtgctcgag tttggcttca attccaaggc catcaaccca ataaacagat taactgatga    960
accaaccatg caattcgccg agcaaacata gattaagcat tgtaggcaac caaatctgga   1020
ttctccatca agtcaaagag acgccatgca gaattccaca tccccgctgt atacaccgag   1080
atcaaccggt cagaacatgc tcatactccg ccaaccctct cttcagaaca tgctcatact   1140
ccgccaaccc tctcttctct gcaagaggca tcctccccaa ttccccattg ttatatctgt   1200
tgctggtaag accgttgcca gcgtggttgt gtcagaccga acagactctg cactcgccat   1260
cctcacgaac gactccaggg cctccgaacc aggaagcccg gccggccatc agcgtgttcc   1320
acataacggt atccggcgac tgcacagtgt cgaacacctt gcgtgcgtgg tcacctctgg   1380
acagcatgaa gcgtacaggc tacagcttgg ccaatgcgga cgccacgaac gtgtcggcgg   1440
cgtaacccgc gcgtgcagcg cgccgcgcgc gggctgcgga gtcggttgga gacgacgc     1500 cgccgccatg agagcaatga gcgaggtggc ggcgaaggcg aaggagaagt agtcgaggca   1560
agcggaagag aaggcggcag cggagaaagc gatcggggcg gcggaggagg tgggtgggag   1620
ggagggacgc gtagcggagg tcggaggagg agggagctga ggtttccggg gcggggtcg    1680 agagggtagt gtacggaggc gagggacacg gcgaggatct ggtcgaggta gcgcagtgtg   1740
aaggaaagcg cgatgaggcg gagggcgccg gcgaagagcg gcgcggcgga tagcgggagg   1800
aggcggcgcc ggcggggtct catccgattg gaaacagatt gggaaggggg agggggtagg   1860
aatacgtggc gtcggcagta ttaggtagag agagaaaccc tttccatcct ttgtctctta   1920
gccccgaagg agagagaaaa atcagaaaaa aaaaaccctc cgcgtgtggg ggaagcagag   1980
ctccggacgc tggcgccgct cgcgccaccg cacccgcacc gcc                     2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc     60
cacgaagaac gttacacaat cgagtacaaa atctataaga gcaagtttaa tagcatagcc    120
aaatactacc tctaaatcat ctatagccaa tttaatagtt catttattca ataattactt    180
ataaacatat actacaatca ttaatatatg gtcttacttc ttatacacat aatattttgg    240
agtccgtgtt acagctggct ataaatataa gggattttgg ttggatgtgg tacatcctat    300
tataatgaat ctagacatga aacctgtcca aattcatcgt gctaggatac gccacatcta    360
accaaaatct cttatcttta gggatggaga gagtaataat taaatgaagc taggtagagt    420
ttcccggtca atacgcttgc gtgtgcttat aagagcatgg ccaacagttt cccgatactc    480
```

```
ttcccaatat cagtttttgag gagttttgtt ggaaaaaatc gctccaacag tagacctaaa        540 tcaccccctaa aagcttggcg tttccaaacc cgcatatttc gttctccact tgtagggaag       600
agactcggcg cccaatcctt caaccgcatg cacttcgcgc gcgctgtgtg aaaatttttcc      660 taccaggttc ttctttgtgc gttcgtctac ctgtgagtca atccatcacg ccagcagcct       720
catcttcccc gcagctgtct gggaaagcag ccatggctcc cccaagcttc cccagcgtcg       780 acatttttttt ctcagcggca gcgccagacc catctccaac ccaattgggc ggaccttcgt     840
cggcgctccc ccagcaccac caccgactcg aatcggccgt cgcccctatt catctccaat      900
cgtccctcga ccctaccgca tcctgcagca cagcctgtct ctcgcgtcag actggcgctg     960
cgctcccccc ggtaatgtgc aggcgacaaa ggccccatgc gatgcgacca gcagccggcg     1020
acaaccggag gtgcccagtc gctggccttc atcgaatcat cgtgcacctc ggtcggagtc     1080
gatttctgat tgttgctgct gctcaaatct ggagcttgct attgctgaga actgcttggt     1140
ggtggtactg gaaatttgtt gtttgctggc tgatgaaaac tgttgttctt tgctgctaaa     1200
aactgctgct tgctagtact gaaaagtact attgcagctg ctgaaatatc ttgctgcttg     1260
ctgctgaaaa cttcaagttg ttaacaccgt tcacactaaa aaagctgaaa tttttttttct     1320 gggctgaaaa ccccattgtt gatgattgca gaaccaatat ttttccatgt aaaatacagg      1380
agatcgtggt aataatcaag tgaaatatca ttttggggca aatactcaga tcgtacctga     1440
agccaatgga aacattgttc aatgcttaaa ctgtcagtta tgatgtcaaa gagattgatc     1500
actgaatgtc ctgaaaggag ccgtgaggag gatgcagcat tgcagcgtgc gcgagcgtga      1560
gtggaggaga ggaatgacga ttctgttggt agttgtcgat gtggcctact ttttttgttt      1620
tgaggattaa attttgggaa tctcttggag ataaaaggta ttctcatacc ttaaatcctt      1680
tttagagatc taaaaaaaat gatttagggg attgaatttt gggtggctgt tggtgatgct     1740
ctaagttgca catcctgggg aaaaacctcc ctaatccatc agcaaaccga tcaaccaccc     1800
acgacaagtc gacgccaccg ttttttttttt ctccctccta agtcctaacc ccacaaaaat    1860
cccgcgaact ttcgtctcac cacgcgccgc gtgccccta caaataccaa acaacaccca      1920
ccacgtccac tcacaaacca cgcaggaaac ctcagaaaat caccgtacgc gacgcgggcc     1980
caagaaaacc ccgacagaaa ccgcgcagca gcaacaccac caccggcgtc ggag           2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat        60
ctgacttgtg gtggttggac ggccacgtgt taaaaaggg aaacgtccgc atcaccccgat      120 gctgggacat ttgcaatttc gatccagctg tagattgacc agttgttact ctctttttttt    180 taacaccata caaacgtaat actccctctg tcccaaaata taagtatttt ttttaacctc     240
ggttcagtct tcgaggtgct actttgacca ataatatttta taaaaataag atgttttaaa     300
taaagagagt tgcatattat gatagctcgt ttaatgataa acaaagtacc atcaaattta    360
catgattaat ctttttaatt tatttgctat taatagttaa aatttaaaaa gtttgacttc    420
acactgttct aaaaatactt atattttggg acggagggag tacacattag agcaggtaca     480
```

| | |
|---|---|
| atagcagact agtagccagc tataaacata ttttaatgag ataaaagatg agagagaaca | 540 |
| gcgggctaca gatctgtagc cagctgcagc acggactcca agacattgtg tgtgtatgac | 600 |
| aggtgggacc atatattaat agtacagtaa gtaactattg tatgaattgg ctattagatt | 660 |
| agctataggt gaattgtagc tagtagtggg ctatactatt gaacttactc ttatatctct | 720 |
| caatatctcc agaaaactag gacgatatat attgatatta acaaagtcat catagatatc | 780 |
| tcgctatcga catatatatt acctatcact gaaaaaataa ttaatcataa atgcaagcac | 840 |
| atatactacg ttcaacactg aatgtaggta gattggtaga cgggttccac cgcaagaaaa | 900 |
| gcattgcacc agtgaagaaa gaaacatcgg aatttgtatg tagtttgttg tttgatgaat | 960 |
| tcttttgatt aaaaaaaact aaaatcagag ttgattcagt taatggtgtt gcctacgata | 1020 |
| tacttccata tcatgatatc actgtagact atgaatcata tctttaatta aaactaaatc | 1080 |
| aagaaattaa gtatgagacc tcaactcaat gaagaatttc tagttgaaaa acattcctag | 1140 |
| tgtgcgttcg gatggaggta gggatcttct ctccgttcat ataaaaccgg atggttcatt | 1200 |
| agaacatgat taattaagca acagttaatc taaaaataaa ttaatatttt ttaagaaatt | 1260 |
| tttgtataga gatcttttga aaaaaatca ttggttagaa agcatactaa taaaagaga | 1320 |
| aaaataagaa catagtacta tagtagaaaa tgagaacttg gagtatttga gaggatggga | 1380 |
| aataagaaga ttaagaagat gcgtaaagtg aacggttaac gcatgattga ttaattaaat | 1440 |
| attaattatt ttaaatttgg aaaataaatt agtatgattt ttaagcaaca tatatatata | 1500 |
| tatatatata tatatagaaa aacatagttt tagaaaatat aagcgtgtaa acgatatgc | 1560 |
| aggaacgaaa cgttgagcat tcaaaatttc aaattgaaca tatgaatcaa gagagaataa | 1620 |
| aaaaagaggc cttctaggct ggcatggaca attggacatg ttttcaacta gggtttcaag | 1680 |
| cttcgagcat ccacttttgt ccttgcaaac tttatacggc aaggcccgtg aatctagccc | 1740 |
| cccacaccac cccacccgcc cgcgccgcgc ggccgcctcg cctcccctcc cttctcctcc | 1800 |
| tctccgcccc cgccgccagg ccgtccacct ccgccgtctc ctcccccatt cgcacccaag | 1860 |
| gcgctggcgc ggaaggc | 1877 |

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193

| | |
|---|---|
| caccaaatat agtgttattt caatactaaa atggtgttat ggttggagat gccctaaaga | 60 |
| taaacatgac gagacacgag atttattaat ttcttgatca accataactt ataacttaa | 120 |
| tattaatttc acttaataat ttccaattaa gtgaatcttt acttcaccaa aagttcctaa | 180 |
| cgaactctta ttttctagca tcaatattac catgaactag catcaatact atcatgaaaa | 240 |
| attcctactt cctatccaac tcttaataac aatgctagtc ttaacaatat tcatcaaaaa | 300 |
| cttgatatag accttctaac ttagccacga ctagtatcgg tgaataccaa aattaatgta | 360 |
| ttcatgagaa cttgagattt ctctaatgta ttcttgttac taaacaagta acaacactca | 420 |
| agaaatatca tgatcaaata ttttactcat aaactcccata tttcacattt tgaaaatttt | 480 |
| aaacagcaaa tcacattgaa ttttcgtggt aaaagtattt aaaattgaaa aatagcagct | 540 |
| cctgatttca atgtataaat ttatctttat atggtttatg tctccaactt attttaaaaa | 600 |

| | |
|---|---|
| agagagaaag agcacccaaa aggtgaccgt ttgaaattcg aatttatttc cgtttgaaat | 660 |
| tcgaattcaa aaaagtaaaa ccgaaccgag tctcgttact gactgtcaca cattgtttcc | 720 |
| ctaaaagcta attaacccat acgtggcgta atataacagg tcagtgatca atactaaata | 780 |
| acagacatac acctttaaaa ttcgtgcacg ctccaaaaca aaatctacac ttcaaaatca | 840 |
| acggtcacga tcattcctca aatttcaaaa aattatttaa cctcacttcc ttcgctttgt | 900 |
| ttttaaaacc tctctctctt tctctttctc tttcgccatt aaaactctgt ttccttttc | 960 |
| agagattctc agagaagatt cattttaccc taagaaaaaa | 1000 |

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194

| | |
|---|---|
| ttgagcctta ttgttgttat tgacttttag ccaatagaaa gagatggaaa ttcaataatt | 60 |
| atccacaaaa ttccaaatca ttggtgtaca aaaagatcta aggctgttat attttcaaaa | 120 |
| aagaaagaaa agaaatgcaa caaatatgga ttaaactgtg gtttgtaaat tgagctttgc | 180 |
| atgaaaactt tatcactatg atttcactac tccatattta ttgactaaag tggcactaat | 240 |
| gaatttctta atcatgaaat cttgtatcaa aaagtactaa aataaacatg acattggcaa | 300 |
| ttaggaaaat tctaaattag aaattagtaa aaatgaaagg tgaaagggaa agatgatgat | 360 |
| atgaattggt tggtgaccag gagaaatgta tcccgatttt tgcagacact ttcagtgtcc | 420 |
| ccattcatat aattatggcc cacctcgtta agatttttca ttcaccacca taacaagatc | 480 |
| taagcttaga tttcatgtaa ttaaacatat aatatacttg ccaatactat ctaataaagt | 540 |
| atacttaagc aaaaattatt actctagtgt aaggcgatga aatataagtt tagttgaaaa | 600 |
| tttatgtcga tataacaaag tataatgaat taagaccttg gttttcgatt aacaaactaa | 660 |
| ttaaacacta gttttgccta ataaaaccgg gaatcgtatt caaaaccgaa cgacaaaaca | 720 |
| agggacaagt tgagagacaa aaccaaatca gcatctttct tccagaaatg tcatgaccac | 780 |
| atgacgtcat cttgacccct cttcattgtg atatctgtgg ataaagcgca cgtgtttaat | 840 |
| tcacgaacct tcgtagtaac gaaaaatcca caactttcat atttttaat tacccactaa | 900 |
| actaaaacaa atttggaaaa acatgaaaaa cttttctttt ttttccaggt tcgtgaacct | 960 |
| cgtaccctct atataaacct cttaaccacc ttccacata | 999 |

<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195

| | |
|---|---|
| tgaattgagt aaaatgtgtt ttcaaacagt taggtggtag aaggtaaagg taataacatc | 60 |
| atgatcttac taaaagaatt gttgcatact aactatcaat attctcaaca acataatata | 120 |
| atgttttttt aggtaatttt ccattttaat tttttgtgat taaacaatta aacaactcga | 180 |
| atgatgatga taaaaaaaaa aaattaacaa ctcgaataag ttaaagtagc aatacacatg | 240 |
| tcgttcaatt caaccaataa agtaagactt atattttaa gaagttgact aatagcttaa | 300 |

-continued

```
taagttggaa aacttgtgta gtttcttaat tcccacgtgc agtaagaaat aaaaatgaaa      360
aaaattatta tatccttccc actctgcgac ttttctttta ttttatcaaa tattaaaaag      420
attcatatca cagtttacac attgaaatca taaacgataa ttatgtattt tgtaataaaa      480
agttagttct gaagctcata cttttggatag tcgctagtcg ctaatatgct ccttgtaata     540
attaaagtca ctacgacgca cgtcaaagcc gatatttagg gcttaattga tgcgtgtttt     600
tcttttcata taatagtaat ataaattagt actaataaag tatgatggat ggttgagaca      660
gaaaagaaaa aagatgactg tatggtcatc attacaaaga agaatgtatt cttcatgttc      720
ttaagaataa taaaatgtca cttgtaaatc aagttggtaa gcattttgag aactttgttc      780
gatgcaacgt atgatgattt atgtagacaa aagataaaac cgtatcttca actattgcca      840
agaaaagata aaacctaatc tagtcagtct ctcaacataa atacaaccca atagccaaac      900
tgtgtccaat tcggagagaa actaaactaa acaaaacac aaaagcccaa cataagccca       960
ataaaaccca ttttataaac agaacattac taacactca                             999

<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196
atgatgaaca ttctacatat ataattatta tgtttaagca cttagacagc ataaattctt       60
tctaattata taaatctaac cttgttacat tgtacatcta taaattactt gaagaaataa      120
cgagttctat ttctttttaa aaattaaaaa tactatacca tatctcagtg attaagttga      180
accaaaaggt acggaggaga aacaagcatt tgattcttcc ttattttatt ttattcatct      240
ctcactaatg atggtggaga aaaaagaaa atacctaaca aacaaatata tattgtcata      300
caaaaatatt tctatatttt tagttaatta gtttatattc ctcacttttc agggcttata     360
taagaaagtg agcaaacaca aatcaaaatg cagcagcaaa tactatcatc acccatctcc      420
ttagttctat tttataattc ctcttcttt tgttcatagc tttgtaatta tagtcttatt      480
tctctttaag gctcaataag aggaggtact attactacac ttctctctac ttttacttgt     540
attttagcat taaaatccta aaatccgttt taaattcaaa aataaactta gagatgttta     600
atctcgattc ggttttttcgg ctttaggaga ataattatat gaaattagta tggatatctt    660
tactagtttc cattcaaatg attctgattt caatctaata ctctcactct ttaattaaac     720
tatatgtagt gtaatttcac actgttaaat ttctaccatg tcatgtatat tagagttgca     780
tagaaaattg taaacatcc atttgaattc gaatgaaaca aaatgttta aaataaaatt       840 ttggttttta aagaaaaat ctaaaactga attatatcgt ttaaccaagt tgtaaaagtc       900
ataaaacgta gtatcttgta aatcgctctt ccacggtcca aatagacttc tagtaataaa     960
caagtaaaac taattttggt ttcttactaa ttttcacaga                           1000

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108
```

<400> SEQUENCE: 197

```
ttagctgaac caggaaattg atctcttata ccagtttccg ggtttagatt ggtttgatgg     60
cgatttgatt aaaccccga aattttatgt cgtagttgtg catagtatta ttattctttg    120
cggacaatag acgtatcggg accaagttct gtagcaaaat tgtataagct taagtttgat   180
gaaatttaaa ggtaatcact aaaacccaaa tgggacaata accggtgaa gatttagagt    240
ttttaatttt gactcatgaa tctggagaaa gagccctcgt taaaaggagt gaatcaatcc   300
ataggggaaa aagttttgtc ttttaaaaa ctaaagaacc aaaccttaat agaagcagct    360
caatgtgtga caactttcca ctggcactaa gataaagtga ctagcgatga gtgcaattat   420
tgaaatagta gatggtaaat attacataca agagtaaaaa tatctttatg tcaatgctta   480
attcagtgtt tctggttaac aagagaaact tctctaactt tcgtaattgg gtcttataaa   540
attttatgca attatgattt taccctttta ctacttttca ttagctttca cgaatctatt   600
ttgacaagag aaatcattag aggtaaacat gcttttggt caagggcctt aacagttcca    660
ccaatcaagc tcaaaagttg tacttaaccg acatcttctg tgaaaacata taattacatg   720
tacaaatcaa aactaccta tgaaataaat agaaatattg cagttcattt ctaatttaac    780
ctcttcaact tttaaaacta tttacatttc tttatgtcat ttctagtcat tttgatgcaa   840
attgtaccat ttatggatta tcttcacaaa tttttaagtt ggtgaaaact ttttggtggg   900
tagttaaaac ttgaaataga aatttacttt accaaaataa actaatgaaa agtaatcact   960
ccactcccta taataagatt tccaacgttc ccactaagc                           999
```

<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198

```
tagttccatt acaatttcca aatgattgt tacaaagcta caagattatt cgaaatagga     60
tttcatccat aagagagaat ggtgtggtcg acgctacaat gttgatttat tggttgtggt   120
ttgcatcttg gggatgtcaa atcctaagtt tcaagttctt gtaaaaacgt tttcaggttt   180
ctttaatata ttttaatatt aatgtaaaaa gaaagatat agcttttgta caaaaaaatt    240
tgtttaatca ctatgtagga ggatgcgatc aaattcatgg aatgatgtat tattagcttt   300
tctatcctca ctctaaaaac aatactatag tgagttaaat aatttgatca tttcaatgta   360
gattaaaatt ttattaaaag aagaaaaatt taaaagccta aacaaaata aaaaggagg     420
ctcgaggtat gatgggtgta gcagaagagc tggcaacagc tatcgactga gtgattacga   480
actcagtact cagtgttctc agctcacaca ctctttttt gttctctttc ttttggacag   540
ctttcatttt ctcttttctt ttttctattt tgtttcaaaa ttccatccat attaaaatag   600
gcctgatcat gagaataaag gaaatactaa tgatgagttt ctcaataatg caataagatg   660
caattattat gagctatttta ctattgaaaa tgagcaaata aatgtcaaaa cacaatctgg   720
ttaagttaga gcaactccat tgtataggat tcatgtagtt tctaagaaaa caaaatgtat   780
taatatttta cttttacatc caaaaaacca acttatatga gtaatagaaa cgatcctaat   840
attaggaatt ttagagattt tctctcatct gtttcttaac ttttcaatat tttattttt    900
```

```
taaaattgta tgagtttcta ctaagaaact actgctggag ttggtcttag cttcccaatg    960
cttctccacc tatatatatg catatctcct tcttaaaac                            999
```

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

```
aagcggcaat ttagtaagaa gtactcaaag tatcatttac caaaagtata tggttttggg     60
aagagttgtt agggatgtat tctttctaaa cagatgatat gacgatgttc ttgaaaacta    120
atgttaaaga cggaatctct ggcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aagaaaaat tacgaaagaa aacaggaaat caaatcaaaa gataaagaga     480
aggtaaaaaa aggcaagaag cactaatgtt taatatttat agtttctcc attaaagaaa     540 aagcgatgat gtgtgttctc atctttttgtg aaagtatata tattgctttt gcttttctca    600
aaagcaaaag actcatccaa caagaacaaa aaaaaaact aaagctcaat ccaaaagacg     660
aagaatgcat tggatactac aacttctttt tcacttttct ttcaaattta caattatgat    720
tttcacaata cagtttattc aaaaataaat aaaaaaacga ggcatgaaaa taatgattat    780
cctcttcact tattaagcca ctcactataa gcagagcaac tccagaacat agtgagcccc    840
caaaacatta aagcatgatg atgtctaatg atgatgatct tcttcgttcc atttctctaa    900
atttttggga tttctgcgaa gacccttctt ctctttctct tctctgaact tcaagattcg    960
tgtcggacaa atttttgttt ttatttttct gatgttaca                            999
```

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200

```
atctataacg agttaacatg ttgccagttt gaatcaagaa gcttggatga tgaatgaatg     60
gatcggtttg tggtacaatt cttaaaattg tagtagagga gacagagaaa aaacatgata    120
agactttggt atttacaact tgacggagac aagacagtaa gccaaatctg tcacaaaaac    180
actcaaactc ttttctcagt gttttgagtt taaagagaga cttattcact tcccctttcg    240
taacacttat ttgtctccca accaaacagt ttctgtcctt tcccttgtcc tcccacgtgc    300
atctttatat ctcatgactt ttcgtttcta gatcttgaat aatgtcttag tggattaggt    360
ttgttgtcgg taaattaggt gaccgttttt ttcttatatt tggaagatcg cgggatgaag    420
cagatactga gtttcagggc atacacacct aatttgaaaa tcattgttag tccaatttca    480
ctttaatctt gtttacaaaa aaattgatct gaaaatgttg atgggataag taaaaatgta    540
agttttgcta gtagtcatga tataataata gcaaaaccag atcaattttg agcaaaagga    600
```

```
agaaacaaaa aacagatcga tcccacgagc aagactaagt gtaaagtggt tcccacaaga      660
gccatatgga tatggtcctt caacttttaa agcccattac ttcagtggtc gacccgacat      720
tacgccacga gtagtcacgc acgcacgact ccgttcacgt gacattcacg ttgatatttc      780
cccctctact ctcttctgct tggttgatct aaaaaacatg aagagaccaa cctaatttca      840
tattaatata tgatatagac ttcatactca acagtcactt tcgtaatcca aatccatatc      900
ttacgaaatt agttcttaat aaaggttgtg gattaagtta taatattgtg ttaagagtta      960
agacacagca tataaccttg taccaacagt gctttattct taaatggaaa caaaacatat     1020
gtcaatgtca agcatacagc taaaatatca ttatctaata ttaagagtaa aacaagataa     1080
ttaaaaattg aaacaacacc atatttttat agctttactt atcgtatttt tctagtcttc     1140
atggtaattg tgttgcttta ttttgtttat aaatgaattt ggttcgacca gatagtctaa     1200
tatcagtttt taaacactgg ttttaataaa atcatatgtc ggcaattcaa cctgttacgt     1260
tgtatgattg tatcctagtc aaatagggga ggaggtacta gtcgtttcaa ttagtttacg     1320
taatcaatcc aaagaaacta taagctataa agatcctcaa tttgttggtt acaataaaaa     1380
caacagttgt caaaatttat gtttatataaaa agtaataact atgttccttc ccatatagag     1440
caaagtacct caggataggc aaaccgtact taatagccct tattcataat ttgatccaac     1500
tcttccccac aaaattgcaa ctgatgaagt caatacttgt atagtgagtc aagctataaa     1560
tgtctagtga tagttttgtc tcttaaaagg ttaacaaaag ttatgacaag ctgaaaaatc     1620
agagtttgct aggagtatta cttacagtta tcagtttaag tatcacattt atagtattgt     1680
atacaatgat tcttaaattc cacctttttcc gtgcgaaacc aaattttcta ttggaaacat     1740
agaatgtaaa caaaaatatg ggacgttgtc cgttccaaca ttaaccaaac ttgtctatta     1800
ctaatattcg tgttggtttg atgttggatg tctaaattcg ttgaatcatg tgtctcttga     1860
cgaaatatgc atcttcttat ttcttagtat agatgcactt tatcattctt ttagtacatg     1920
cttaattttt tttttttaaaa tatgttgatt gtcatattgc caaaagtatg aattaaagac     1980
gcacatctaa cacaagttag cagccgtaaa tccttccata aatttatttt gcaagttttg     2040
ctcattatat aatgagcgga atttatgata taatcgtttg taataatgtt atgttttgat     2100
caaaatttga aattaaaagt aggtgagaac ttgttataca gtgtagataa ggtggatctt     2160
gaatataaaa ataaaattta taagatgtat ttaaagcaga aaagcataaa actttagata     2220
aaataatgta aaaatgtgtt agcatcaatg ttgggatatt ggccgacccg aacttaatca     2280
atgtcggaag ccattacttc tctcccaaaa gaccttttttc cttcggagaa ctaggaactt     2340
cctcactacc tttcgcttaa cgtgaaagcc ataaatttca tatattcata aaaatcagaa     2400
aatctaaaac tgtttagtat cacctgtttt tggtatagac tattggtttt gtgttacttc     2460
ctaaactata tgatttcgta cttcattgga tcttatagag atgaatattc gtaaaaagat     2520
aagttatctg gtgaaacgtt acttcagtca tgtttgggtct agatttacat actactatga     2580
aacattttaa gataataatt atcctagcca actatatgtt ctatattatg ggccaagaag     2640
atatagaact aaaagttcag aatttaacga tataaattac tagtatattc taatacttga     2700
atgattactg ttttagttgt ttagaataaa tagtagcgtg ttggttaaga taccatctat     2760
ccacatctat atttgtgtgg gttacataaa atgtacataa tattatatac atatatatgt     2820 atattttga taaagccata tattactcct tgacctctgc ccccatttcc ttttactata     2880
aataggaata ctcatgatcc tctaattcag caatcaacac caacgaacac aacctttttcc     2940 aaagccaata ataaaagaac aaaagctttt agtttcatca aagacgaagc tgccttagaa     3000
```

```
<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201
agaagtattc acgcaccaag gttatatttg tagtgacata ttctacaatt atcacatttt      60
tctcttatgt ttcgtagtcg cagatggtca attttttcta taataatttg tccttgaaca     120
caccaaactt tagaaacgat gatatatacc gtattgtcac gctcacaatg aaacaaacgc     180
gatgaatcgt catcaccagc taaaagccta aaacaccatc ttagttttca ctcagataaa     240
aagattattt gtttccaacc tttctattga attgattagc agtgatgacg taattagtga     300
tagtttatag taaaacaaat ggaagtggta ataaatttac acaacaaaat atggtaagaa     360
tctataaaat aagaggttaa gagatctcat gttatattaa atgattgaaa gaaaaacaaa     420
ctattggttg atttccatat gtaatagtaa gttgtgatga aagtgatgac gtaattagtt     480
gtatttatag taaaacaaat taaaatggta aggtaaattt ccacaacaaa acttggtaaa     540
aatcttaaaa aaaaaaaaag aggtttagag atcgcatgcg tgtcatcaaa ggttcttttt     600
cactttaggt ctgagtagtg ttagactttg attggtgcac gtaagtgttt cgtatcgcga     660
tttaggagaa gtacgtttta cacgtggaca caatcaacgg tcaagatttc gtcgtccaga     720
tagaggagcg atacgtcacg ccattcaaca atctcctctt cttcattcct tcattttgat     780
tttgagtttt gatctgcccg ttcaaaagtc tcggtcatct gcccgtaaat ataaagatga     840
ttatatttat ttatatcttc tggtgaaaga agctaatata aagcttccat ggctaatctt     900
gtttaagctt ctcttcttct tctctctcct gtgtctcgtt cactagtttt ttttcggggg     960
agagtgatgg agtgtgtttg ttgaatagtt ttgacgatca                         1000

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202
caaagtattt gacaagccat atggttttgg atcaaaaagt cggtccaaaa ttaatgtttt      60
atgtgcaaga accgacccat tgtacacacg tgttaacatc ttcaagactt tcatctctat     120
ttttcttttg gtcattaaga tacccattga tccgaatctg ttacattccc acctactttt     180
ttaattttta ctatccactc caaattaaac acaaccgatg attttaataa ttggaagctt     240
tttaaaatat ttctccacgt gcctctttgt gtttgtctat ata                       283

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203
aaagttattg acattttgaa aggaccgtaa atattaccaa aaaactgacg gagttaggat      60
cggccacgta gaaagggaca aagagagaac agtcacggac tcggccagac taagtatggg     120
```

```
cctgtctgaa tccaaactca gctaagttcc aaaagcataa agagagatgt gtaatgaaat    180
gaacgtattc tagaaacgaa agcaatgtta tgctttgttt ttgagccaca tgttttgggg    240
agatggagag aatcttttt acgttttta cctaacccac ttggcacttg gccaaaaag     300 tgagaagaaa ctgtggcgaa tgagtaggcc acgccatgga ctttgttcct tgtccttcaa    360
aagttaaatt tatgttatgc gtggggacaa tctaagcaac gtggttcctt taaatatcgc    420
agcttcctct tttacacttt tggagcctac gtgttttgtt ttggaccggc caaatacacg    480
agtcagtcag tttagaaata atttggatgt ccaaaaatct tggagatcca aataaaataa    540
ttagcatgtt ttagttcata agaatatgaa atgtagataa actgtctata ttaatttttc    600
catagaattg gcttttatc gaggtgatgt acttaatgac tttgttgatt actactcgta     660
taacaataaa gaatatgata ctatgtgaga cttataatga atttggtgtg tgttaattaa    720
tccagttgaa acagtttaat aacaaatcag aataaaaatt gtagtaagaa aatttgaacg    780
ctgatccttc aacctagata gtgaaccttt caaatactat atgattcacg tgtaatgttt    840
ttgaccgttg gttattttg tgtgaactat attaacttat caatatcgaa aggctaaata    900 agtaaaataac taaagaaag ttcaggaaac aactcgacct aatgacctat catttctgat    960
cacccgtcct ataaatacat acgtaagatc attcgttact                          1000

<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
```

```
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45
```

```
Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met
65                  70                  75

<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75
```

-continued

```
<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
```

```
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

-continued

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 215
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys

<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T -continued

```
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                  10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Glu Gln Glu Ala Leu
1               5                  10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75

<210> SEQ ID NO 222
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met
65                  70                  75

<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

-continued

```
<400> SEQUENCE: 223

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met
65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

-continued

```
<400> SEQUENCE: 225

Met Glu Ser Glu Gly Lys Ile Val Phe Thr Glu Glu Gln Glu Ala Leu
1               5                  10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Glu Gln Glu Ala Leu
1               5                  10                  15

Val Val Lys Ser Trp Thr Val Met Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 227

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

-continued

```
<400> SEQUENCE: 229

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of U.S. application Ser. No. 16/659,220, filed Oct. 21, 2019 (pending), which application divisional of U.S. application Ser. No. 16/275,629, filed Feb. 14, 2019 (now U.S. Pat. No. 10,508,284), which application is a divisional of U.S. application Ser. No. 15/362,633, filed Nov. 28, 2016, (now U.S. Pat. No. 10,240,166), which application is a divisional of Ser. No. 11/779,266 (abandoned) filed Jul. 17, 2007 which application is a Continuation-In-Part of application Ser. No. 11/778,060, filed Jul. 15, 2007 (abandoned), which is a Continuation-In-Part of application Ser. No. 11/248,547, filed on Oct. 12, 2005, and this application is also a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., TT Kozlowsky, ed, Academic Press, New York, pp 23-64; Graham and Patterson (1982) Annu Rev Plant Physiol 33: 347-372; Guy (1990) Annu Rev Plant Physiol Plant Mol Biol 41: 187-223; and Nishida and Murata (1996) Annu Rev Plant Physiol Plant Mol Biol 47: 541-568). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE (Edgar (2004) Nuc. Acids Res. 32(5):1792-1797).

FIG. 2 is an alignment of ME02779.
FIG. 3 is an alignment of truncated mutant of ME02779.
FIG. 4 is an alignment of ME03944.
FIG. 5 is an alignment of ME05304.
FIG. 6 is an alignment of truncated mutant of ME05304.
FIG. 7 is an alignment of ME03186.

DETAILED DESCRIPTION OF THE INVENTION

1. Definitions

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic *Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1, F_2, F_3, F_4, F_5, F_6$ and subsequent generation plants, or seeds formed on $BC_1, BC_2, BC_3,$ and subsequent generation plants, or seeds formed on $F_1BC_1, F_1BC_2, F_1BC_3,$ and subsequent generation plants. The designation $F_1$ refers to the progeny of a cross between two parents that are genetically distinct. The designations $F_2, F_3, F_4, F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol*. 30:321-9); RCc2 and RCc3, promoters that direct root-specific gene transcription in rice (Xu et al. (1995) *Plant Mol. Biol*. 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\% \ G+C) - 500/L - 0.63(\% \ formamide) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynuceotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) *Proc Natl. Acad Sci USA.* Jan; 87:103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and
(g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica*, v. 85, n.1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino acid sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
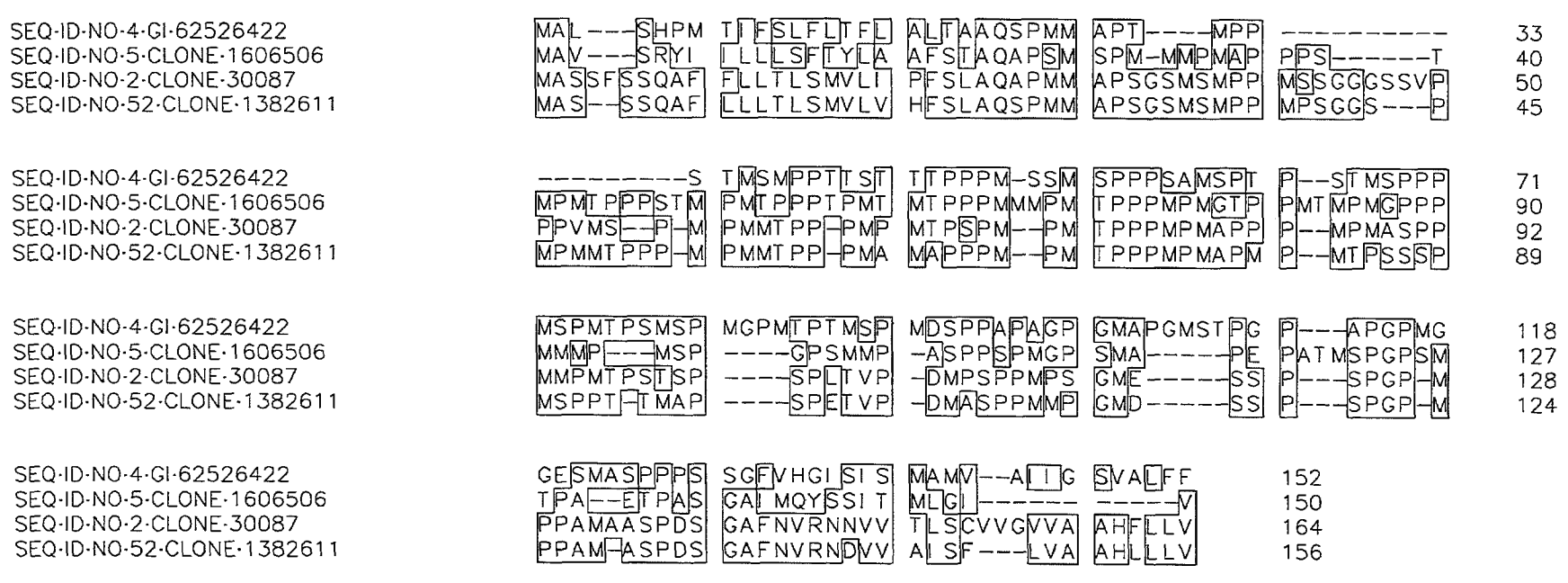
Figure 7:
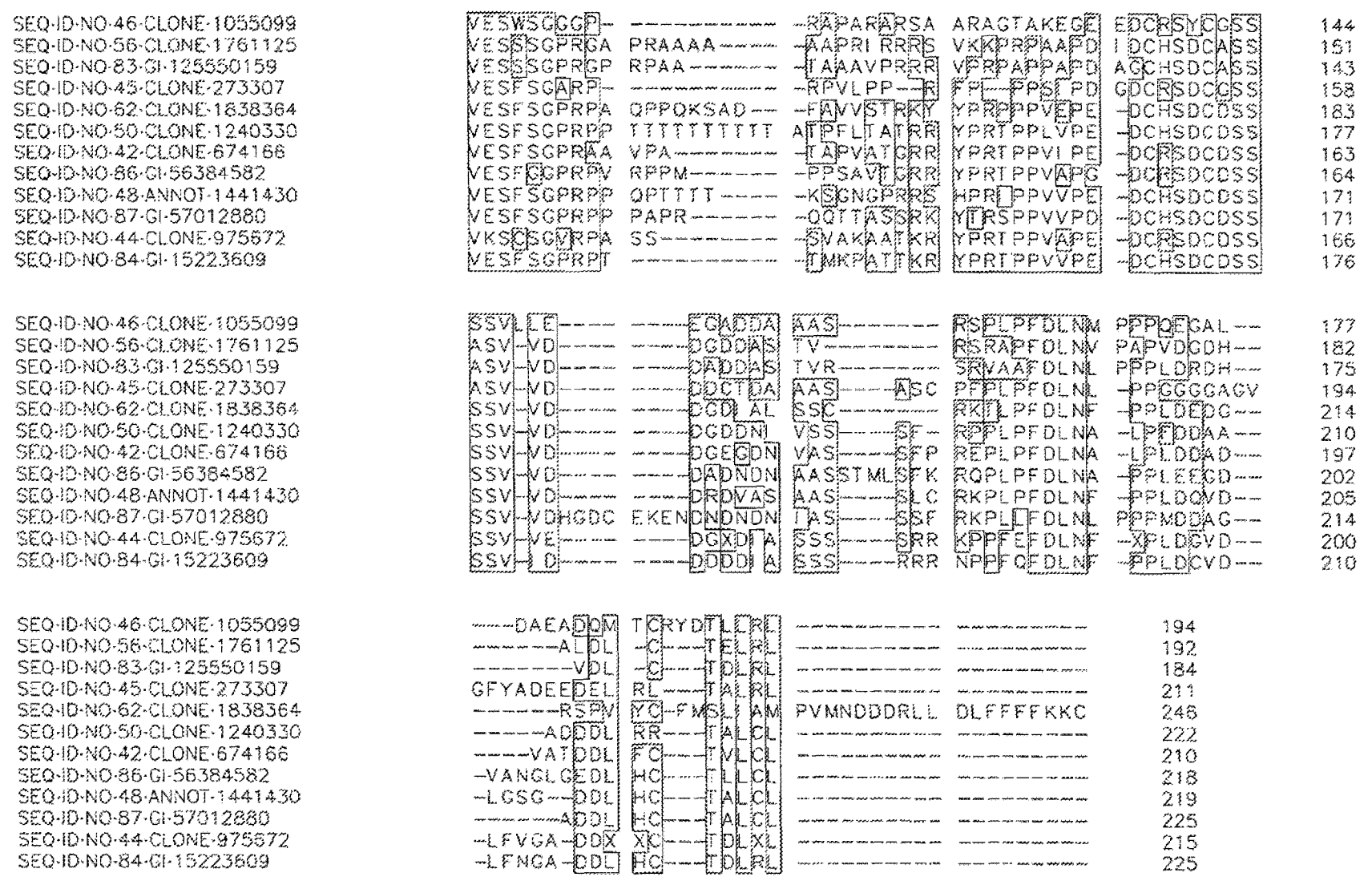

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMI generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple anti sense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5X MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

References: Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold-germination and vigor |
| Coding sequence/ Species of Origin | 1. Vector Construct Sequence Identifier 14298746 corresponding to Clone 30087-ME01451; encodes a 164 amino acid protein of unknown function from Arabidopsis. |
| | 2. Vector Construct Sequence Identifier 14298770 corresponding to Clone 30469-ME02779 encodes a 78 amino acid protein with identity to the N-terminal half of an Arabidopsis class I nonsymbiotic hemoglobin. |
| | 3. Vector Construct Sequence Identifier 14301197 corresponding to Clone 271922-ME03944 encodes a 92 amino acid 60s ribosomal protein L37a protein from Arabidopsis. |
| | 4. Vector Construct Sequence Identifier 14296769 corresponding to Clone 2403-ME05304 encodes a truncated ubiquitin-like protein from Arabidopsis. |
| | 5. Vector Construct Sequence Identifier 14301334 corresponding to Clone 674166-ME03186 from *Glycine max* encodes a 210 amino acid protein with similarity to the ethylene-responsive element binding protein (ERF) family. |
| Species in which Clone was Tested | *Arabidopsis thaliana* |
| Promoter | 35S, a strong constitutive promoter |
| Insert DNA type | cDNA |

Introduction:

How plants respond to stress in the environment dictates their ability to survive and reproduce. There are probably many mechanisms by which plants regulate the temperatures under which they will germinate (Lu and Hills, 2003). Finding genes that result in stress tolerance when overexpressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:

Generation and Phenotypic Evaluation of T1 Events.

Wild-type *Arabidopsis* Wassilewskija (Ws) plants were transformed with a T$_1$ plasmid containing different Clones in the sense orientation relative to the 35S promoter, by *Agro-*

*bacterium*-Mediated Transformation. The $T_1$ plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent T2 transformation events were evaluated for each line under cold conditions. Subsequently, T3 generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5X MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results:

Example 1: ME01451

TABLE 1-1

| Construct | Event/Generation | Plant Stage | Assay | Result |
|---|---|---|---|---|
| 35S:: 30087 | –01/$T_2$ Finale resistant plants | Seedling | Cold Germination | Significant at p ≤ .05 |
| 35S:: 30087 | –05/$T_2$ Finale resistant plants | Seedling | Cold Germination | Significant at p ≤ .05 |
| 35S:: 30087 | –01/$T_3$ Finale resistant plants | Seedling | Cold Germination | Significant at p ≤ .05 |
| 35S:: 30087 | –05/$T_3$ Finale resistant plants | Seedling | Cold Germination | Significant at p ≤ .05 |

Ectopic expression of Clone 30087 under the control of the 35S promoter induces the following phenotypes:

Early germination at 8° C. resulting in larger seedlings after 10 days of growth in the cold.

Plants from Events –01 and –05 which are heterozygous or homozygous for Clone 30087 do not show any negative phenotypes under long-day conditions.

The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, –01 and –05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events −01 and −05 segregated 15:1 and 3:1 (R:S), respectively, for Finale™ resistance in the $T_2$ generation (data not shown).

Qualitative Analysis of the $T_1$ Plants:

The physical appearance of all ten $T_1$ plants was identical to the controls.

Qualitative and Quantitative Analysis of the $T_2$ Plants:

Events −01 and −05 of ME01451 exhibited no statistically relevant negative phenotypes.

Germination

No detectable reduction in germination rate.

General morphology/architecture

Plants appeared wild-type in all instances.

Days to flowering

No observable or statistical differences between experimentals and controls.

Rosette area 7 days post-bolting

No observable or statistical differences between experimentals and controls.

Fertility (silique number and seed fill)

No observable or statistical differences between experimentals and controls

Example 2: ME02779

TABLE 2-1

| Construct | Event/Generation | Plant Stage | Assay | Result |
|---|---|---|---|---|
| 35S::30469 | −01/$T_2$ Finale resistant plants | Seedling | Cold Germination | Significant at p ≤ .05 |
| 35S::30469 | −03/$T_2$ Finale resistant plants | Seedling | Cold Germination | Significant at p ≤ .05 |
| 35S::30469 | −01/$T_3$ Finale resistant plants | Seedling | Cold Germination | Significant at p ≤ .05 |
| 35S::30469 | −03/$T_3$ Finale resistant plants | Seedling | Cold Germination | Significant at p ≤ .05 |

Ectopic expression of Clone 30469 under the control of the 35S promoter induces the following phenotypes:

Early germination at 8° C. resulting in larger seedlings after 10 days at 8° C.

Plants from Events −01 and −03 which are heterozygous or homozygous for Clone 30469 do not show any negative phenotypes under long-day conditions.

The gene corresponding to Clone 30469 is down-regulated in ABA, heat, and germinating seeds and up-regulated in high nitrogen and most cold and drought treatments.

Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, −01 and −03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events −01 and −03 segregated 3:1 (R:S) for Finale™ resistance in the $T_2$ generation (data not shown).

Qualitative Analysis of the $T_1$ Plants:

The physical appearance of nine of the ten $T_1$ plants was identical to the controls except for Event −09, which exhibited small rosettes and reduced fertility.

Qualitative and Quantitative Analysis of the $T_2$ Plants:

Events −01 and −03 of ME02779 exhibited no statistically relevant negative phenotypes.

Germination

No detectable reduction in germination rate.

General morphology/architecture

Plants appeared wild-type in all instances.

Days to flowering

No observable or statistical differences between experimentals and controls.

Rosette area 7 days post-bolting

No observable or statistical differences between experimentals and controls.

Fertility (silique number and seed fill)

No observable or statistical differences between experimentals and controls

Example 3: ME03944

TABLE 3-1

| Construct | Event/Generation | Plant Stage | Assay | Result |
|---|---|---|---|---|
| 35S:: 271922 | −02/$T_2$ Finale resistant plants | Seedling | Cold Germination | Significant at $p \leq .05$ |
| 35S:: 271922 | −06/$T_2$ Finale resistant plants | Seedling | Cold Germination | Significant at $p \leq .05$ |
| 35S:: 271922 | −02/$T_3$ Finale resistant plants | Seedling | Cold Germination | Significant at $p \leq .05$ |
| 35S:: 271922 | −06/$T_3$ Finale resistant plants | Seedling | Cold Germination | Significant at $p \leq .05$ |

Ectopic expression of Clone 271922 under the control of the 35S promoter induces the following phenotypes:
  Early germination at 8° C. resulting in larger seedlings after 10 days at 8° C.
Plants from Events −02 and −06 which are heterozygous or homozygous for Clone 271922 do not show any negative phenotypes under long-day conditions.
The gene corresponding to Clone 271922 shows little differential regulation in transcription profiling experiments on wildtype.
Clone 271922 encodes a 60 s ribosomal protein L37a.

Two Events of ME03944 Showed Significant Early Germination Under Cold Conditions in Both Generations.

Four events of ME03944 were sown as described in the Cold Germination Assay in both the $T_2$ and the $T_3$ generations. Two events, −02 and −06, were significant in both generations at $p \leq 0.05$ using a one-tailed t-test assuming unequal variance (Table 3-2). The $T_3$ lines are indicated as −99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.
  Events −02 and −06 segregated 3:1 (R:S) for Finale™ resistance in the $T_2$ generation (data not shown).
Qualitative Analysis of the $T_1$ Plants:
  The physical appearance of five of the six $T_1$ plants was identical to the controls. Event −03 exhibited a small rosette and curled leaves.
Other Characteristics:
  Seedlings from ME03944-06 exhibited elongated hypocotyls. This phenotype co-segregated with Finale™ resistance.
Qualitative and Quantitative Analysis of the $T_2$ Plants:
  Events −02 and −06 of ME03944 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls

Example 4: ME05304

TABLE 4-1

| Construct | Event/Generation | Plant Stage | Assay | Result |
|---|---|---|---|---|
| 35S:: 2403 | −01/$T_2$ Finale resistant plants | Seedling | Cold Germination | Significant at $p \leq .05$ |
| 35S:: 2403 | −04/$T_2$ Finale resistant plants | Seedling | Cold Germination | Significant at $p \leq .05$ |
| 35S:: 2403 | −01/$T_3$ Finale resistant plants | Seedling | Cold Germination | Significant at $p \leq .05$ |
| 35S:: 2403 | −04/$T_3$ Finale resistant plants | Seedling | Cold Germination | Significant at $p \leq .05$ |

Ectopic expression of Clone 2403 under the control of the 35S promoter induces the following phenotypes:
 Early germination at 8° C. resulting in larger seedlings after 10 days at 8° C.
Plants from Events −01 and −04 which are heterozygous or homozygous for Clone 2403 do not show any negative phenotypes under long-day conditions.
The gene corresponding to Clone 2403 shows little differential regulation in transcript profiling experiments on wildtype.
Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, −01 and −04 were significant in both generations at $p \leq 0.05$ using a one-tailed t-test assuming unequal variance (Table 4-2). The $T_3$ lines are indicated as −99 which indicates that the seeds are the bulked progeny from several $T_2$ plants.

TABLE 4-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events −01 and −04 segregated 3:1 (R:S) for Finale™ resistance in the $T_2$ generation (data not shown).
Qualitative Analysis of the $T_1$ Plants:
 The physical appearance of seven of the ten $T_1$ plants was identical to the controls. The other three events exhibited the following phenotypes: late flowering (Events −01, −02 and −08), dark green rosette leaves (Events −01 and −08) and shorter petioles (Events −02 and −08). Event −01 did not reproduce the late-flowering phenotype in the $T_2$ generation.
Qualitative and Quantitative Analysis of the $T_2$ Plants:
 Events −01 and −04 of ME05304 exhibited no statistically relevant negative phenotypes.
 Germination
  No detectable reduction in germination rate.
 General morphology/architecture
  Plants appeared wild-type in all instances.
 Days to flowering
  No observable or statistical differences between experimentals and controls.
 Rosette area 7 days post-bolting
  No observable or statistical differences between experimentals and controls.
 Fertility (silique number and seed fill)
  No observable or statistical differences between experimentals and controls.

Example 5: ME03186

TABLE 5-1

| Construct | Event/Generation | Plant Stage | Assay | Result |
|---|---|---|---|---|
| 35S::674166 | −04/$T_3$ Finale resistant plants | Seedling | Cold Germination | Significant at $p \leq .05$ |
| 35S::674166 | −04/$T_4$ Finale resistant plants | Seedling | Cold Germination | Significant at $p \leq .05$ |
| 35S::674166 | −05/$T_2$ Finale resistant plants | Seedling | Cold Germination | Significant at $p \leq .05$ |
| 35S::674166 | −05/$T_3$ Finale resistant plants | Seedling | Cold Germination | Significant at $p \leq .05$ |

Ectopic expression of Clone 674166 under the control of the 35S promoter results in early germination at 8° C. resulting in larger seedlings after 10 days at 8° C. Plants from Events −04 and −05 which are hemizygous or homozygous for Clone 674166 do not show any negative phenotypes under long-day conditions.

Two Events of ME03186 Showed Significant Early Germination Under Cold Conditions in Both Generations.

Two events, −04 and −05 were significant in two generations at $p \leq 0.05$ using a one-tailed t-test assuming unequal variance (Table 5-2). '−99' signifies that seeds were pooled from several plants.

TABLE 5-2

T-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event -04.
[b]These events were sown twice. The first time was to identify ME03186 as a hit. They were repeated the second time with two generations to identify ME03186 as a candidate.

Two Events of ME03186 Show 3:1 Segregation for Finale™ Resistance.

Event −05 segregated 3:1 (R:S) for Finale™ resistance in the $T_2$ generation. $T_2$ generation seed was not available for Event −04. However, the $T_3$ generation seeds that were pooled from several $T_2$ plants segregated approximately 2:1 in a manner consistent with a single insert (see Table 5-2). Qualitative and Quantitative Analysis of the $T_2$ Plants (Screening for Negative Phenotypes):

Events −04 and −05 of ME03186 exhibited no statistically significant negative phenotypes.

Germination
  No detectable reduction in germination rate.

General morphology/architecture
  Plants appeared wild-type in all instances.

Days to flowering
  No observable or statistical differences between experimentals and controls.

Rosette area 7 days post-bolting

REFERENCES

Hunt et ak, (2001) *Plant Mol Biol* 47: 677-692.
Lu and Hills (2002) *Plant Physiol.* 129:1352-8

Example 6: Clone 1055099 (SEQ ID NO: 46)-ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

|  | p-values | | Avg. Seedling Area | | | Sample No. | | |
| --- | --- | --- | --- | --- | --- | --- | --- | --- |
| Event | Internal[a] | Pooled[b] | Transgenic | Internal | Pooled | Transgenic | Internal | Pooled |
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03 [d] | 0.01488322 | 0.04610112 | 0.0069 | 0.0031 | 0.0054 | 31 | 3 | 83 |
| ME24967-05 [d] | 0.08783497 | 3.0406E−08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 |  | 0.05451794 | 0.0041 | 0.0018 | 0.0054 | 34 | 1 | 83 |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d] These events show significantly improved seedling area for at least internal or pooled controls.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e−5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of 10-5 and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam |
|---|---|---|---|---|---|---|
|  | Ceres CLONE ID no. 30087 | DNA | Arabidopsis thaliana | 1 | 828 |  |
| Ceres CLONE ID no. 30087 | Ceres CLONE ID no. 30087 | PRT | Arabidopsis thaliana | 2 | 164 |  |
| Ceres Clone ID no. 30087 | Ceres CLONE ID no. 947579 | PRT | Brassica napus | 3 | 155 |  |
| Ceres Clone ID no. 30087 | Public GI no. 62526422 | PRT | Brassica napus | 4 | 152 |  |
| Ceres Clone ID no. 30087 | Ceres CLONE ID no. 1606506 | PRT | Parthenium argentatum | 5 | 150 |  |
|  | Ceres CLONE ID no. 30469 | DNA | Artificial Sequence | 6 | 586 |  |
| Ceres CLONE ID no. 30469 | Ceres CLONE ID no. 30469 | PRT | Artificial Sequence | 7 | 78 | Globin |
|  | Ceres CLONE ID no. 30469_FL | DNA | Arabidopsis thaliana | 8 | 483 |  |
| Ceres Clone ID no. 30469 | Ceres CLONE ID no. 30469_FL | PRT | Arabidopsis thaliana | 9 | 160 | Globin |
| Ceres Clone ID no. 30469 | Public GI no. 30909306 | PRT | Raphanus sativus | 10 | 160 | Globin |
| Ceres Clone ID no. 30469 | Public GI no. 37903656 | PRT | Arabidopsis thaliana | 11 | 158 | Globin |
| Ceres Clone ID no. 30469 | Public GI no. 15824736 | PRT | Arabidopsis thaliana | 12 | 163 | Globin |
| Ceres Clone ID no. 30469 | Ceres CLONE ID no. 546001 | PRT | Glycine max | 13 | 161 | Globin |
| Ceres Clone ID no. 30469 | Public GI no. 11095158 | PRT | Glycine max | 14 | 160 | Globin |
| Ceres Clone ID no. 30469 | Public GI no. 12963875 | PRT | Glycine max | 15 | 152 | Globin |
| Ceres Clone ID no. 30469 | Ceres CLONE ID no. 1554560 | PRT | Zea mays | 16 | 165 | Globin |
| Ceres Clone ID no. 30469 | Ceres CLONE ID no. 839727 | PRT | Triticum aestivum | 17 | 162 | Globin |
| Ceres Clone ID no. 30469 | Public GI no. 14701800 | PRT | Triticum aestivum | 18 | 169 | Globin |
|  | Ceres CLONE ID no. 271922 | DNA | Arabidopsis thaliana | 19 | 416 |  |
| Ceres CLONE ID no. 271922 | Ceres CLONE ID no. 271922 | PRT | Arabidopsis thaliana | 20 | 92 | Ribosomal_L37ae; |
| Ceres Clone ID no. 271922 | Public GI no. 4090257 | PRT | Arabidopsis thaliana | 21 | 92 | Ribosomal_L37ae |
| Ceres Clone ID no. 271922 | Public GI no. 4741896 | PRT | Arabidopsis thaliana | 22 | 92 | Ribosomal_L37ae |
| Ceres Clone ID no. 271922 | Ceres CLONE ID no. 36046 | PRT | Arabidopsis thaliana | 23 | 92 | Ribosomal_L37ae |
| Ceres Clone ID no. 271922 | Public GI no. 6016699 | PRT | Arabidopsis thaliana | 24 | 92 | Ribosomal_L37ae |
| Ceres Clone ID no. 271922 | Ceres CLONE ID no. 664936 | PRT | Glycine max | 25 | 92 | Ribosomal_L37ae |
| Ceres Clone ID no. 271922 | Ceres CLONE ID no. 658438 | PRT | Glycine max | 26 | 92 | Ribosomal_L37ae |
| Ceres Clone ID no. 271922 | Ceres CLONE ID no. 1049262 | PRT | Glycine max | 27 | 92 | Ribosomal_L37ae |
| Ceres Clone ID no. 271922 | Ceres CLONE ID no. 632613 | PRT | Triticum aestivum | 28 | 92 | Ribosomal_L37ae |
| Ceres Clone ID no. 271922 | Ceres CLONE ID no. 1390976 | PRT | Zea mays | 29 | 92 | Ribosomal_L37ae |
| Ceres Clone ID no. 271922 | Ceres CLONE ID no. 1457185 | PRT | Zea mays | 30 | 92 | Ribosomal_L37ae |
| Ceres Clone ID no. 271922 | Public GI no. 56202147 | PRT | Zea mays | 31 | 92 | Ribosomal_L37ae |
| Ceres Clone ID no. 271922 | Public GI no. 58578274 | PRT | Zea mays | 32 | 92 | Ribosomal_L37ae |
|  | Ceres CLONE ID no. 2403_FL | DNA | Arabidopsis thaliana | 33 | 632 |  |
| Ceres CLONE ID no. 2403 | Ceres CLONE ID no. 2403_FL | PRT | Arabidopsis thaliana | 34 | 154 | ubiquitin; |
| Ceres CLONE ID no. 2403 | Ceres CLONE ID no. 2403_FL | PRT | Arabidopsis thaliana | 34 | 154 | ubiquitin; |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 522921 | PRT | Glycine max | 36 | 154 | ubiquitin |

TABLE 7-continued

| | | | | | | |
|---|---|---|---|---|---|---|
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 513071 | PRT | Glycine max | 38 | 188 | ubiquitin |
| Ceres Clone ID no. 2403 | Ceres CLONE ID no. 513071 | PRT | Glycine max | 38 | 188 | ubiquitin |
| | Ceres CLONE ID no. 2403 | DNA | Artificial Sequence | 39 | 620 | |
| Ceres CLONE ID no. 2403 | Ceres CLONE ID no. 2403 | PRT | Artificial Sequence | 40 | 33 | ubiquitin; |
| | Ceres CLONE ID no. 674166 | DNA | Glycine max | 41 | 1106 | |
| Ceres CLONE ID no. 674166 | Ceres CLONE ID no. 674166 | PRT | Glycine max | 42 | 210 | AP2; |
| Ceres Clone ID no. 674166 | Public GI no. 12322345 | PRT | Glycine max | 43 | 225 | AP2 |
| Ceres Clone ID no. 674166 | Ceres CLONE ID no. 975672 | PRT | Brassica napus | 44 | 215 | AP2 |
| Ceres Clone ID no. 674166 | Ceres CLONE ID no. 273307 | PRT | Zea mays | 45 | 211 | AP2 |
| Ceres Clone ID no. 674166 | Ceres CLONE ID no. 1055099 | PRT | Triticum aestivum | 46 | 194 | AP2 |
| | Ceres ANNOT ID no. 1441430 | DNA | Populus balsamifera subsp. trichocarpa | 47 | 660 | |
| Ceres CLONE ID no. 674166 | Ceres ANNOT ID no. 1441430 | PRT | Populus balsamifera subsp. trichocarpa | 48 | 219 | AP2 |
| | Ceres CLONE ID no. 1240330 | DNA | Glycine max | 49 | 985 | |
| Ceres CLONE ID no. 674166 | Ceres CLONE ID no. 1240330 | PRT | Glycine max | 50 | 222 | AP2 |
| | Ceres CLONE ID no. 1382611 | DNA | Zea mays | 51 | 726 | |
| Ceres CLONE ID no. 30087 | Ceres CLONE ID no. 1382611 | PRT | Zea mays | 52 | 156 | |
| | Ceres CLONE ID no. 1627907 | DNA | Papaver somniferum | 53 | 580 | |
| Ceres CLONE ID no. 271922 | Ceres CLONE ID no. 1627907 | PRT | Papaver somniferum | 54 | 92 | Ribosomal_L37ae |
| | Ceres CLONE ID no. 1761125 | DNA | Panicum virgatum | 55 | 983 | |
| Ceres CLONE ID no. 674166 | Ceres CLONE ID no. 1761125 | PRT | Panicum virgatum | 56 | 192 | AP2 |
| | Ceres CLONE ID no. 1783890 | DNA | Panicum virgatum | 57 | 594 | |
| Ceres CLONE ID no. 271922 | Ceres CLONE ID no. 1783890 | PRT | Panicum virgatum | 58 | 92 | Ribosomal_L37ae |
| | Ceres CLONE ID no. 1802327 | DNA | Panicum virgatum | 59 | 880 | |
| Ceres Clone ID no. 30469 | Ceres CLONE ID no. 1802327 | PRT | Panicum virgatum | 60 | 162 | Globin |
| | Ceres CLONE ID no. 1838364 | DNA | Gossypium hirsutum | 61 | 1017 | |
| Ceres CLONE ID no. 674166 | Ceres CLONE ID no. 1838364 | PRT | Gossypium hirsutum | 62 | 246 | AP2 |
| | Ceres CLONE ID no. 1876458 | DNA | Panicum virgatum | 63 | 708 | |
| Ceres Clone ID no. 30469 | Ceres CLONE ID no. 1876458 | PRT | Panicum virgatum | 64 | 162 | Globin |
| | Ceres CLONE ID no. 1879148 | DNA | Panicum virgatum | 65 | 712 | |
| Ceres Clone ID no. 30469 | Ceres CLONE ID no. 1879148 | PRT | Panicum virgatum | 66 | 164 | Globin |
| | Ceres CLONE ID no. 1884696 | DNA | Gossypium hirsutum | 67 | 1129 | |
| Ceres CLONE ID no. 2403 | Ceres CLONE ID no. 1884696 | PRT | Gossypium hirsutum | 68 | 153 | ubiquitin |
| Ceres CLONE ID no. 2403 | Ceres CLONE ID no. 1884696 | PRT | Gossypium hirsutum | 68 | 153 | ubiquitin |
| | Ceres CLONE ID no. 1916866 | DNA | Gossypium hirsutum | 69 | 679 | |
| Ceres Clone ID no. 30469 | Ceres CLONE ID no. 1916866 | PRT | Gossypium hirsutum | 70 | 163 | Globin |
| | Ceres CLONE ID no. 1950105 | DNA | Panicum virgatum | 71 | 1003 | |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| | Ceres CLONE ID no. 1990746 | DNA | Panicum virgatum | 73 | 724 | |
| Ceres Clone ID no. 30469 | Ceres CLONE ID no. 1990746 | PRT | Panicum virgatum | 74 | 164 | Globin |
| | Ceres CLONE ID no. 2007485 | DNA | Panicum virgatum | 75 | 696 | |
| Ceres CLONE ID no. 674166 | Ceres CLONE ID no. 2007485 | PRT | Panicum virgatum | 76 | 201 | AP2 |
| | Ceres CLONE ID no. 2033803 | DNA | Panicum virgatum | 77 | 698 | |
| Ceres Clone ID no. 30469 | Ceres CLONE ID no. 2033803 | PRT | Panicum virgatum | 78 | 156 | Globin |
| | Ceres CLONE ID no. 2034916 | DNA | Panicum virgatum | 79 | 724 | |
| Ceres CLONE ID no. 2403 | Ceres CLONE ID no. 2034916 | PRT | Panicum virgatum | 80 | 213 | ubiquitin |

TABLE 7-continued

| Ceres CLONE ID no. 2403 | Ceres CLONE ID no. 2034916 | PRT | Panicum virgatum | 80 | 213 | ubiquitin |
|---|---|---|---|---|---|---|
| Ceres CLONE ID no. 2403 | Ceres CLONE ID no. 2034916 | PRT | Panicum virgatum | 80 | 213 | ubiquitin |
| | Ceres CLONE ID no. 651581 | DNA | Glycine max | 81 | 1194 | |
| Ceres CLONE ID no. 674166 | Ceres CLONE ID no. 651581 | PRT | Glycine max | 82 | 224 | AP2 |
| Ceres CLONE ID no. 674166 | Public GI ID no. 125550159 | PRT | Oryza sativa subsp. indica | 83 | 184 | AP2 |
| Ceres CLONE ID no. 674166 | Public GI ID no. 15223609 | PRT | Arabidopsis thaliana | 84 | 225 | AP2 |
| Ceres CLONE ID no. 30087 | Public GI ID no. 30683885 | PRT | Arabidopsis thaliana | 85 | 164 | |
| Ceres CLONE ID no. 674166 | Public GI ID no. 56384582 | PRT | Pisum sativum | 86 | 218 | AP2 |
| Ceres CLONE ID no. 674166 | Public GI ID no. 57012880 | PRT | Nicotiana tabacum | 87 | 225 | AP2 |
| Ceres Clone ID no. 30469 | Public GI ID no. 62548111 | PRT | Gossypium hirsutum | 88 | 163 | Globin |
| Ceres CLONE ID no. 2403 | Ceres CLONE ID no. 100021733 | PRT | Gossypium hirsutum | 89 | 153 | ubiquitin |
| Ceres CLONE ID no. 2403 | Ceres CLONE ID no. 100021733 | PRT | Gossypium hirsutum | 89 | 153 | ubiquitin |
| | Ceres CLONE ID no. 947579 | DNA | Brassica napus | 90 | 775 | |
| | Ceres CLONE ID no. 36046 | DNA | Arabidopsis thaliana | 91 | 1032 | |
| | Ceres CLONE ID no. 1606506 | DNA | Parthenium argentatum | 92 | 492 | |
| | Ceres CLONE ID no. 546001 | DNA | Glycine max | 93 | 970 | |
| | Ceres CLONE ID no. 1554560 | DNA | Zea mays | 94 | 604 | |
| | Ceres CLONE ID no. 839727 | DNA | Triticum aestivum | 95 | 846 | |
| | Ceres CLONE ID no. 664936 | DNA | Glycine max | 96 | 440 | |
| | Ceres CLONE ID no. 658438 | DNA | Glycine max | 97 | 463 | |
| | Ceres CLONE ID no. 1049262 | DNA | Glycine max | 98 | 458 | |
| | Ceres CLONE ID no. 632613 | DNA | Triticum aestivum | 99 | 600 | |
| | Ceres CLONE ID no. 1390976 | DNA | Zea mays | 100 | 546 | |
| | Ceres CLONE ID no. 1457185 | DNA | Zea mays | 101 | 550 | |
| | Ceres CLONE ID no. 1482731 | DNA | Zea mays | 102 | 668 | |
| | Ceres CLONE ID no. 522921 | DNA | Glycine max | 103 | 752 | |
| | Ceres CLONE ID no. 1036726 | DNA | Brassica napus | 104 | 484 | |
| | Ceres CLONE ID no. 513071 | DNA | Glycine max | 105 | 580 | |
| | Ceres CLONE ID no. 975672 | DNA | Brassica napus | 106 | 987 | |
| | Ceres CLONE ID no. 273307 | DNA | Zea mays | 107 | 1034 | |
| | Ceres CLONE ID no. 1055099 | DNA | Triticum aestivum | 108 | 911 | |
| Ceres Clone ID no. 30469 | Ceres GI ID no. GI_15226675 | PRT | Arabidopsis thaliana | 109 | 160 | Globin |
| | Ceres Promoter 21876 | DNA | Arabidopsis thaliana | 110 | 1823 | |
| | Ceres Promoter PT0668 | DNA | Arabidopsis thaliana | 111 | 1000 | |
| | Ceres Promoter PT0535 | DNA | Arabidopsis thaliana | 112 | 1000 | |
| | Ceres Promoter PT0585 | DNA | Arabidopsis thaliana | 113 | 999 | |
| | Ceres Promoter PT0613 | DNA | Arabidopsis thaliana | 114 | 1000 | |
| | Ceres Promoter PT0625 | DNA | Arabidopsis thaliana | 115 | 351 | |
| | Ceres Promoter PT0633 | DNA | Arabidopsis thaliana | 116 | 1022 | |
| | Ceres Promoter PT0650 | DNA | Arabidopsis thaliana | 117 | 1000 | |
| | Ceres Promoter PT0660 | DNA | Arabidopsis thaliana | 118 | 998 | |
| | Ceres Promoter PT0665 | DNA | Arabidopsis thaliana | 119 | 1000 | |
| | Ceres Promoter PT0672 | DNA | Arabidopsis thaliana | 120 | 999 | |
| | Ceres Promoter PT0676 | DNA | Arabidopsis thaliana | 121 | 1000 | |
| | Ceres Promoter PT0678 | DNA | Arabidopsis thaliana | 122 | 998 | |
| | Ceres Promoter PT0683 | DNA | Arabidopsis thaliana | 123 | 1000 | |
| | Ceres Promoter PT0688 | DNA | Arabidopsis thaliana | 124 | 1000 | |
| | Ceres Promoter PT0695 | DNA | Arabidopsis thaliana | 125 | 1000 | |
| | Ceres Promoter PT0708 | DNA | Arabidopsis thaliana | 126 | 1000 | |
| | Ceres Promoter PT0710 | DNA | Arabidopsis thaliana | 127 | 1000 | |
| | Ceres Promoter PT0723 | DNA | Arabidopsis thaliana | 128 | 1002 | |
| | Ceres Promoter PT0740 | DNA | Arabidopsis thaliana | 129 | 1001 | |
| | Ceres Promoter PT0743 | DNA | Arabidopsis thaliana | 130 | 1024 | |
| | Ceres Promoter PT0758 | DNA | Arabidopsis thaliana | 131 | 1000 | |
| | Ceres Promoter PT0829 | DNA | Arabidopsis thaliana | 132 | 921 | |
| | Ceres Promoter PT0837 | DNA | Arabidopsis thaliana | 133 | 763 | |
| | Ceres Promoter PT0838 | DNA | Arabidopsis thaliana | 134 | 751 | |
| | Ceres Promoter PT0848 | DNA | Arabidopsis thaliana | 135 | 669 | |
| | Ceres Promoter PT0863 | DNA | Arabidopsis thaliana | 136 | 702 | |
| | Ceres Promoter PT0879 | DNA | Arabidopsis thaliana | 137 | 435 | |
| | Ceres Promoter PT0886 | DNA | Arabidopsis thaliana | 138 | 397 | |
| | Ceres Promoter YP0007 | DNA | Arabidopsis thaliana | 139 | 1024 | |
| | Ceres Promoter YP0008 | DNA | Arabidopsis thaliana | 140 | 1000 | |
| | Ceres Promoter YP0019 | DNA | Arabidopsis thaliana | 141 | 999 | |
| | Ceres Promoter YP0028 | DNA | Arabidopsis thaliana | 142 | 1024 | |
| | Ceres Promoter YP0039 | DNA | Arabidopsis thaliana | 143 | 1024 | |
| | Ceres Promoter YP0050 | DNA | Arabidopsis thaliana | 144 | 1024 | |

TABLE 7-continued

|  |  |  |  |  |  |  |
|---|---|---|---|---|---|---|
|  | Ceres Promoter YP0086 | DNA | *Arabidopsis thaliana* | 145 | 999 |  |
|  | Ceres Promoter YP0088 | DNA | *Arabidopsis thaliana* | 146 | 1024 |  |
|  | Ceres Promoter YP0092 | DNA | *Arabidopsis thaliana* | 147 | 1024 |  |
|  | Ceres Promoter YP0096 | DNA | *Arabidopsis thaliana* | 148 | 1020 |  |
|  | Ceres Promoter YP0097 | DNA | *Arabidopsis thaliana* | 149 | 1000 |  |
|  | Ceres Promoter YP0101 | DNA | *Arabidopsis thaliana* | 150 | 1004 |  |
|  | Ceres Promoter YP0102 | DNA | *Arabidopsis thaliana* | 151 | 1000 |  |
|  | Ceres Promoter YP0103 | DNA | *Arabidopsis thaliana* | 152 | 1004 |  |
|  | Ceres Promoter YP0107 | DNA | *Arabidopsis thaliana* | 153 | 1003 |  |
|  | Ceres Promoter YP0110 | DNA | *Arabidopsis thaliana* | 154 | 1024 |  |
|  | Ceres Promoter YP0111 | DNA | *Arabidopsis thaliana* | 155 | 1024 |  |
|  | Ceres Promoter YP0115 | DNA | *Arabidopsis thaliana* | 156 | 996 |  |
|  | Ceres Promoter YP0117 | DNA | *Arabidopsis thaliana* | 157 | 1024 |  |
|  | Ceres Promoter YP0119 | DNA | *Arabidopsis thaliana* | 158 | 1000 |  |
|  | Ceres Promoter YP0120 | DNA | *Arabidopsis thaliana* | 159 | 999 |  |
|  | Ceres Promoter YP0121 | DNA | *Arabidopsis thaliana* | 160 | 999 |  |
|  | Ceres Promoter YP0128 | DNA | *Arabidopsis thaliana* | 161 | 1004 |  |
|  | Ceres Promoter YP0137 | DNA | *Arabidopsis thaliana* | 162 | 1001 |  |
|  | Ceres Promoter YP0143 | DNA | *Arabidopsis thaliana* | 163 | 1001 |  |
|  | Ceres Promoter YP0144 | DNA | *Arabidopsis thaliana* | 164 | 1003 |  |
|  | Ceres Promoter YP0156 | DNA | *Arabidopsis thaliana* | 165 | 1004 |  |
|  | Ceres Promoter YP0158 | DNA | *Arabidopsis thaliana* | 166 | 1000 |  |
|  | Ceres Promoter YP0188 | DNA | *Arabidopsis thaliana* | 167 | 1005 |  |
|  | Ceres Promoter YP0190 | DNA | *Arabidopsis thaliana* | 168 | 1002 |  |
|  | Ceres Promoter YP0212 | DNA | *Arabidopsis thaliana* | 169 | 995 |  |
|  | Ceres Promoter YP0214 | DNA | *Arabidopsis thaliana* | 170 | 1024 |  |
|  | Ceres Promoter YP0263 | DNA | *Arabidopsis thaliana* | 171 | 911 |  |
|  | Ceres Promoter YP0275 | DNA | *Arabidopsis thaliana* | 172 | 999 |  |
|  | Ceres Promoter YP0285 | DNA | *Arabidopsis thaliana* | 173 | 981 |  |
|  | Ceres Promoter YP0286 | DNA | *Arabidopsis thaliana* | 174 | 996 |  |
|  | Ceres Promoter YP0337 | DNA | *Arabidopsis thaliana* | 175 | 1000 |  |
|  | Ceres Promoter YP0356 | DNA | *Arabidopsis thaliana* | 176 | 1000 |  |
|  | Ceres Promoter YP0374 | DNA | *Arabidopsis thaliana* | 177 | 1000 |  |
|  | Ceres Promoter YP0377 | DNA | *Arabidopsis thaliana* | 178 | 998 |  |
|  | Ceres Promoter YP0380 | DNA | *Arabidopsis thaliana* | 179 | 999 |  |
|  | Ceres Promoter YP0381 | DNA | *Arabidopsis thaliana* | 180 | 1000 |  |
|  | Ceres Promoter YP0384 | DNA | *Arabidopsis thaliana* | 181 | 999 |  |
|  | Ceres Promoter YP0385 | DNA | *Arabidopsis thaliana* | 182 | 998 |  |
|  | Ceres Promoter YP0396 | DNA | *Arabidopsis thaliana* | 183 | 1000 |  |
|  | Ceres Promoter p13879 | DNA | *Arabidopsis thaliana* | 184 | 1514 |  |
|  | Ceres Promoter p326 | DNA | *Arabidopsis thaliana* | 185 | 1954 |  |
|  | Ceres Promoter p32449 | DNA | *Arabidopsis thaliana* | 186 | 2016 |  |
|  | Ceres Promoter PD1367 | DNA | *Arabidopsis thaliana* | 187 | 667 |  |
|  | Ceres Promoter p530c10 | DNA | *Oryza sativa* | 188 | 1836 |  |
|  | Ceres Promoter pOsFIE2-2 | DNA | *Oryza sativa* | 189 | 3000 |  |
|  | Ceres Promoter pOsMEA | DNA | *Oryza sativa* | 190 | 2023 |  |
|  | Ceres Promoter pOsYp102 | DNA | *Oryza sativa* | 191 | 2034 |  |
|  | Ceres Promoter pOsYp285 | DNA | *Oryza sativa* | 192 | 1877 |  |
|  | Ceres Promoter PT0565 | DNA | *Arabidopsis thaliana* | 193 | 1000 |  |
|  | Ceres Promoter YP0015 | DNA | *Arabidopsis thaliana* | 194 | 999 |  |
|  | Ceres Promoter YP0087 | DNA | *Arabidopsis thaliana* | 195 | 999 |  |
|  | Ceres Promoter YP0093 | DNA | *Arabidopsis thaliana* | 196 | 1000 |  |
|  | Ceres Promoter YP0108 | DNA | *Arabidopsis thaliana* | 197 | 999 |  |
|  | Ceres Promoter YP0022 | DNA | *Arabidopsis thaliana* | 198 | 999 |  |
|  | Ceres Promoter YP0080 | DNA | *Arabidopsis thaliana* | 199 | 999 |  |
|  | Ceres Promoter PR0924 | DNA | *Arabidopsis thaliana* | 200 | 3000 |  |
|  | Ceres Promoter YP0388 | DNA | *Arabidopsis thaliana* | 201 | 1000 |  |
|  | Ceres Promoter PD0901 | DNA | *Arabidopsis thaliana* | 202 | 283 |  |
|  | Ceres Promoter PT0623 | DNA | *Arabidopsis thaliana* | 203 | 1000 |  |
| Ceres Clone ID no. 2403 | Truncated version of Ceres CLONE ID no. 100021733 | PRT | Artificial Sequence | 204 | 33 | ubiquitin |
| Ceres Clone ID no. 2403 | Truncated version of Ceres CLONE ID no. 1036726 | PRT | Artificial Sequence | 205 | 33 | ubiquitin |
| Ceres Clone ID no. 2403 | Truncated version of Ceres CLONE ID no. 1482731 | PRT | Artificial Sequence | 206 | 33 | ubiquitin |
| Ceres Clone ID no. 30469 | Truncated Version of Ceres CLONE ID no. 1554560 | PRT | Artificial Sequence | 207 | 80 | Globin |
| Ceres Clone ID no. 30469 | Truncated Version of Ceres CLONE ID no. 1802327 | PRT | Artificial Sequence | 208 | 77 | Globin |
| Ceres Clone ID no. 30469 | Truncated Version of Ceres CLONE ID no. 1876458 | PRT | Artificial Sequence | 209 | 77 | Globin |
| Ceres Clone ID no. 30469 | Truncated Version of Ceres CLONE ID no. 1879148 | PRT | Artificial Sequence | 210 | 79 | Globin |
| Ceres Clone ID no. 2403 | Truncated version of Ceres CLONE ID no. 1884696 | PRT | Artificial Sequence | 211 | 33 | ubiquitin |
| Ceres Clone ID no. 30469 | Truncated Version of Ceres CLONE ID no. 1916866 | PRT | Artificial Sequence | 212 | 76 | Globin |
| Ceres Clone ID no. 2403 | Truncated version of Ceres CLONE ID no. 1950105 | PRT | Artificial Sequence | 213 | 33 | ubiquitin |

TABLE 7-continued

| | | | | | | | |
|---|---|---|---|---|---|---|---|
| Ceres Clone ID no. 30469 | Truncated Version of Ceres CLONE ID no. 1990746 | PRT | Artificial Sequence | 214 | 79 | Globin | |
| Ceres Clone ID no. 30469 | Truncated Version of Ceres CLONE ID no. 2033803 | PRT | Artificial Sequence | 215 | 79 | Globin | |
| Ceres Clone ID no. 2403 | Truncated version of Ceres CLONE ID no. 2034916 | PRT | Artificial Sequence | 216 | 33 | ubiquitin | |
| Ceres Clone ID no. 2403 | Truncated version of Ceres CLONE ID no. 513071 | PRT | Artificial Sequence | 217 | 33 | ubiquitin | |
| Ceres Clone ID no. 2403 | Truncated version of Ceres CLONE ID no. 522921 | PRT | Artificial Sequence | 218 | 33 | ubiquitin | |
| Ceres Clone ID no. 30469 | Truncated Version of Ceres CLONE ID no. 546001 | PRT | Artificial Sequence | 219 | 76 | Globin | |
| Ceres Clone ID no. 30469 | Truncated Version of Ceres CLONE ID no. 651581 | PRT | Artificial Sequence | 220 | 76 | Globin | |
| Ceres Clone ID no. 30469 | Truncated Version of Ceres CLONE ID no. 839727 | PRT | Artificial Sequence | 221 | 77 | Globin | |
| Ceres Clone ID no. 30469 | Truncated Version of Public GI ID no. 11095158 | PRT | Artificial Sequence | 222 | 76 | Globin | |
| Ceres Clone ID no. 30469 | Truncated Version of Public GI ID no. 12963875 | PRT | Artificial Sequence | 223 | 71 | Globin | |
| Ceres Clone ID no. 30469 | Truncated Version of Public GI ID no. 14701800 | PRT | Artificial Sequence | 224 | 84 | Globin | |
| Ceres Clone ID no. 30469 | Truncated Version of Public GI ID no. 15226675 | PRT | Artificial Sequence | 225 | 76 | Globin | |
| Ceres Clone ID no. 30469 | Truncated Version of Public GI ID no. 15824736 | PRT | Artificial Sequence | 226 | 76 | Globin | |
| Ceres Clone ID no. 30469 | Truncated Version of Public GI ID no. 30909306 | PRT | Artificial Sequence | 227 | 76 | Globin | |
| Ceres Clone ID no. 30469 | Truncated Version of Public GI ID no. 37903656 | PRT | Artificial Sequence | 228 | 73 | Globin | |
| Ceres Clone ID no. 30469 | Truncated Version of Public GI ID no. 62548111 | PRT | Artificial Sequence | 229 | 76 | Globin | |

| Query Identifier | Functional Homolog | Pfam Description | Start | End | Profile | HMM Bit Score | FL_Profile | FL_Score |
|---|---|---|---|---|---|---|---|---|
| Ceres CLONE ID no. 30087 | Ceres CLONE ID no. 30087 | | | | Y | | | |
| Ceres Clone ID no. 30087 | Ceres CLONE ID no. 947579 | | | | Y | | | |
| Ceres Clone ID no. 30087 | Public GI no. 62526422 | | | | | | | |
| Ceres Clone ID no. 30087 | Ceres CLONE ID no. 1606506 | | | | Y | | | |
| Ceres CLONE ID no. 30469 | Ceres CLONE ID no. 30469 | Globin | 13 | 74 | Y | 184.6 | | 66 |
| Ceres Clone ID no. 30469 | Ceres CLONE ID no. 30469_FL | Globin | 13 | 152 | | 184.6 | Y | 404.9 |
| Ceres Clone ID no. 30469 | Public GI no. 30909306 | Globin | 13 | 152 | | 185.7 | Y | 410.4 |
| Ceres Clone ID no. 30469 | Public GI no. 37903656 | Globin | 10 | 149 | | 172.6 | | 387.2 |
| Ceres Clone ID no. 30469 | Public GI no. 15824736 | Globin | 13 | 152 | | 184.2 | | 405.4 |
| Ceres Clone ID no. 30469 | Ceres CLONE ID no. 546001 | Globin | 13 | 152 | | 182.8 | Y | 402.3 |
| Ceres Clone ID no. 30469 | Public GI no. 11095158 | Globin | 13 | 152 | | 167.8 | | 387.2 |
| Ceres Clone ID no. 30469 | Public GI no. 12963875 | Globin | 8 | 147 | | 145.8 | | 337.1 |
| Ceres Clone ID no. 30469 | Ceres CLONE ID no. 1554560 | Globin | 17 | 157 | | 185.7 | Y | 404.5 |
| Ceres Clone ID no. 30469 | Ceres CLONE ID no. 839727 | Globin | 14 | 154 | | 187.8 | Y | 415.2 |
| Ceres Clone ID no. 30469 | Public GI no. 14701800 | Globin | 21 | 161 | | 170.1 | | 386.9 |
| Ceres CLONE ID no. 271922 | Ceres CLONE ID no. 271922 | Ribosomal L37ae protein family | 2 | 91 | Y | 266.3 | | |
| Ceres Clone ID no. 271922 | Public GI no. 4090257 | Ribosomal L37ae protein family | 2 | 91 | | 265.8 | | |

TABLE 7-continued

| Ceres Clone ID no. 271922 | Public GI no. 4741896 | Ribosomal L37ae protein family | 2 | 91 | | 264 | | |
|---|---|---|---|---|---|---|---|---|
| Ceres Clone ID no. 271922 | Ceres CLONE ID no. 36046 | Ribosomal L37ae protein family | 2 | 91 | | 257.8 | | |
| Ceres Clone ID no. 271922 | Public GI no. 6016699 | Ribosomal L37ae protein family | 2 | 91 | | 257.4 | | |
| Ceres Clone ID no. 271922 | Ceres CLONE ID no. 664936 | Ribosomal L37ae protein family | 2 | 91 | Y | 268.8 | | |
| Ceres Clone ID no. 271922 | Ceres CLONE ID no. 658438 | Ribosomal L37ae protein family | 2 | 91 | | 269 | | |
| Ceres Clone ID no. 271922 | Ceres CLONE ID no. 1049262 | Ribosomal L37ae protein family | 2 | 91 | | 268.9 | | |
| Ceres Clone ID no. 271922 | Ceres CLONE ID no. 632613 | Ribosomal L37ae protein family | 2 | 91 | Y | 269 | | |
| Ceres Clone ID no. 271922 | Ceres CLONE ID no. 1390976 | Ribosomal L37ae protein family | 2 | 91 | Y | 269 | | |
| Ceres Clone ID no. 271922 | Ceres CLONE ID no. 1457185 | Ribosomal L37ae protein family | 2 | 91 | | 269 | | |
| Ceres Clone ID no. 271922 | Public GI no. 56202147 | Ribosomal L37ae protein family | 2 | 91 | | 269 | | |
| Ceres Clone ID no. 271922 | Public GI no. 58578274 | Ribosomal L37ae protein family | 2 | 91 | | 267.2 | | |
| Ceres CLONE ID no. 2403 | Ceres CLONE ID no. 2403_FL | Ubiquitin family | 1 | 74 | | 118.7 | | 416.2 |
| Ceres CLONE ID no. 2403 | Ceres CLONE ID no. 2403_FL | Ubiquitin family | 77 | 150 | | 118.7 | Y | 416.2 |
| Ceres Clone ID no. 2403 | Ceres CLONE ID no. 1482731 | Ubiquitin family | 1 | 74 | | 118.3 | Y | 417 |
| Ceres Clone ID no. 2403 | Ceres CLONE ID no. 1482731 | Ubiquitin family | 77 | 150 | | 118.3 | Y | 417 |
| Ceres Clone ID no. 2403 | Ceres CLONE ID no. 522921 | Ubiquitin family | 1 | 74 | | 118.7 | Y | 418.4 |
| Ceres Clone ID no. 2403 | Ceres CLONE ID no. 522921 | Ubiquitin family | 77 | 150 | | 118.7 | Y | 418.4 |
| Ceres Clone ID no. 2403 | Ceres CLONE ID no. 1036726 | Ubiquitin family | 1 | 74 | | 118.7 | Y | 384.4 |
| Ceres Clone ID no. 2403 | Ceres CLONE ID no. 1036726 | Ubiquitin family | 77 | 142 | | 118.7 | Y | 384.4 |
| Ceres Clone ID no. 2403 | Ceres CLONE ID no. 513071 | Ubiquitin family | 1 | 74 | | 114.3 | | 408.6 |
| Ceres Clone ID no. 2403 | Ceres CLONE ID no. 513071 | Ubiquitin family | 77 | 150 | | 114.3 | | 408.6 |
| Ceres CLONE ID no. 2403 | Ceres CLONE ID no. 2403 | Ubiquitin family | 1 | 33 | Y | 87.6 | | −83.1 |
| Ceres CLONE ID no. 674166 | Ceres CLONE ID no. 674166 | AP2 domain | 26 | 89 | Y | 491.8 | | |
| Ceres Clone ID no. 674166 | Public GI no. 12322345 | AP2 domain | 26 | 89 | | 522.4 | | |
| Ceres Clone ID no. 674166 | Ceres CLONE ID no. 975672 | AP2 domain | 21 | 84 | Y | 481.7 | | |
| Ceres Clone ID no. 674166 | Ceres CLONE ID no. 273307 | AP2 domain | 17 | 80 | Y | 419.7 | | |

TABLE 7-continued

| | | | | | | | | |
|---|---|---|---|---|---|---|---|---|
| Ceres Clone ID no. 674166 | Ceres CLONE ID no. 1055099 | AP2 domain | 20 | 83 | Y | 358.4 | | |
| Ceres CLONE ID no. 674166 | Ceres ANNOT ID no. 1441430 Ceres ANNOT ID no. 1441430 | AP2 domain | 29 | 92 | Y | 504.4 | | |
| Ceres CLONE ID no. 674166 | Ceres CLONE ID no. 1240330 Ceres CLONE ID no. 1240330 | AP2 domain | 24 | 87 | | 483.3 | | |
| Ceres CLONE ID no. 30087 | Ceres CLONE ID no. 1382611 Ceres CLONE ID no. 1382611 | | | | Y | | | |
| Ceres CLONE ID no. 271922 | Ceres CLONE ID no. 1627907 Ceres CLONE ID no. 1627907 | Ribosomal L37ae protein family | 2 | 91 | Y | 268.1 | | |
| Ceres CLONE ID no. 674166 | Ceres CLONE ID no. 1761125 Ceres CLONE ID no. 1761125 | AP2 domain | 13 | 76 | Y | 363 | | |
| Ceres CLONE ID no. 271922 | Ceres CLONE ID no. 1783890 Ceres CLONE ID no. 1783890 | Ribosomal L37ae protein family | 2 | 91 | Y | 269 | | |
| Ceres Clone ID no. 30469 | Ceres CLONE ID no. 1802327 Ceres CLONE ID no. 1802327 | Globin | 14 | 154 | | 191.4 | Y | 417.9 |
| Ceres CLONE ID no. 674166 | Ceres CLONE ID no. 1838364 Ceres CLONE ID no. 1838364 | AP2 domain | 28 | 91 | Y | 484.1 | | |
| Ceres Clone ID no. 30469 | Ceres CLONE ID no. 1876458 Ceres CLONE ID no. 1876458 | Globin | 14 | 154 | | 191.9 | | 415.3 |
| Ceres Clone ID no. 30469 | Ceres CLONE ID no. 1879148 Ceres CLONE ID no. 1879148 | Globin | 16 | 156 | | 185.7 | | 411.2 |
| Ceres CLONE ID no. 2403 | Ceres CLONE ID no. 1884696 Ceres CLONE ID no. 1884696 | Ubiquitin family | 1 | 74 | | 175.2 | Y | 408 |
| Ceres CLONE ID no. 2403 | Ceres CLONE ID no. 1884696 | Ubiquitin family | 77 | 150 | | 175.2 | Y | 408 |
| Ceres Clone ID no. 30469 | Ceres CLONE ID no. 1916866 Ceres CLONE ID no. 1916866 | Globin | 13 | 152 | | 188.3 | Y | 409.8 |
| Ceres CLONE ID no. 2403 | Ceres CLONE ID no. 1950105 Ceres CLONE ID no. 1950105 | Ubiquitin family | 1 | 74 | | 262.8 | | 504.1 |
| Ceres CLONE ID no. 2403 | Ceres CLONE ID no. 1950105 | Ubiquitin family | 77 | 150 | | 262.8 | | 504.1 |
| Ceres CLONE ID no. 2403 | Ceres CLONE ID no. 1950105 | Ubiquitin family | 153 | 226 | | 262.8 | | 504.1 |
| Ceres Clone ID no. 30469 | Ceres CLONE ID no. 1990746 Ceres CLONE ID no. 1990746 | Globin | 16 | 156 | | 184.9 | | 405.6 |
| Ceres CLONE ID no. 674166 | Ceres CLONE ID no. 2007485 Ceres CLONE ID no. 2007485 | AP2 domain | 17 | 80 | | 369.2 271.2 | | |
| Ceres Clone ID no. 30469 | Ceres CLONE ID no. 2033803 Ceres CLONE ID no. 2033803 | Globin | 16 | 148 | | 184.9 | | 369.2 |
| Ceres CLONE ID no. 2403 | Ceres CLONE ID no. 2034916 Ceres CLONE ID no. 2034916 | Ubiquitin family | 1 | 74 | | 259.2 | Y | 460.4 |
| Ceres CLONE ID no. 2403 | Ceres CLONE ID no. 2034916 | Ubiquitin family | 77 | 150 | | 259.2 | Y | 460.4 |
| Ceres CLONE ID no. 2403 | Ceres CLONE ID no. 2034916 | Ubiquitin family | 153 | 213 | | 259.2 | Y | 460.4 |
| Ceres CLONE ID no. 674166 | Ceres CLONE ID no. 651581 Ceres CLONE ID no. 651581 | AP2 domain | 24 | 87 | | 469.5 | | |
| Ceres CLONE ID no. 674166 | Public GI ID no. 125550159 | AP2 domain | 7 | 70 | Y | 344 | | |
| Ceres CLONE ID no. 674166 | Public GI ID no. 15223609 | AP2 domain | 26 | 89 | Y | 522.4 | | |
| Ceres CLONE ID no. 30087 | Public GI ID no. 30683885 | | | | | | | |
| Ceres CLONE ID no. 674166 | Public GI ID no. 56384582 | AP2 domain | 21 | 84 | Y | 484.2 | | |
| Ceres CLONE ID no. 674166 | Public GI ID no. 57012880 | AP2 domain | 26 | 89 | Y | 521.4 | | |

TABLE 7-continued

| Ceres Clone ID no. 30469 | Public GI ID no. 62548111 | Globin | 13 | 152 | 188.3 | 409.8 |
|---|---|---|---|---|---|---|
| Ceres CLONE ID no. 2403 | Ceres CLONE ID no. 100021733 | Ubiquitin family | 1 | 74 | 175.2 | 410.3 |
| Ceres CLONE ID no. 2403 | Ceres CLONE ID no. 100021733 | Ubiquitin family | 77 | 150 | 175.2 | 410.3 |
| | Ceres CLONE ID no. 947579 | | | | | |
| | Ceres CLONE ID no. 36046 | | | | | |
| | Ceres CLONE ID no. 1606506 | | | | | |
| | Ceres CLONE ID no. 546001 | | | | | |
| | Ceres CLONE ID no. 1554560 | | | | | |
| | Ceres CLONE ID no. 839727 | | | | | |
| | Ceres CLONE ID no. 664936 | | | | | |
| | Ceres CLONE ID no. 658438 | | | | | |
| | Ceres CLONE ID no. 1049262 | | | | | |
| | Ceres CLONE ID no. 632613 | | | | | |
| | Ceres CLONE ID no. 1390976 | | | | | |
| | Ceres CLONE ID no. 1457185 | | | | | |
| | Ceres CLONE ID no. 1482731 | | | | | |
| | Ceres CLONE ID no. 522921 | | | | | |
| | Ceres CLONE ID no. 1036726 | | | | | |
| | Ceres CLONE ID no. 513071 | | | | | |
| | Ceres CLONE ID no. 975672 | | | | | |
| | Ceres CLONE ID no. 273307 | | | | | |
| | Ceres CLONE ID no. 1055099 | | | | | |
| Ceres Clone ID no. 30469 | Ceres GI ID no. GI_15226675 | Globin | 13 | 152 | 184.6 | 404.9 |
| | Ceres Promoter 21876 | | | | | |
| | Ceres Promoter PT0668 | | | | | |
| | Ceres Promoter PT0535 | | | | | |
| | Ceres Promoter PT0585 | | | | | |
| | Ceres Promoter PT0613 | | | | | |
| | Ceres Promoter PT0625 | | | | | |
| | Ceres Promoter PT0633 | | | | | |
| | Ceres Promoter PT0650 | | | | | |
| | Ceres Promoter PT0660 | | | | | |
| | Ceres Promoter PT0665 | | | | | |
| | Ceres Promoter PT0672 | | | | | |
| | Ceres Promoter PT0676 | | | | | |
| | Ceres Promoter PT0678 | | | | | |
| | Ceres Promoter PT0683 | | | | | |
| | Ceres Promoter PT0688 | | | | | |
| | Ceres Promoter PT0695 | | | | | |
| | Ceres Promoter PT0708 | | | | | |
| | Ceres Promoter PT0710 | | | | | |
| | Ceres Promoter PT0723 | | | | | |
| | Ceres Promoter PT0740 | | | | | |
| | Ceres Promoter PT0743 | | | | | |
| | Ceres Promoter PT0758 | | | | | |
| | Ceres Promoter PT0829 | | | | | |
| | Ceres Promoter PT0837 | | | | | |
| | Ceres Promoter PT0838 | | | | | |
| | Ceres Promoter PT0848 | | | | | |
| | Ceres Promoter PT0863 | | | | | |
| | Ceres Promoter PT0879 | | | | | |
| | Ceres Promoter PT0886 | | | | | |
| | Ceres Promoter YP0007 | | | | | |
| | Ceres Promoter YP0008 | | | | | |
| | Ceres Promoter YP0019 | | | | | |
| | Ceres Promoter YP0028 | | | | | |
| | Ceres Promoter YP0039 | | | | | |
| | Ceres Promoter YP0050 | | | | | |
| | Ceres Promoter YP0086 | | | | | |
| | Ceres Promoter YP0088 | | | | | |
| | Ceres Promoter YP0092 | | | | | |
| | Ceres Promoter YP0096 | | | | | |
| | Ceres Promoter YP0097 | | | | | |
| | Ceres Promoter YP0101 | | | | | |
| | Ceres Promoter YP0102 | | | | | |
| | Ceres Promoter YP0103 | | | | | |
| | Ceres Promoter YP0107 | | | | | |
| | Ceres Promoter YP0110 | | | | | |
| | Ceres Promoter YP0111 | | | | | |
| | Ceres Promoter YP0115 | | | | | |
| | Ceres Promoter YP0117 | | | | | |
| | Ceres Promoter YP0119 | | | | | |
| | Ceres Promoter YP0120 | | | | | |
| | Ceres Promoter YP0121 | | | | | |
| | Ceres Promoter YP0128 | | | | | |
| | Ceres Promoter YP0137 | | | | | |

TABLE 7-continued

| | | | | | | | |
|---|---|---|---|---|---|---|---|
| | Ceres Promoter YP0143 | | | | | | |
| | Ceres Promoter YP0144 | | | | | | |
| | Ceres Promoter YP0156 | | | | | | |
| | Ceres Promoter YP0158 | | | | | | |
| | Ceres Promoter YP0188 | | | | | | |
| | Ceres Promoter YP0190 | | | | | | |
| | Ceres Promoter YP0212 | | | | | | |
| | Ceres Promoter YP0214 | | | | | | |
| | Ceres Promoter YP0263 | | | | | | |
| | Ceres Promoter YP0275 | | | | | | |
| | Ceres Promoter YP0285 | | | | | | |
| | Ceres Promoter YP0286 | | | | | | |
| | Ceres Promoter YP0337 | | | | | | |
| | Ceres Promoter YP0356 | | | | | | |
| | Ceres Promoter YP0374 | | | | | | |
| | Ceres Promoter YP0377 | | | | | | |
| | Ceres Promoter YP0380 | | | | | | |
| | Ceres Promoter YP0381 | | | | | | |
| | Ceres Promoter YP0384 | | | | | | |
| | Ceres Promoter YP0385 | | | | | | |
| | Ceres Promoter YP0396 | | | | | | |
| | Ceres Promoter p13879 | | | | | | |
| | Ceres Promoter p326 | | | | | | |
| | Ceres Promoter p32449 | | | | | | |
| | Ceres Promoter PD1367 | | | | | | |
| | Ceres Promoter p530c10 | | | | | | |
| | Ceres Promoter pOsFIE2-2 | | | | | | |
| | Ceres Promoter pOsMEA | | | | | | |
| | Ceres Promoter pOsYp102 | | | | | | |
| | Ceres Promoter pOsYp285 | | | | | | |
| | Ceres Promoter PT0565 | | | | | | |
| | Ceres Promoter YP0015 | | | | | | |
| | Ceres Promoter YP0087 | | | | | | |
| | Ceres Promoter YP0093 | | | | | | |
| | Ceres Promoter YP0108 | | | | | | |
| | Ceres Promoter YP0022 | | | | | | |
| | Ceres Promoter YP0080 | | | | | | |
| | Ceres Promoter PR0924 | | | | | | |
| | Ceres Promoter YP0388 | | | | | | |
| | Ceres Promoter PD0901 | | | | | | |
| | Ceres Promoter PT0623 | | | | | | |
| Ceres Clone ID no. 2403 | Truncated version of Ceres CLONE ID no. 100021733 | Ubiquitin family | 1 | 33 | | 87.6 | −83.1 |
| Ceres Clone ID no. 2403 | Truncated version of Ceres CLONE ID no. 1036726 | Ubiquitin family | 1 | 33 | Y | 87.6 | −83.1 |
| Ceres Clone ID no. 2403 | Truncated version of Ceres CLONE ID no. 1482731 | Ubiquitin family | 1 | 33 | Y | 87.1 | −85 |
| Ceres Clone ID no. 30469 | Truncated Version of Ceres CLONE ID no. 1554560 | Globin | 17 | 78 | Y | 185.7 | 61.3 |
| Ceres Clone ID no. 30469 | Truncated Version of Ceres CLONE ID no. 1802327 | Globin | 14 | 75 | Y | 191.4 | 67.2 |
| Ceres Clone ID no. 30469 | Truncated Version of Ceres CLONE ID no. 1876458 | Globin | 14 | 75 | | 191.9 | 67.7 |
| Ceres Clone ID no. 30469 | Truncated Version of Ceres CLONE ID no. 1879148 | Globin | 16 | 77 | | 185.7 | 61.3 |
| Ceres Clone ID no. 2403 | Truncated version of Ceres CLONE ID no. 1884696 | Ubiquitin family | 1 | 33 | Y | 87.6 | 65 |
| Ceres Clone ID no. 30469 | Truncated Version of Ceres CLONE ID no. 1916866 | Globin | 13 | 74 | Y | 188.3 | 65 |
| Ceres Clone ID no. 2403 | Truncated version of Ceres CLONE ID no. 1950105 | Ubiquitin family | 1 | 33 | Y | 87.6 | 60.7 |
| Ceres Clone ID no. 30469 | Truncated Version of Ceres CLONE ID no. 1990746 | Globin | 16 | 77 | | 184.9 | 60.7 |
| Ceres Clone ID no. 30469 | Truncated Version of Ceres CLONE ID no. 2033803 | Globin | 16 | 77 | | 184.9 | 60.7 |
| Ceres Clone ID no. 2403 | Truncated version of Ceres CLONE ID no. 2034916 | Ubiquitin family | 1 | 33 | | 87.6 | 63.3 |
| Ceres Clone ID no. 2403 | Truncated version of Ceres CLONE ID no. 513071 | Ubiquitin family | 1 | 33 | | 85.9 | 44.7 |
| Ceres Clone ID no. 2403 | Truncated version of Ceres CLONE ID no. 522921 | Ubiquitin family | 1 | 33 | Y | 87.6 | 22.4 |
| Ceres Clone ID no. 30469 | Truncated Version of Ceres CLONE ID no. 546001 | Globin | 13 | 74 | Y | 182.8 | 59.6 |
| Ceres Clone ID no. 30469 | Truncated Version of Ceres CLONE ID no. 651581 | Globin | 13 | 74 | | 185.7 | 63.9 |
| Ceres Clone ID no. 30469 | Truncated Version of Ceres CLONE ID no. 839727 | Globin | 14 | 75 | Y | 187.8 | 63.3 |
| Ceres Clone ID no. 30469 | Truncated Version of Public GI ID no. 11095158 | Globin | 13 | 76 | | 167.8 | 44.7 |

TABLE 7-continued

| Ceres Clone ID no. 30469 | Truncated Version of Public GI ID no. 12963875 | Globin | 8 | 69 | | 145.8 | 22.4 |
| Ceres Clone ID no. 30469 | Truncated Version of Public GI ID no. 14701800 | Globin | 21 | 82 | | 170.1 | 45.8 |
| Ceres Clone ID no. 30469 | Truncated Version of Public GI ID no. 15226675 | Globin | 13 | 74 | | 184.6 | 63 |
| Ceres Clone ID no. 30469 | Truncated Version of Public GI ID no. 15824736 | Globin | 13 | 74 | | 184.2 | 60.9 |
| Ceres Clone ID no. 30469 | Truncated Version of Public GI ID no. 30909306 | Globin | 13 | 74 | Y | 185.7 | 63.9 |
| Ceres Clone ID no. 30469 | Truncated Version of Public GI ID no. 37903656 | Globin | 10 | 71 | | 172.6 | 49.6 |
| Ceres Clone ID no. 30469 | Truncated Version of Public GI ID no. 62548111 | Globin | 13 | 74 | | 188.3 | 65 |

The invention claimed is:

1. A plant cell transformed with an exogenous nucleic acid, said exogenous nucleic acid comprising a polynucleotide sequence operably linked to a heterologous promoter, said polynucleotide sequence encoding a polypeptide comprising an amino acid sequence having 95 percent or greater amino acid sequence identity to the amino acid sequence of SEQ ID NO: 46, and wherein a transformed plant produced from said transformed plant cell has an increased level of cold tolerance as compared to the corresponding level of cold tolerance in a control plant of the same plant species that does not comprise said exogenous nucleic acid.

2. A transgenic plant comprising the transformed plant cell of claim 1.

3. The transgenic plant of claim 2, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

4. The transgenic plant of claim 2, wherein said polypeptide comprises the amino acid sequence of SEQ ID NO:46.

5. A vegetative product comprising a transgenic plant tissue from the transgenic plant according to claim 2.

6. The transformed plant cell of claim 1, wherein said polypeptide comprises an amino acid sequence that has 96 percent or greater amino acid sequence identity to the amino acid sequence of SEQ ID NO: 46.

7. The transformed plant cell of claim 1, wherein said polypeptide comprises an amino acid sequence that has 97 percent or greater amino acid sequence identity to the amino acid sequence of SEQ ID NO:46.

8. The transformed plant cell of claim 1, wherein said polypeptide comprises the amino acid sequence of SEQ ID NO:46.

9. The transgenic plant of claim 2, wherein said polypeptide comprises an amino acid sequence that has 96 percent or greater amino acid sequence identity to the amino acid sequence of SEQ ID NO:46.

10. The transgenic plant of claim 2, wherein said polypeptide comprises an amino acid sequence that has 97 percent or greater amino acid sequence identity to the amino acid sequence of SEQ ID NO:46.

11. A progeny of the transgenic plant of claim 2, wherein the progeny comprises the exogenous nucleic acid.

12. The transformed plant cell of claim 1, wherein said polynucleotide sequence comprising a nucleotide sequence having 95 percent or greater nucleotide sequence identity to the nucleotide sequence of SEQ ID NO: 108.

13. The transgenic plant of claim 2, wherein said polynucleotide sequence comprising a nucleotide sequence having 95 percent or greater nucleotide sequence identity to the nucleotide sequence of SEQ ID NO: 108.

* * * * *